US007695950B2

(12) United States Patent
Damude et al.

(10) Patent No.: US 7,695,950 B2
(45) Date of Patent: Apr. 13, 2010

(54) Δ5 DESATURASE AND ITS USE IN MAKING POLYUNSATURATED FATTY ACIDS

(75) Inventors: Howard Glenn Damude, Hockessin, DE (US); Dana M. Walters Pollak, Media, PA (US); Zhixiong Xue, Chadds Ford, PA (US); Quinn Qun Zhu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 421 days.

(21) Appl. No.: 11/748,637

(22) Filed: May 15, 2007

(65) Prior Publication Data

US 2007/0271632 A1    Nov. 22, 2007

Related U.S. Application Data

(60) Provisional application No. 60/801,119, filed on May 17, 2006.

(51) Int. Cl.
C12N 1/00 (2006.01)
C12N 15/74 (2006.01)
C07H 21/04 (2006.01)
(52) U.S. Cl. .................. 435/254.11; 435/471; 536/23.2
(58) Field of Classification Search ........................ None
See application file for complete search history.

(56) References Cited

U.S. PATENT DOCUMENTS

| 5,972,664 | A | 10/1999 | Knutzon et al. |
| 6,075,183 | A | 6/2000 | Knutzon et al. |
| 7,125,672 | B2 | 10/2006 | Picataggio et al. |
| 7,189,559 | B2 | 3/2007 | Damude et al. |
| 7,192,762 | B2 | 3/2007 | Maccol et al. |
| 7,198,937 | B2 | 4/2007 | Xue et al. |
| 7,202,356 | B2 | 4/2007 | Pollak et al. |
| 2006/0051847 | A1* | 3/2006 | Gunnarsson et al. ........ 435/134 |

FOREIGN PATENT DOCUMENTS

WO    WO 2006/012325 A1    2/2006
WO    WO 2006/012326 A1    2/2006

OTHER PUBLICATIONS

National Center for Biotechnology Information General Identifer No. 3859487, Nov. 11, 1998, D.S. Knutzon et al., Identification of Delta5-Desaturase From Mortierella Alpina by Heterologous Expression in Bakers' Yeast and Canola, AF067654.
National Center for Biotechnology Information General Identifier No. 4150955, Apr. 17, 2003, T. Saito et al., A Second Functional Delta5 Fatty Acid Desaturase in the Cellular Slime Mould Dictyostelium Discoideum, Accession No. AB022097.
National Center for Biotechnology Information General Identifier No. 16033740, Mar. 24, 2005, H. Hong et al., Isolation and Characterization of a Delta5 FA Desaturase From Pythium Irregulare by Heterologous Expression in Saccharomyces Cerevisiae and Oilseed Crops, Accession No. AAL13311.
National Center for Biotechnology Information General Identifier No. 23894018, Apr. 15, 2005, E. Hornung et al., Specific Formation of Arachidonic Acid by a Front-End Delta5-Desaturase From Phytophthora Megasperma, Accession No. CAD53323.
National Center for Biotechnology Information General Identifier No. 19879687, Aug. 23, 2002, F. Domergue et al., Cloning and Functional Characterization of Phaeodactylum Tricornutum Front-End Desaturases Involved in Eicosapentaenoic Acid Biosynthesis, Accession No. AAL92562.
National Center for Biotechnology Information General Identifier No. 66812304, Aug. 17, 2006, L. Eichinger et al., The Genome of the Social Amoeba Dictyostelium Discoideum, Accession No. XP640331.
Zank, T. et al., Database EBI Accession No. ADW96377 and abstract WO2005/012316A, Phaeodactylum tricornutum Delta-5 desaturase, Apr. 21, 2005, BASF Plant Sci GmbH.
Zank, T. et al., Database EBI Accession No. CS020052, Sequence 6 from Patent WO2005/012316, Feb. 23, 2005, BASF Plant Science GmbH.
U.S. Appl. No. 60/801,119, filed May 17, 2006, Howard Glenn Damude et al.
U.S. Appl. No. 60/915,733, filed May 3, 2007, Howard Glenn Damude et al.
U.S. Appl. No. 10/840,579, filed May 6, 2004, Stephen K. Picataggio et al.
U.S. Appl. No. 10/840,325, filed May 6, 2004, Narendra S. Yadav et al.
U.S. Appl. No. 10/869,630, filed Jun. 16, 2004, Stephen K. Picataggio et al.
U.S. Appl. No. 10/882,760, filed Jul. 1, 2004, Narendra S. Yadav et al.
U.S. Appl. No. 10/985,254, filed Nov. 10, 2004, Narendra S. Yadav et al.
U.S. Appl. No. 10/985,691, filed Nov. 10, 2004, Narendra S. Yadav et al.
U.S. Appl. No. 11/024,544, filed Dec. 29, 2004, Narendra S. Yadav et al.
U.S. Appl. No. 11/166,993, filed Jun. 24, 2005, Howard Glenn Damude et al.
U.S. Appl. No. 11/183,664, filed Jul. 18, 2005, Stephen K. Picataggio et al.
U.S. Appl. No. 11/185,301, filed Jul. 20, 2005, Zhixiong Xue et al.
U.S. Appl. No. 11/190,750, filed Jul. 27, 2005, Stephen K. Picataggio et al.
U.S. Appl. No. 11/198,975, filed Aug. 8, 2005, Quinn Qun Zhu et al.
U.S. Appl. No. 11/225,354, filed Sep. 13, 2005, Zhixiong et al.
U.S. Appl. No. 11/253,882, filed Oct. 19, 2005, Daniel Joseph Macool et al.

(Continued)

*Primary Examiner*—Elizabeth F McElwain
(74) *Attorney, Agent, or Firm*—Lynne M. Christenbury

(57) ABSTRACT

The present invention relates to a Δ5 desaturase, which has the ability to convert dihomo-γ-linolenic acid (DGLA; 20:3 ω-6) to arachidonic acid (ARA; 20:4 ω-6) and/or eicosatetraenoic acid (ETA; 20:4 ω-3) to eicosapentaenoic acid (EPA; 20:5 ω-3). Isolated nucleic acid fragments and recombinant constructs comprising such fragments encoding Δ5 desaturase along with a method of making long chain polyunsaturated fatty acids (PUFAs) using this Δ5 desaturase in oleaginous yeast are disclosed.

16 Claims, 12 Drawing Sheets

OTHER PUBLICATIONS

U.S. Appl. No. 11/264,784, filed Nov. 1, 2005, Howard Glenn Damude et al.
U.S. Appl. No. 11/264,737, filed Nov. 1, 2005, Howard Glenn Damude et al.
U.S. Appl. No. 11/265,761, filed Nov. 2, 2005, Howard Glenn Damude et al.
U.S. Appl. No. 60/795,810, filed Apr. 28, 2006, Howard Glenn Damude et al.
U.S. Appl. No. 60/793,575, filed Apr. 20, 2006, Zhixiong et al.
U.S. Appl. No. 60/796,637, filed May 1, 2006, Narendra S. Yadav et al.
U.S. Appl. No. 60/801,172, filed May 17, 2006, Howard Glenn Damude et al.
U.S. Appl. No. 60/853,563, filed Oct. 23, 2006, Howard Glenn Damude et al.
U.S. Appl. No. 60/855,177, filed Oct. 30, 2006, Zhixiong et al.
U.S. Appl. No. 11/601,563, filed Nov. 16, 2006, Howard Glenn Damude et al.
U.S. Appl. No. 11/601,564, filed Nov. 16, 2006, Howard Glenn Damude et al.
U.S. Appl. No. 11/635,258, filed Dec. 7, 2006, Howard Glenn Damude et al.
U.S. Appl. No. 11/613,420, filed Dec. 20, 2006, John E. Seip et al.
U.S. Appl. No. 60/909,790, filed Apr. 3, 2007, Howard Glenn Damude et al.
U.S. Appl. No. 60/911,925, filed Apr. 16, 2007, Howard Glenn Damude et al.
U.S. Appl. No. 60/910,831, filed Apr. 10, 2007, Howard Glenn Damude et al.
J. Dyerberg et al., Fatty Acid Composition of the Plasma Lipids in Greenland Eskimos, Amer. J. Clin. Nutr., 1975, vol. 28:958-966.
J. Dyerberg et al., Eicosapentaenoic Acid and Prevention of Thrombosis and Atherosclerosis? Lancet., 1978, vol. 2:117-119.
H. Shimokawa, Beneficial Effects of Eicosapentaenoic Acid on Endothelial Vasodilator Functions in Animals and Humans, World Rev. Nutr. Diet, 2001, vol. 88:100-108.
C. Von Schacky et al., 3 Fatty Acids From Eskimos to Clinical Cardiology—What Took Us So Long? World Rev. Nutr. Diet, 2001, vol. 88:90-99.
National Center for Biotechnology Information General Identifier No. 6842049, Jun. 21, 2000, H.P. Cho et al., Cloning, Expression, and Fatty Acid Regulation of the Human Delta-5 Desaturase, Accession No. AF199596.
National Center for Biotechnology Information General Identifier No. 7861969, May 17, 2000, A.E. Leonard et al., CDNA Cloning and Characterization of Human Delta5-Desaturase Involved in the Biosynthesis of Arachidonic Acid, Accession No. AF22673.
National Center for Biotechnology Information General Identifier No. 11386008, Aug. 13, 2001, R. Zolfaghari et al., Fatty Acid Delta-5 Desaturase MRNA is Regulated by Dietary Vitamin A and Exogenous Retinoic Acid in Liver of Adult Rats, Accession No. AF320509.
Natiional Center for Biotechnology Information General Identifier No. 16151828, Oct. 16, 2001, T. Matsuzaka et al., Dual Gene Regulation of Mouse Delta-5 and -6 Desaturases by SREBP-1 and PPAR Alpha, Accession No. AB072976.
National Center for Biotechnology Information General Identifier No. 20069122, Apr. 8, 2002, X. Qui et al., Identification of Delta 4 Fatty Acid Desaturase From Thraustochytrium SP. Involved in the Biosynthesis of Docosahexanoic Acid by Heterologous Expression in Saccharomyces Cerevisiae and Brassica Juncea, Accession No. AF489588.
National Center for Biotechnology Information General Identifier No. 23894017, Apr. 15, 2005, E. Hornung et al., Specific Formation of Arachidonic Acid by a Front-End Delta5-Desaturase From Phytophthora Megasperma, Accession No. AJ510244.
National Center for Biotechnology Information General Identifier No. 16033739, Mar. 24, 2005, H. Hong et al., Isolation and Characterization of Delta 5 FA Desaturase From Pythium Irregulare by Heterologous Expression in Saccharomyces Cerevisiae and Oilseed Crops, Accession No. AF419297.
International Preliminary Report on Patentability and Written Opinion in corresponding PCT application PCT/US2007/011776, dated Nov. 27, 2008.

* cited by examiner

```
       721 CAAAGCGTACTTTGATTCACCACTTCCAGGCCTTCTATTACCTTTTCGTCTTGGCGGA SEQ ID NO:1
       721 CCCAAGCGAACCCTCATTCATTCACCTTCCAAGCCTTCTACTATCTGTTTGTCCTTGTGC SEQ ID NO:3

781 TACTGGGTCTCTTCGGTCTCTTCAACCCCTCAAATTTTGGACTTGCAACACCGCGGTCAA SEQ ID NO:1
       781 TACTGGGTGTCTTCGGTGTCTTCAACCCTCAGATCCTGGACCTTCAGCACCACCGAGGTG SEQ ID NO:3

841 GCGGTTGGAATGAAAATGGAGAACGATTACATTGCCAAAAGCCGAAAGTATGCCATCTTC SEQ ID NO:1
       841 GCTGTCGGCATGAAGATGGAGAACGACTACATTGCCAAGTCTCGAAAGTACGCTATCTTC SEQ ID NO:3

901 TTGCGTCTCTTGTATATTTTACACCAACATTGTCGCTCCAAAACCAAGGCTTCTCG SEQ ID NO:1
       901 CTGCGACTCCTGTACATCCTGTACATCCTACACCAACATTGTGGCTCCAGAACCAAGGCTTTTCG SEQ ID NO:3

961 TTGACCGTGGTCGCCACACATTTGACCACCATTTCTTACTACTTTGAAAACGCCGACT SEQ ID NO:1
       961 CTCACCGTCGTTGCTCACACATTCGAGAACACAACTTCGAGAACAGCGAGATCGGGATCCCAGTTGACCTGACCCTCGCTACT SEQ ID NO:3

1021 CTTTTTGCCTTGTCGCAACATTTGAAAACGCCGATCGCGATCCCACTTACGAGGCCCGC SEQ ID NO:1
      1021 CTGTTCGCCCTCGTCCAACAACTTCGAGAACAGCGAGATCGGGATCCCAGTCCACGAGGCTCGA SEQ ID NO:3

1081 AAGGGAGGAGAGCCCTGTTGGTTGTTGGTTCAAGTCGCAAGTCGTCGTTACGGA SEQ ID NO:1
      1081 AAGGGAGGCGAGCCCTGCCTGTCTGTTGGTTGCAAGTGGAAAACCTCTCTACTACGGT SEQ ID NO:3

1141 GGTTTCATCTCGGGTTGCTTGACCGGGCGGACTCAACTTCCAACTTCAACCACCACTGTTC SEQ ID NO:1
      1141 GGCTTCATTTCGGTTGCCTTACAGCGGACTCAACTTCAACTTTCAGGTCGAGCATCACCTGTTT SEQ ID NO:3

1201 CCTCGTATGAGTTCGGCCCTGGTACCCCCTACATTGCCCCCTACTGTTCGAGAGGTTTGCAAA SEQ ID NO:1
      1201 CCTCGAATGTCCTCTGCCTGGTACCCTGGTACCCTGGTACTACCCGCCTGCCGTTGAGAGGTCTGCAAA SEQ ID NO:3

1261 AAGCACGGAGTCAAGTACGCCATACTACTCCCTGGGTCTGGCAAAACTTGATTTCAACTGTC SEQ ID NO:1
      1261 AAGCACGGCGTCAAGTACGCGCTACTATCCCTGGGTGTGGCAGAACTCATCTCGACGTC SEQ ID NO:3

1321 AAGTATCTGCATCAAAGCGGAACTGGACCGGAAGAATGGCGCCAACCCCTACTCG SEQ ID NO:1
      1321 AAGTACCTGCATCAGTCGGATCCGGAACTCGGCTGGTGTGGAAGAGAACGGTGCCAATCCCTACTCT SEQ ID NO:3

1381 GGAAAATTGTAA                                                 SEQ ID NO:1
      1381 GGCAAGCTGTAA                                                 SEQ ID NO:3
```

Figure 8A

| | | | | | |
|---|---|---|---|---|---|
| 1 | MGKGGDGGAQAVSGTDASL - - AEVSSVDSKSVHVVLYG | SEQ ID NO:18 (Pavlova lutheri).pro |
| 1 | MGRGGDSSGQAAHPAAELAVPSDRAEVSNADSKALHI - VLYG | SEQ ID NO:66 (Pavlova salina).pro |
| 1 | MK - - - S - KRQALP - - - - - - - - - - - - - - - - LTID | SEQ ID NO:16 (Euglena gracillis).pro |
| 1 | MS - - - - TLDRQSIFTIKELESI - SQRIHDGDEEAMKFIIID | SEQ ID NO:65 (Rhizopus stolonifer).pro |
| 1 | MS - - - - TLDRQSIFTIKELESI - SQRIHDGDEEAMKFIIID | SEQ ID NO:53 (Rhizopus stolonifer).pro |

| 37 | KRV - DVTKFQKAHPGGSKVFRIFQERDATEQFESYHSPKA | SEQ ID NO:18 (Pavlova lutheri).pro |
| 41 | KRV - DVTKFHPGGSKVFRIFQDRDATEQFESYHSKRA | SEQ ID NO:66 (Pavlova salina).pro |
| 14 | GTTYDVSAWVNFHPGGAEIIENYQGRDATDAFMVMHSQEA | SEQ ID NO:16 (Euglena gracillis).pro |
| 37 | KKVYDVTEFIEDHPGGAQVLLTHVGKDASDVFHAMHPESA | SEQ ID NO:65 (Rhizopus stolonifer).pro |
| 37 | KKVYDVTEFIEDHPGGAQVLLTHVGKDASDVFHAMHPESA | SEQ ID NO:53 (Rhizopus stolonifer).pro |

| 76 | IKMMEGMLKKSEDAPASVPLPSRSTMGTEFFKEMIERHKRA | SEQ ID NO:18 (Pavlova lutheri).pro |
| 80 | IKMMEGMLKKSEDAPADTPLPSQSPMGKDFKAMIERHVAA | SEQ ID NO:66 (Pavlova salina).pro |
| 54 | FDKLKR - MPKINPSSELPPQAAVNEAQEDFRKLREELIAT | SEQ ID NO:16 (Euglena gracillis).pro |
| 77 | YEVLNNYFVGDVQETVVTEKSSSSAQFAVEMRQLRDQLKKE | SEQ ID NO:65 (Rhizopus stolonifer).pro |
| 77 | YEVLNNYFVGDVQETVVTEKSSSSAQFAVEMRQLRDQLKKE | SEQ ID NO:53 (Rhizopus stolonifer).pro |

| 116 | GLYDPCPLDELFKLTIVLAPIFVGAYLV - - - - RSGV - SPL | SEQ ID NO:18 (Pavlova lutheri).pro |
| 120 | GYYPCPLDELFKLSLVLLPTFFAGMYML - - - - KAGVGSPF | SEQ ID NO:66 (Pavlova salina).pro |
| 93 | GMFDASPLWYSYKISTTLGLGVLGYFLMVQYQM - - - YF | SEQ ID NO:16 (Euglena gracillis).pro |
| 117 | GYFHSSKLFYAYKVLSTLAICIAGLSPLYAYGRTSTLAVV | SEQ ID NO:65 (Rhizopus stolonifer).pro |
| 117 | GYFHSSKLFYAYKVLSTLAICIAGLSLLYAYGRTSTLAVV | SEQ ID NO:53 (Rhizopus stolonifer).pro |

| 151 | AGALSMGFGFYLDGWLAHDYLHHAVFKGSVNTLVKANNAM | SEQ ID NO:18 (Pavlova lutheri).pro |
| 156 | CGALMVSFGWYLDGWLAHDYLHHSVFKFKGSVARTVGWNNAA | SEQ ID NO:66 (Pavlova salina).pro |
| 128 | IGAVLLGMHYFQQMGWLSHDICHHQTFFKNR - - - NWNNLV | SEQ ID NO:16 (Euglena gracillis).pro |
| 157 | ASAITVGIFWQQCGWLAHDFGHHQCFFEDR - - - - TWNDVL | SEQ ID NO:65 (Rhizopus stolonifer).pro |
| 157 | ASAITVGIFWQQCGWLAHDFGHHQCFFEDR - - - - TWNDVL | SEQ ID NO:53 (Rhizopus stolonifer).pro |

| 191 | GYALG - FLQGYDVAWWRARHNTHHVCTNEDGSDPPDIKTAP | SEQ ID NO:18 (Pavlova lutheri).pro |
| 196 | GYFLG - FVQGYAVEWWRARHNTHHVCTNEDGSDPPDIKTAP | SEQ ID NO:66 (Pavlova salina).pro |
| 163 | GLVFGNFCQGFSLSWWKDRHNAHHAATNVQGHDPPDIDNLP | SEQ ID NO:16 (Euglena gracillis).pro |
| 192 | VVFLGNFCQGFSLSWWKNKHNTHHASTNVHGQDPPDIDTAP | SEQ ID NO:65 (Rhizopus stolonifer).pro |
| 192 | VVFLGNFCQGFSLSWWKNKHNTHHASTNVHGQDPPDIDTAP | SEQ ID NO:53 (Rhizopus stolonifer).pro |

Figure 8B

```
                                                                              250                                    260                                    270                                     280
230   L L I Y - - - - - - - - - - - - - V R E N P S I A K R L - - - N F F Q R W Q Q Y Y Y       SEQ ID NO:18 (Pavlova lutheri).pro
235   L L L Y - - - - - - - - - - - - - V R N K P S I A K R L - - - N A F Q R Y Q Q Y Y Y       SEQ ID NO:66 (Pavlova salina).pro
203   L L A W S E - - - - - - - - V R N K P S I S R K L I Q F Q - - - Q Y Y F                  SEQ ID NO:16 (Euglena gracilis).pro
232   V L L W D E Y A S A A Y Y A S L D Q E P T M V S R F L A E Q V L P H Q T R Y F F           SEQ ID NO:65 (Rhizopus stolonifer).pro
232   V L L W D E Y A S A A Y Y A S L D Q E P T M V S R F L A E Q V L P H Q T R Y F F           SEQ ID NO:53 (Rhizopus stolonifer).pro 290                                    300                                    310                                     320
256   V P T M A I L D L Y W R L E S I A Y Y A V R - - L P K M W M Q A A - - - - - - - - -       SEQ ID NO:18 (Pavlova lutheri).pro
261   V P V M A I L D L Y W R L E S I A Y Y A V M R - - L P K M L P Q A L - - - - - - - -       SEQ ID NO:66 (Pavlova salina).pro
230   L V I - C I L L R F I W C F Q S V - - L T V R S L - K D R D N Q F Y R S Q Y K K           SEQ ID NO:16 (Euglena gracilis).pro
272   F I L - A F A R L S W A L Q S L S Y S F K K E S I - N K S R Q L N L F - - - - - -         SEQ ID NO:65 (Rhizopus stolonifer).pro
272   F I L - A F A R L S W A L Q S L S Y S F K K E S I - N K S R Q L N L F - - - - - -         SEQ ID NO:53 (Rhizopus stolonifer).pro 330                                    340                                    350                                     360
287   - - - - A L A A H Y A L L C W V F A A H L N L I P L M M - V A R G F                       SEQ ID NO:18 (Pavlova lutheri).pro
292   - - - - A L V A H Y A L I V A W V F A G N Y H L L L V F - V S E L V G G F                 SEQ ID NO:66 (Pavlova salina).pro
266   E A I - G L A L H W T L L K T L F H L F - F M P S I L T S L L V F F L V S Q A T T G Y     SEQ ID NO:16 (Euglena gracilis).pro
305   E R V C I - V G H W A L S A - F C I - Y S W C S N V Y H M V L F F L V S Q A T T G Y       SEQ ID NO:65 (Rhizopus stolonifer).pro
305   E R V C I - V G H W A L F A - F C I - Y S W C S N V Y H M V L F F L V S Q A T T G Y       SEQ ID NO:53 (Rhizopus stolonifer).pro 370                                    380                                    390                                     400
316   A T G I V V F A T H Y G E D I L D R E H V E G M T L V E Q T A K T S R N I - T G G         SEQ ID NO:18 (Pavlova lutheri).pro
321   G T G I T V F A T H Y G E D I L D A D Q V R H M T L V E Q T A L T S R N I - S G G G       SEQ ID NO:66 (Pavlova salina).pro
305   G I A L - V V F M N H H Y P L E K I - G D S V W D G H G F S V G G Q I - H E T M N I - R R G   SEQ ID NO:16 (Euglena gracilis).pro
344   T L A L V F A L N H N G M P V I - T E E K A E S M E F F E I - Q V I - T G R D V T L S     SEQ ID NO:65 (Rhizopus stolonifer).pro
344   T L A L V F A L N H N G M P V I - T E E K A E S M E F F E I - Q V I - T G R D V T L S     SEQ ID NO:53 (Rhizopus stolonifer).pro 410                                    420                                    430                                     440
356   W L V N V L T G F I S L Q T E H H L F P M M P T G N L M T I - Q P E V R D F F K K         SEQ ID NO:18 (Pavlova lutheri).pro
361   W L V N V L T G F I S L Q T E H H L F P M M P T G N L M T I - Q P E V R A F F K K         SEQ ID NO:66 (Pavlova salina).pro
345   I I - T D W F M G G L N Y Q I E H H L F W P T L P R H N L L P T A V S Y Q V E Q V L C Q K SEQ ID NO:16 (Euglena gracilis).pro
384   P L G D W F M G G L N Y Q I E H H V F P N M P R H N L L P T V K P M V K S L C Q K         SEQ ID NO:65 (Rhizopus stolonifer).pro
384   P L G D W F M G G L N Y Q I E H H V F P N M P R H N L L P T V K P M V K S L C Q K         SEQ ID NO:53 (Rhizopus stolonifer).pro 450                                    460                                    470
396   H G L E Y R E G N L F Q C V H Q N I - K A L A F E H L L H                                 SEQ ID NO:18 (Pavlova lutheri).pro
401   H G L E Y R E G N L I - E C V R Q N L - L L R Y L A F E H L L                             SEQ ID NO:66 (Pavlova salina).pro
385   H N L P Y Y R N P L P H E G Q L V - L L R Y L A V F A R M A E K Q P A G K A L             SEQ ID NO:16 (Euglena gracilis).pro
424   Y D I - N Y H D T G F L K G T L E V L Q T L D I - T S K L S L - Q L S K K S F             SEQ ID NO:65 (Rhizopus stolonifer).pro
424   Y D I - N Y H D T G F L K G T L E V L Q T L D I - T S K L S L - Q L S K K S F             SEQ ID NO:53 (Rhizopus stolonifer).pro
```

| Fatty Acid | Clone | Gene | Fatty acid composition (wt.%) |||||||||||||
|---|---|---|---|---|---|---|---|---|---|---|---|---|---|---|---|
| | | | 16:0 | 16:1 | 18:0 | 18:1 | LA | GLA | ALA | STA | EDA | SCI | DGLA | ARA | ETrA | JUP | ETA | EPA |
| None | pY98 | MaD5 | 9.5 | 9.5 | 0.7 | 37.4 | 42.8 | 0.0 | 0.0 | 0.0 | 0.0 | 0.0 | 0.0 | 0.0 | 0.0 | 0.0 | 0.0 | 0.0 |
| | pDMW368 | RD5 | 10.0 | 9.3 | 0.8 | 39.4 | 40.5 | 0.0 | 0.0 | 0.0 | 0.0 | 0.0 | 0.0 | 0.0 | 0.0 | 0.0 | 0.0 | 0.0 |
| EDA | pY98 | MaD5 | 9.8 | 8.2 | 0.8 | 39.7 | 34.1 | 0.0 | 0.0 | 0.0 | 7.1 | 0.2 | 0.0 | 0.0 | 0.0 | 0.0 | 0.0 | 0.0 |
| | pDMW368 | RD5 | 8.9 | 8.2 | 1.1 | 41.2 | 32.7 | 0.0 | 0.0 | 0.0 | 5.4 | 2.6 | 0.0 | 0.0 | 0.0 | 0.0 | 0.0 | 0.0 |
| DGLA | pY98 | MaD5 | 12.0 | 6.8 | 1.4 | 38.8 | 19.3 | 0.6 | 0.0 | 0.0 | 0.0 | 0.0 | 18.2 | 3.0 | 0.0 | 0.0 | 0.0 | 0.0 |
| | pDMW368 | RD5 | 12.1 | 7.0 | 1.2 | 40.3 | 18.3 | 0.6 | 0.0 | 0.0 | 0.0 | 0.0 | 10.2 | 10.3 | 0.0 | 0.0 | 0.0 | 0.0 |
| ETrA | pY98 | MaD5 | 8.9 | 7.2 | 1.0 | 41.2 | 17.2 | 0.0 | 12.1 | 0.0 | 0.0 | 0.0 | 0.0 | 0.0 | 11.7 | 0.6 | 0.0 | 0.0 |
| | pDMW368 | RD5 | 8.1 | 7.3 | 0.9 | 42.3 | 16.1 | 0.0 | 12.1 | 0.0 | 0.0 | 0.0 | 0.0 | 0.0 | 10.1 | 3.1 | 0.0 | 0.0 |
| ETA | pY98 | MaD5 | 11.9 | 6.5 | 0.8 | 38.5 | 12.2 | 0.0 | 0.0 | 0.4 | 0.0 | 0.0 | 0.0 | 0.0 | 0.0 | 0.0 | 26.1 | 3.6 |
| | pDMW368 | RD5 | 11.9 | 6.4 | 0.8 | 40.0 | 11.1 | 0.0 | 0.0 | 0.4 | 0.0 | 0.0 | 0.0 | 0.0 | 0.0 | 0.0 | 18.8 | 10.5 |

B

| Fatty Acid | Clone | Gene | % delta-5 desat | Ratio Desat R/Ma | Ratio Prod/By-Prod | Ratio Prod/By-Prod R/Ma | Ratio n-6/n-3 |
|---|---|---|---|---|---|---|---|
| None | pY98 | MaD5 | | | | | |
| | pDMW368 | RD5 | | | | | |
| EDA | pY98 | MaD5 | 3.4 | 9.7 | 4.17 | 0.37 | 0.68 |
| | pDMW368 | RD5 | 32.6 | | 1.54 | | 1.40 |
| DGLA | pY98 | MaD5 | 14.0 | 3.6 | | | 1.17 |
| | pDMW368 | RD5 | 50.3 | | | | 1.40 |
| ETrA | pY98 | MaD5 | 4.9 | 4.7 | 2.44 | 0.63 | |
| | pDMW368 | RD5 | 23.2 | | 1.55 | | |
| ETA | pY98 | MaD5 | 12.0 | 3.0 | | | |
| | pDMW368 | RD5 | 35.9 | | | | | ns.com/search?q=US+7,695,950+B2

Δ5 DESATURASE AND ITS USE IN MAKING POLYUNSATURATED FATTY ACIDS

This application claims the benefit of U.S. Provisional Patent Application 60/801,119, filed May 17, 2006.

FIELD OF THE INVENTION

This invention is in the field of biotechnology. More specifically, this invention pertains to the identification of nucleic acid fragments encoding a Δ5 fatty acid desaturase enzyme and the use of this desaturase in making long chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg, J. et al., *Amer. J. Clin. Nutr.*, 28:958-966 (1975); Dyerberg, J. et al., *Lancet*, 2(8081):117-119 (Jul. 15, 1978); Shimokawa, H., *World Rev. Nutr. Diet*, 88:100-108 (2001); von Schacky, C. and Dyerberg, J., *World Rev. Nutr. Diet*, 88:90-99 (2001)). And, numerous other studies document wide-ranging health benefits conferred by administration of ω-3 and/or ω-6 PUFAs against a variety of symptoms and diseases (e.g., asthma, psoriasis, eczema, diabetes, cancer).

A variety of different hosts including plants, algae, fungi and yeast are being investigated as means for commercial PUFA production. Genetic engineering has demonstrated that the natural abilities of some hosts (even those natively limited to LA and ALA fatty acid production) can be substantially altered to result in high-level production of various long-chain ω-3/ω-6 PUFAs. Whether this is the result of natural abilities or recombinant technology, production of arachidonic acid (ARA; 20:4 ω-6), eicosapentaenoic acid (EPA; 20:5 ω-3) and docosahexaenoic acid (DHA; 22:6 (ω-3) may all require expression of a Δ5 desaturase.

Most Δ5 desaturase enzymes identified so far have the primary ability to convert dihomo-γ-linolenic acid (DGLA; 20:3 (ω-6) to ARA, with secondary activity in converting eicosatetraenoic acid (ETA; 20:4 (0-3) to EPA (where DHA is subsequently synthesized from EPA following reaction with an additional $C_{20/22}$ elongase and a Δ4 desaturase). The Δ5 desaturase has a role in both the Δ6 desaturase/Δ6 elongase pathway (which is predominantly found in algae, mosses, fungi, nematodes and humans and which is characterized by the production of γ-linoleic acid (GLA; 18:3 (ω-6) and/or stearidonic acid (STA; 18:4 (ω-3)) and the Δ9 elongase/Δ8 desaturase pathway (which operates in some organisms, such as euglenoid species and which is characterized by the production of eicosadienoic acid (EDA; 20:2 ω-6) and/or eicosatrienoic acid (ETrA; 20:3 (ω-3)) (FIG. 1).

Based on the role Δ5 desaturase enzymes play in the synthesis of e.g., ARA, EPA and DHA, there has been considerable effort to identify and characterize these enzymes from various sources. As such, numerous Δ5 desaturases have been disclosed in both the open literature (e.g., GenBank Accession No. AF199596, No. AF226273, No. AF320509, No. AB072976, No. AF489588, No. AJ510244, No. AF419297, No. AF07879, No. AF067654 and No. AB022097) and the patent literature (e.g., U.S. Pat. Nos. 5,972,664 and 6,075,183), see also, commonly owned, co-pending 60/801,172, disclosing amino acid and nucleic acid sequences for a Δ5 desaturase enzyme from *Euglena gracilis*, and No. 60/915, 733, disclosing amino acid and nucleic acid sequences for a Δ5 desaturase enzyme from *Euglena anabaena*.

Despite the disclosures cited above, it was desirable for the Applicants herein to identify and isolate additional genes encoding Δ5 desaturases that would be suitable for heterologous expression in a variety of host organisms for use in the production of ω-3/ω-6 fatty acids.

Applicants have solved the stated problem by isolating a gene encoding Δ5 desaturase from *Peridinium* sp. CCMP626.

SUMMARY OF THE INVENTION

The present invention relates to new genetic constructs encoding polypeptides having Δ5 desaturase activity, and their use in algae, bacteria, yeast, and fungi for the production of PUFAs.

Accordingly the invention provides an isolated nucleic acid molecule selected from the group consisting of:
 (a) an isolated nucleotide sequence encoding a Δ5 desaturase enzyme as set forth in SEQ ID NO:2;
 (b) an isolated nucleotide sequence that hybridizes with (a) under the following hybridization conditions: 0.1×SSC, 0.1% SDS, 65° C. and washed with 2×SSC, 0.1% SDS followed by 0.1×SSC, 0.1% SDS; and,
 (c) an isolated nucleotide sequence that is completely complementary to (a) or (b).

In a preferred embodiment the nucleic acid molecule encoding the Δ5 desaturase of the invention are codon optimized for expression in the appropriate host.

In a preferred embodiment the invention provides an isolated nucleic acid molecule comprising a first nucleotide sequence encoding a Δ5 desaturase enzyme of at least 463 amino acids that has at least 95% identity based on BLASTP algorithms when compared to a polypeptide having the sequence as set forth in SEQ ID NO:2;
 or a second nucleotide sequence comprising the complement of the first nucleotide sequence.

The invention additionally provides genetic chimera comprising the nucleic acids encoding the Δ5 desaturase enzymes described herein as well as transformed host comprising the same.

In a preferred embodiment the invention provides a method for the production of arachidonic acid comprising:
 a) providing a host cell comprising:
  (i) an isolated nucleotide molecule encoding a Δ5 desaturase polypeptide having at least 95% identity when compared to a polypeptide having the amino acid sequence as set forth in SEQ ID NO:2, based on BLASTP algorithms; and,
  (ii) a source of dihomo-γ-linoleic acid;
 b) growing the host cell of step (a) under conditions wherein the nucleic acid fragment encoding the Δ5 desaturase polypeptide is expressed and the dihomo-γ-linoleic acid is converted to arachidonic acid; and,
 c) optionally recovering the arachidonic acid of step (b).

Alternatively the invention provides methods for the production of eicosapentaenoic acid comprising:

a) providing a host cell comprising:
   (i) an isolated nucleotide molecule encoding a Δ5 desaturase polypeptide having at least 95% identity when compared to a polypeptide having the amino acid sequence as set forth in SEQ ID NO:2, based on BLASTP algorithms; and,
   (ii) a source of eicosatetraenoic acid;
b) growing the host cell of step (a) under conditions wherein the nucleic acid fragment encoding the Δ5 desaturase polypeptide is expressed and the eicosatetraenoic acid is converted to eicosapentaenoic acid; and,
c) optionally recovering the eicosapentaenoic acid of step (b).

In another embodiment the invention provides a method of obtaining a nucleic acid fragment encoding a Δ5 desaturase enzyme comprising:
a.) probing a genomic library with:
   i.) an isolated nucleic acid fragment encoding an amino acid sequence as set forth in SEQ ID NO:2; or,
   ii.) an isolated nucleic acid fragment that is complementary to (i);
b.) identifying a DNA clone that hybridizes with the nucleic acid fragment of step (a); and,
c.) sequencing the genomic fragment that comprises the clone identified in step (b);

wherein the sequenced genomic fragment encodes a Δ5 desaturase enzyme.

Similarly the invention provides a method of obtaining a nucleic acid fragment encoding a Δ5 desaturase enzyme comprising:
a.) synthesizing at least one oligonucleotide primer corresponding to a portion of the sequence selected from the group consisting of SEQ ID NOs:1 and 3; and,
b.) amplifying an insert present in a cloning vector using the oligonucleotide primer of step (a);

wherein the amplified insert encodes a portion of an amino acid sequence encoding a Δ5 desaturase enzyme.

BRIEF DESCRIPTION OF THE DRAWINGS AND SEQUENCE LISTINGS

FIG. 3 shows a portion of an alignment between and among Δ5 desaturase proteins and Δ8 desaturase proteins using a Clustal W analysis (MegAlign™ program of DNASTAR software).

Figure 4:
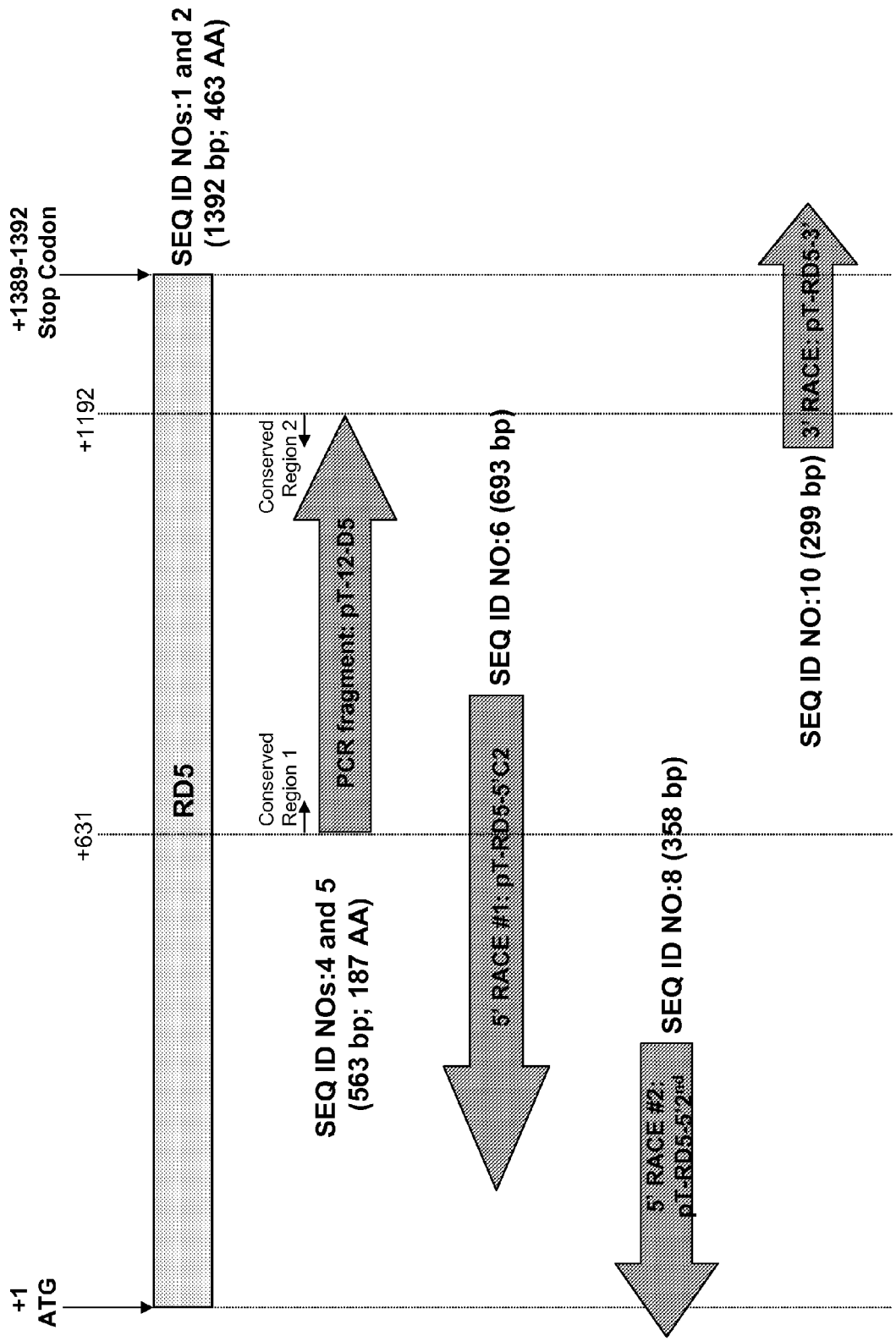

FIG. 4 graphically represents the relationship between SEQ ID NOs:1, 2, 4, 5, 6, 8 and 10, each of which relates to the *Peridinium* sp. CCMP626 Δ5 desaturase.

Figure 5:
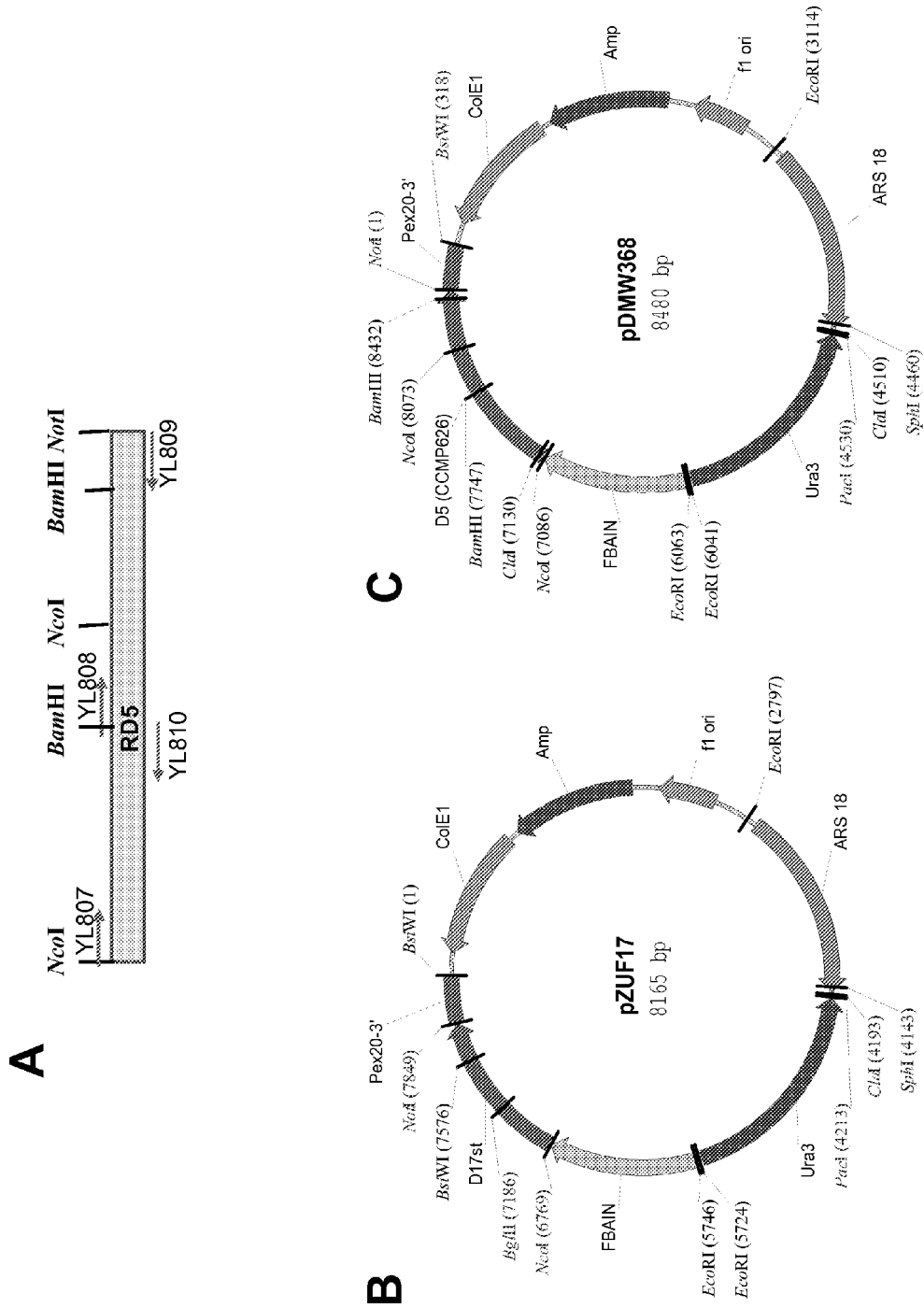

FIG. 5A illustrates the cloning strategy utilized for amplification of the *Peridinium* sp. CCMP626 Δ5 desaturase gene (RD5). FIG. 5B is a plasmid map of pZUF17, while FIG. 5C is a plasmid map of pDMW368.

Figure 6:

FIG. 6 provides plasmid maps for the following: (A) pKUNF12T6E; (B) pRD5S; and, (C) pZURD5S.

Figure 7A:
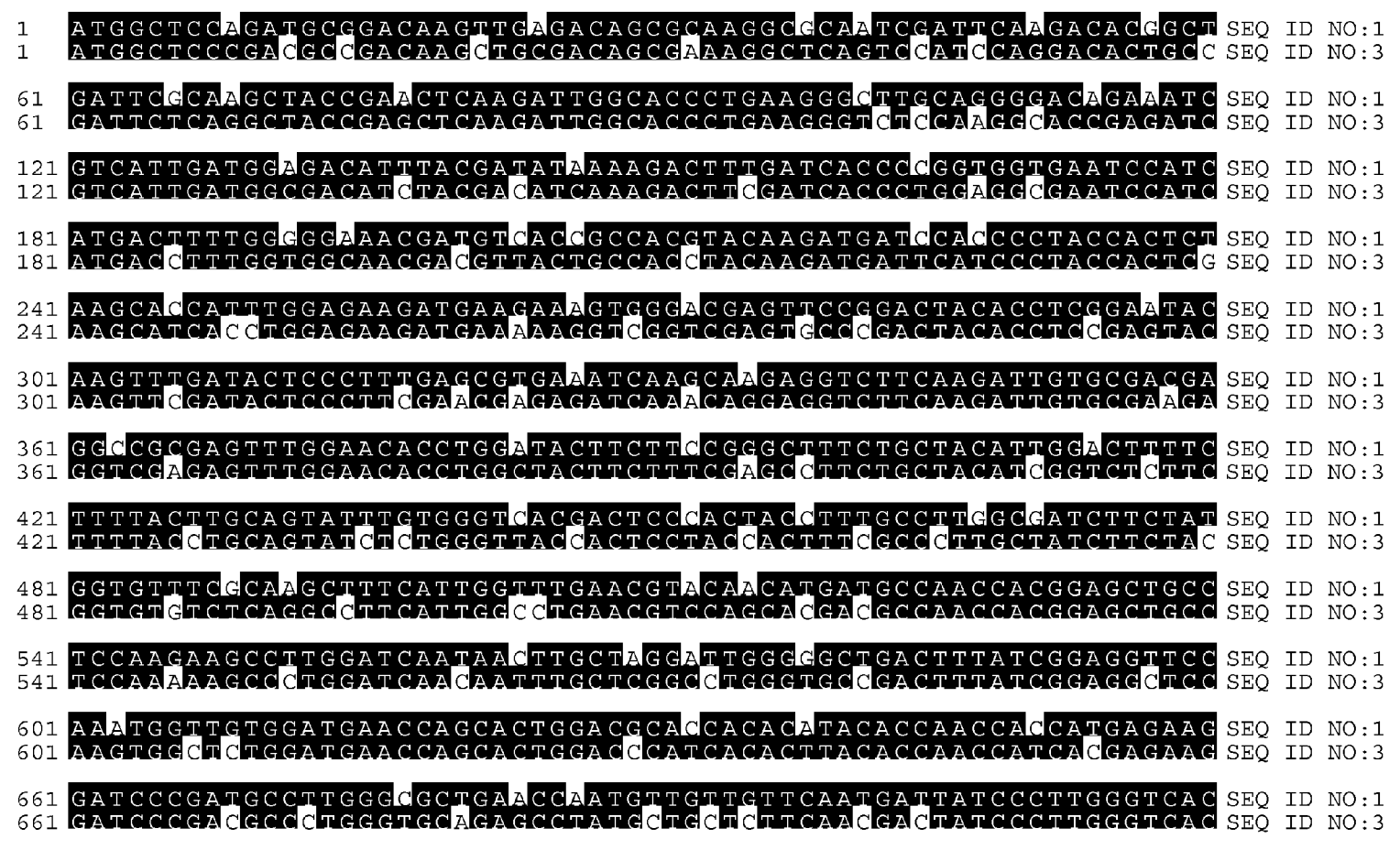

FIGS. 7A and 7B show a comparison of the DNA sequence of the *Peridinium* sp. CCMP626 Δ5 desaturase gene (designated as "RD5"; SEQ ID NO:1) and the synthetic gene (designated as "RD5S"; SEQ ID NO:3) codon-optimized for expression in *Yarrowia lipolytica*.

FIGS. 8A and 8B show a Clustal V alignment (with default parameters) of a *Pavlova lutheri* Δ8 desaturase (SEQ ID NO:18), a *Pavlova salina* Δ8 desaturase (SEQ ID NO:66), a *Euglena gracilis* Δ8 desaturase (SEQ ID NO:16) and two different *Rhizopus stolonifer* Δ6 fatty acid desaturases (SEQ ID NOs:53 and 65).

Figure 9:
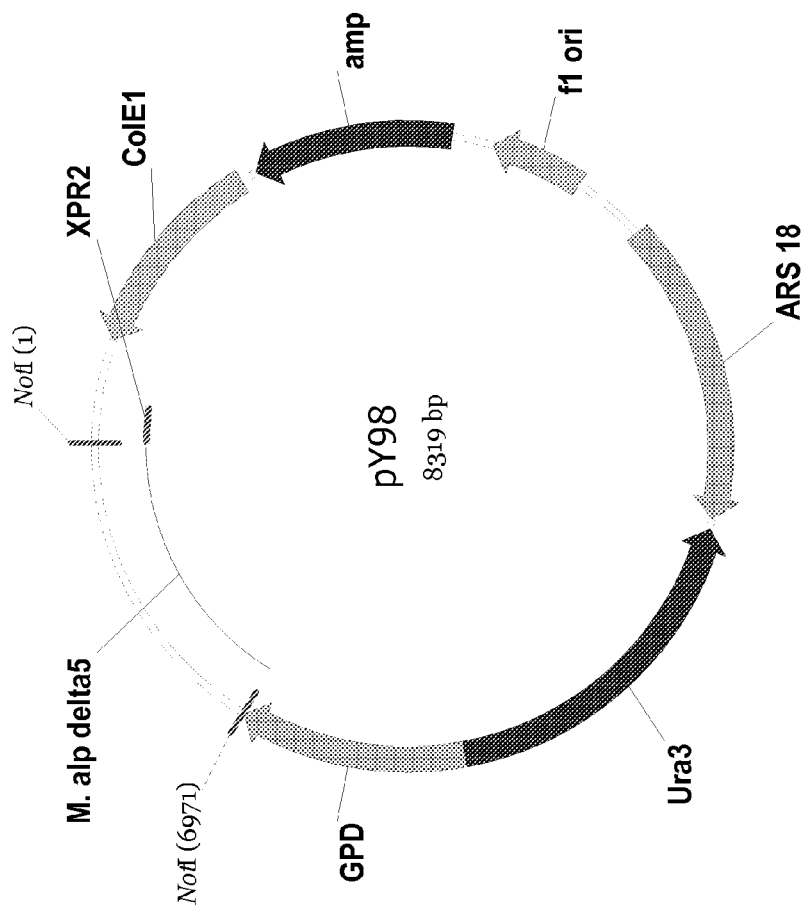

FIG. 9 provides a plasmid map for pY98.

FIG. 10A provides the fatty acid profiles for *Yarrowia lipolytica* expressing pY98 (SEQ ID NO:76; comprising a *Mortierella alpina* Δ5 desaturase gene designated as "MaD5") or pDMW368 (SEQ ID NO:23; comprising the *Peridinium* sp. CCMP626 Δ5 desaturase gene designated as "RD5") and fed various substrates. FIG. 10B provides a comparison of the ω-3 and ω-6 substrate specificity of MaD5 versus RD5.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-26, 50, 51, 53-56, 63-72 and 75-76 are ORFs encoding genes or proteins (or portions thereof), or plasmids, as identified in Table 1.

TABLE 1

Summary Of Nucleic Acid And Protein SEQ ID Numbers

| Description and Abbreviation | Nucleic acid SEQ ID No. | Protein SEQ ID NO. |
|---|---|---|
| *Peridinium* sp. CCMP626 Δ5 desaturase ("RD5") | 1 (1392 bp) | 2 (463 AA) |
| Synthetic Δ5 desaturase, derived from *Peridinium* sp. CCMP626, codon-optimized for expression in *Yarrowia lipolytica* ("RD5S") | 3 (1392 bp) | 2 (463 AA) |
| *Peridinium* sp. CCMP626-fragment of pT-12-D5 | 4 (563 bp) | 5 (187 AA) |
| *Peridinium* sp. CCMP626--fragment of pT-RD5-5'C2 | 6 (693 bp) | — |
| *Peridinium* sp. CCMP626--5' sequence relative to SEQ ID NO: 4 | 7 (511 bp) | — |
| *Peridinium* sp. CCMP626--fragment of pT-RD5-5'2$^{nd}$ | 8 (358 bp) | — |
| *Peridinium* sp. CCMP626--5' sequence relative to SEQ ID NO: 6 | 9 (161 bp) | — |
| *Peridinium* sp. CCMP626--fragment of pT-RD5-3' | 10 (299 bp) | — |
| *Peridinium* sp. CCMP626-3' sequence relative to SEQ ID NO: 4 | 11 (247 bp) | — |
| *Pythium irregulare* Δ5 desaturase (GenBank Accession No. AAL13311) | — | 12 (456 AA) |
| *Phytophthora megasperma* Δ5 desaturase (GenBank Accession No. CAD53323) | — | 13 (477 AA) |
| *Phaeodactylum tricornutum* Δ5 desaturase (GenBank Accession No. AAL92562) | — | 14 (469 AA) |
| *Dictyostelium discoideum* Δ5 desaturase (GenBank Accession No. XP_640331) | — | 15 (467 AA) |
| *Euglena gracilis* Δ8 desaturase (PCT Publications No. WO 2006/012325 and No. WO 2006/012326) | — | 16 (421 AA) |
| *Pavlova lutheri* (CCMP459) Δ8 desaturase | 17 (1269 bp) | 18 (423 AA) |
| Conserved Region 1 | — | 19 (7 AA) |

TABLE 1-continued

Summary Of Nucleic Acid And Protein SEQ ID Numbers

| Description and Abbreviation | Nucleic acid SEQ ID No. | Protein SEQ ID NO. |
|---|---|---|
| Conserved Region 2 | — | 20 (7 AA) |
| *Thalassiosira pseudonanan* Δ8 sphingolipid desaturase (GenBank Accession No. AAX14502) | — | 21 (476 AA) |
| Plasmid pZUF17 | 22 (8165 bp) | — |
| Plasmid pDMW368 | 23 (8480 bp) | — |
| Plasmid pKUNF12T6E | 24 (12,649 bp) | — |
| Synthetic $C_{18/20}$ elongase gene derived from *Thraustochytrium aureum* (U.S. Pat. No. 6,677,145), codon-optimized for expression in *Yarrowia lipolytica* ("EL2S") | 25 (819 bp) | 26 (272 AA) |
| Plasmid pRD5S | 50 (4112 bp) | — |
| Plasmid pZURD5S | 51 (8480 bp) | — |
| *Rhizopus stolonifer* Δ6 fatty acid desaturase (NCBI Accession No. AAX22052) | — | 53 (459 AA) |
| *Pavlova lutheri* Δ8 desaturase--portion of cDNA insert from clone eps1c.pk002.f22 (5' end of cDNA insert) | 54 (695 bp) | — |
| *Pavlova lutheri* Δ8 desaturase--fully sequenced EST eps1c.pk002.f22: fis (full insert sequence) | 55 (1106 bp) | — |
| *Pavlova lutheri* Δ8 desaturase-translation of nucleotides 1-864 of fully sequenced EST eps1c.pk002.f22: fis (full insert sequence; SEQ ID NO: 55) | — | 56 (287 AA) |
| *Pavlova lutheri* Δ8 desaturase--full 5' end sequence from genome walking | 63 (1294 bp) | — |
| *Pavlova lutheri* Δ8 desaturase-assembled sequence | 64 (1927 bp) | — |
| *Rhizopus stolonifer* Δ6 fatty acid desaturase (NCBI Accession No. ABB96724) | — | 65 (459 AA) |
| *Pavlova salina* Δ8 desaturase | — | 66 (427 AA) |
| *Mortierella alpina* Δ5 desaturase | 67 (1338 bp) | 68 (446 AA) |
| Plasmid pY5-22 | 69 (6473 bp) | — |
| Plasmid pY5-22GPD | 70 (6970 bp) | — |
| *Yarrowia lipolytica* glyceraldehyde-3-phosphate dehydrogenase promoter (GPD) | 71 (968 bp) | — |
| Plasmid pYZDE2-S | 72 (8630 bp) | — |
| Plasmid pKR136 | 75 (6339 bp) | — |
| Plasmid pY98 | 76 (8319 bp) | — |

SEQ ID NOs:27-29 correspond to AP primer, Smart IV oligonucleotide primer and CDSIII 5' primer, respectively, used for *Peridinium* sp. CCMP626 cDNA synthesis.

SEQ ID NOs:30-33 correspond to degenerate oligonucleotide primers 5-1A, 5-1B, 5-1C and 5-1D, respectively, that encode Conserved Region 1.

SEQ ID NOs:34-37 correspond to degenerate oligonucleotide primers 5-4AR, 5-4BR, 5-4CR and 5-4DR, respectively, that encode Conserved Region 2.

SEQ ID NOs:38-42 correspond to primers ODMW520, ODMW521, DNR CDS 5', ODMW541 and ODMW542, respectively, used for 5' RACE.

SEQ ID NOs:43-45 correspond to primers ODMW523, AUAP and ODMW524, respectively, used for 3' RACE.

SEQ ID NOs:46-49 correspond to primers YL807, YL810, YL808 and YL809, respectively, used for amplification of the full length cDNA of RD5.

SEQ ID NO:52 corresponds to primer T7, used for sequencing the *Pavlova lutheri* (CCMP459) cDNA library.

SEQ ID NOs:57 and 58 correspond to primers SeqE and SeqW, respectively, used for sequencing *Pavlova lutheri* (CCMP459) clones.

SEQ ID NOs:59 and 60 correspond to the universal primer AP1 and primer GSP PvDES, respectively, used for amplification of genomic *Pavlova lutheri* (CCMP459) DNA.

SEQ ID NOs:61 and 62 correspond to primers M13-28Rev and PavDES seq, respectively, used for sequencing *Pavlova lutheri* (CCMP459) genomic inserts.

SEQ ID NOs:73 and 74 are primers GPDsense and GPDantisense, respectively, used for amplifying the GPD promoter.

DETAILED DESCRIPTION OF THE INVENTION

All patents, patent applications, and publications cited herein are incorporated by reference in their entirety. This specifically includes the following commonly owned, co-pending applications: U.S. Pat. Nos. 7,125,672, 7,189,559, 7,192,762, 7,198,937, 7,202,356, U.S. patent application Ser. No. 10/840,579 and Ser. No. 10/840,325 (filed May 6, 2004), now U.S. Pat. Nos. 7,238,482 and 7,214,491,U.S. patent application Ser. No. 10/869,630 (filed Jun. 16, 2004) now U.S. Pat. No. 7,259,255, U.S. patent application Ser. No. 10/882,760 (filed Jul. 1, 2004) now U.S. Pat. No. 7,267,976, U.S. patent application Ser. No. 10/985,254 and Ser. No. 10/985,691 (filed Nov. 10, 2004), wherein Ser. No. 10/985,691 is now U.S. Pat. No. 7,504,259, U.S. patent application Ser. No. 11/024,544 (filed Dec. 29, 2004) now U.S. Pat. No. 7,273,746, U.S. patent application Ser. No. 11/166,993 (filed Jun. 24, 2005) now U.S. Pat. No. 7,256,033, U.S. patent application Ser. No. 11/183,664 (filed Jul. 18, 2005) U.S. Pat. No. 7,459,546, U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005) now U.S. Pat. No. 7,465,564, U.S. patent application Ser. No. 11/225,354 (filed Sep. 13, 2005) now U.S. Pat. No. 7,264,949, U.S. patent application Ser. No. 11/253,882 (filed Oct. 19, 2005) now U.S. Pat. No. 7,470,532, U.S. patent application Ser. No. 11/264,784 and Ser. No. 11/264,737 (filed Nov. 1, 2005) now U.S. Pat. Nos. 7,588,931 and 7,550,286, U.S. patent application Ser. No. 11/265,761 (filed Nov. 2, 2005), U.S. Patent Application No. 60/795,810 (filed Apr. 28, 2006), U.S. Patent Application No. 60/793,575 (filed Apr. 20, 2006), U.S. Patent Application No. 60/796,637 (filed May 2, 2006), U.S. Patent Applications No. 60/801,172 and No. 60/801,119 (filed May 17, 2006), U.S. Patent Application No. 60/853,563 (filed Oct. 23, 2006), U.S. Patent Application No. 60/855,177 (filed Oct. 30, 2006), U.S. patent application Ser. No. 11/601,563 and Ser. No. 11/601,564 (filed Nov. 16, 2006), U.S. patent application Ser. No. 11/635,258 (filed Dec. 7, 2006), U.S. patent application Ser. No. 11/613,420 (filed Dec. 20, 2006), U.S. Patent Application No. 60/909,790 (filed Apr. 3, 2007), U.S. Patent Application No. 60/910,831 (filed Apr. 10, 2007) U.S. Patent Application No. 60/915,733, (filed May 3, 2007).

In accordance with the subject invention, Applicants identify a novel *Peridinium* sp. CCMP626 Δ5 desaturase enzyme and gene encoding the same that may be used for the manipulation of biochemical pathways for the production of healthful PUFAs. Thus, the subject invention finds many applications.

PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "invention" or "present invention" as used herein is not meant to be limiting to any one specific embodiment of the invention but applies generally to any and all embodiments of the invention as described in the claims and specification.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in U.S. Patent Publication No. 2005/0136519.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the specification and each compounds' chemical name.

TABLE 2

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9, 12-octadecadienoic | 18:2 ω-6 |
| γ-Linoleic | GLA | cis-6, 9, 12-octadecatrienoic | 18:3 ω-6 |
| Eicosadienoic | EDA | cis-11, 14-eicosadienoic | 20:2 ω-6 |
| Dihomo-γ-Linoleic | DGLA | cis-8, 11, 14-eicosatrienoic | 20:3 ω-6 |
| Arachidonic | ARA | cis-5, 8, 11, 14-eicosatetraenoic | 20:4 ω-6 |
| α-Linolenic | ALA | cis-9, 12, 15-octadecatrienoic | 18:3 ω-3 |
| Stearidonic | STA | cis-6, 9, 12, 15-octadecatetraenoic | 18:4 ω-3 |
| Eicosatrienoic | ETrA or ERA | cis-11, 14, 17-eicosatrienoic | 20:3 ω-3 |
| Sciadonic | SCI | cis-5, 11, 14-eicosatrienoic | 20:3b ω-6 |
| Juniperonic | JUP | cis-5, 11, 14, 17-eicosatetraenoic | 20:4b ω-3 |
| Eicosatetraenoic | ETA | cis-8, 11, 14, 17-eicosatetraenoic | 20:4 ω-3 |
| Eicosapentaenoic | EPA | cis-5, 8, 11, 14, 17-eicosapentaenoic | 20:5 ω-3 |
| Docosapentaenoic | DPA | cis-7, 10, 13, 16, 19-docosapentaenoic | 22:5 ω3 |
| Docosahexaenoic | DHA | cis-4, 7, 10, 13, 16, 19-docosahexaenoic | 22:6 ω-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO 2006/052870). Briefly, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a Δ9 elongase, a $C_{14/16}$ elongase, a $C_{16/18}$ elongase, a $C_{18/20}$ elongase and/or a $C_{20/22}$ elongase.

Figure 1:
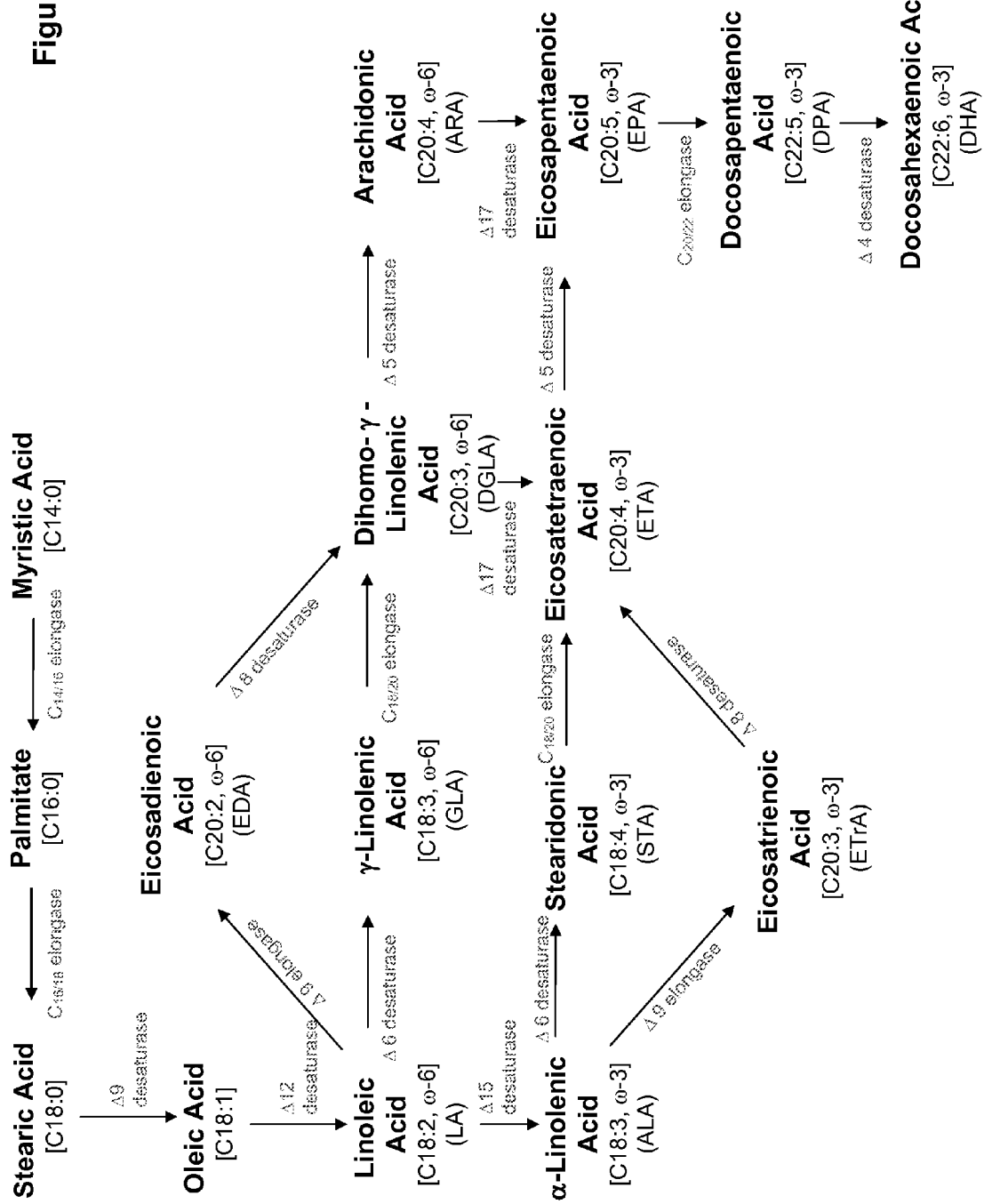
FIG. 1 illustrates the ω-3/ω-6 fatty acid biosynthetic pathway.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "Δ6 desaturase/Δ6 elongase pathway" will refer to a PUFA biosynthetic pathway that minimally includes at least one Δ6 desaturase and at least one $C_{18/20}$ elongase, thereby enabling biosynthesis of DGLA and/or ETA from LA and ALA, respectively, with GLA and/or STA as intermediate fatty acids. With expression of other desaturases and elongases, ARA, EPA, DPA and DHA may also be synthesized.

The term "Δ9 elongase/Δ8 desaturase pathway" will refer to a PUFA biosynthetic pathway that minimally includes at least one Δ9 elongase and at least one Δ8 desaturase, thereby enabling biosynthesis of DGLA and/or ETA from LA and ALA, respectively, with EDA and/or ETrA as intermediate fatty acids. With expression of other desaturases and elongases, ARA, EPA, DPA and DHA may also be synthesized.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the Δ9 elongase/Δ8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the Δ9 elongase/Δ8 desaturase pathway, sciadonic acid (SCI) and juniperonic acid (JUP) also can be produced by the action of a Δ5 desaturase on either EDA or ETrA, respectively. They are considered to be "by-product fatty acids" since neither can be further converted to EPA by the action of other metabolic pathway enzymes.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are Δ5 desaturases that catalyze the conversion of DGLA to ARA and/or ETA to EPA. Other desaturases include: 1.) Δ17 desaturases that desaturate a fatty acid between the $17^{th}$ and $18^{th}$ carbon atom numbered from the carboxyl-terminal end of the molecule and which, for example, catalyze the conversion of ARA to EPA and/or DGLA to ETA; 2.) Δ6 desaturases that catalyze the conversion of LA to GLA and/or ALA to STA; 3.) Δ12 desaturases that catalyze the conversion of oleic acid to LA; 4.) Δ15 desaturases that catalyze the conversion of LA to ALA and/or GLA to STA; 5.) Δ4 desaturases that catalyze the conversion of DPA to DHA; 6.) Δ8 desaturases that catalyze the conversion of EDA to DGLA and/or ETrA to ETA; and, 7.) Δ9 desaturases that catalyze the conversion of palmitate to palmitoleic acid (16:1) and/or stearate to oleic acid. In the art, Δ15 and Δ17 desaturases are also occasionally referred to as "omega-3 desaturases", "w-3 desaturases", and/or "ω-3 desaturases", based on their ability to convert ω-6 fatty acids into their ω-3 counterparts (e.g., conversion of LA into ALA and ARA into EPA, respectively). In some embodiments, it is most desirable to empirically determine the specificity of a particular fatty acid desaturase by transforming a suitable host with the gene for the fatty acid desaturase and determining its effect on the fatty acid profile of the host.

For the purposes herein, the term "RD5" refers to a Δ5 desaturase enzyme (SEQ ID NO:2) isolated from Peridinium sp. CCMP626, encoded by SEQ ID NO:1 herein. Similarly, the term "RD5S" refers to a synthetic Δ5 desaturase derived from Peridinium sp. CCMP626 that is codon-optimized for expression in Yarrowia lipolytica (i.e., SEQ ID NOs:3 and 2).

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in U.S. Patent Publication No. 2005/0132442 and PCT Publication No. WO 2005/047480. Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase (also known as a Δ6 elongase as the terms can be used interchangeably) will utilize a $C_{18}$ substrate (e.g., GLA, STA) and a $C_{20/22}$ elongase will utilize a $C_{20}$ substrate (e.g., EPA). In like manner, a Δ9 elongase is able to catalyze the conversion of LA and ALA to EDA and ETrA, respectively. It is important to note that some elongases have broad specificity and thus a single enzyme may be capable of catalyzing several elongase reactions (e.g., thereby acting as both a $C_{16/18}$ elongase and a $C_{18/20}$ elongase).

The term "oleaginous" refers to those organisms that tend to store their energy source in the form of lipid (Weete, In: Fungal Lipid Biochemistry, $2^{nd}$ Ed., Plenum, 1980). The term "oleaginous yeast" refers to those microorganisms classified as yeasts that can make oil. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

As used herein, the terms "isolated nucleic acid fragment" or "isolated nucleic acid molecule" will be used interchangeably and refer to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular algal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the invention herein also includes isolated nucleic acid fragments that are complementary to the complete sequences as reported in the accompanying Sequence Listing, as well as those substantially similar nucleic acid sequences.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the present invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant algal polypeptide as set forth in SEQ ID NO:2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' "non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; PCT Publication No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Mature" protein refers to a post-translationally processed polypeptide, i.e., one from which any pre- or propeptides present in the primary translation product have been removed. "Precursor" protein refers to the primary product of translation of mRNA, i.e., with pre- and propeptides still present. Pre- and propeptides may be (but are not limited to) intracellular localization signals.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and, 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS*, 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS*, 5:151-153 (1989); Higgins, D. G. et al., *Comput. Appl. Biosci.*, 8:189-191(1992)) and found in the MegAlign™ v6.1 program of the LASERGENE bioinformatics computing suite (DNASTAR Inc.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Although preferred ranges are described above, any integer amino acid identity from 67% to 100% may be useful in describing the present invention, such as 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. With regard to the BLASTP algorithm used herein default parameters will include the Robinson and Robinson amino acid frequencies (Robinson A. B., Robinson L. R., *Proc. Natl Acad. Sci. U.S.A.*, 88:8880-8884 (1991)), the BLOSUM62 scoring matrix and the gap cost $\Delta(g)=11+g$.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

An Overview Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and, 4.) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to ω-3/ω-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific ω-3/ω-6 fatty acid.

Specifically, all pathways require the initial conversion of oleic acid to LA, the first of the ω-6 fatty acids, by a $\Delta 12$ desaturase. Then, using the "$\Delta 6$ desaturase/$\Delta 6$ elongase pathway", ω-6 fatty acids are formed as follows: (1) LA is converted to GLA by a $\Delta 6$ desaturase; (2) GLA is converted to DGLA by a $C_{18/20}$ elongase; and, (3) DGLA is converted to ARA by a $\Delta 5$ desaturase. Alternatively, the "$\Delta 6$ desaturase/$\Delta 6$ elongase pathway" can be utilized for formation of ω-3 fatty acids as follows: (1) LA is converted to ALA, the first of the ω-3 fatty acids, by a $\Delta 15$ desaturase; (2) ALA is converted to STA by a $\Delta 6$ desaturase; (3) STA is converted to ETA by a $C_{18/20}$ elongase; (4) ETA is converted to EPA by a $\Delta 5$ desaturase; (5) EPA is converted to DPA by a $C_{20/22}$ elongase; and, (6) DPA is converted to DHA by a $\Delta 4$ desaturase. Optionally, ω-6 fatty acids may be converted to ω-3 fatty acids; for example, ETA and EPA are produced from DGLA and ARA, respectively, by $\Delta 17$ desaturase activity.

Alternate pathways for the biosynthesis of ω-3/ω-6 fatty acids utilize a $\Delta 9$ elongase and $\Delta 8$ desaturase. More specifically, LA and ALA may be converted to EDA and ETrA, respectively, by a $\Delta 9$ elongase; then, a $\Delta 8$ desaturase converts EDA to DGLA and/or ETrA to ETA.

It is contemplated that the particular functionalities required to be expressed in a specific host organism for production of ω-3/ω-6 fatty acids will depend on the host cell (and its native PUFA profile and/or desaturase/elongase profile), the availability of substrate, and the desired end product(s). One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or, 4.) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired ω-3/ω-6 fatty acid, as well as various upstream intermediary PUFAs. Thus, each enzyme's conversion efficiency is also a variable to consider, when optimizing biosynthesis of a desired fatty acid.

With each of the considerations above in mind, candidate genes having the appropriate desaturase and elongase activities (e.g., $\Delta 6$ desaturases, $C_{18/20}$ elongases, $\Delta 5$ desaturases, $\Delta 17$ desaturases, $\Delta 15$ desaturases, $\Delta 9$ desaturases, $\Delta 12$ desaturases, $C_{14/16}$ elongases, $C_{16/18}$ elongases, $\Delta 9$ elongases, $\Delta 8$ desaturases, $\Delta 4$ desaturases and $C_{20/22}$ elongases) can be identified according to publicly available literature (e.g., GenBank), the patent literature, and experimental analysis of organisms having the ability to produce PUFAs.

These genes will be suitable for introduction into a specific host organism, to enable or enhance the organism's synthesis of PUFAs.

Sequence Identification of a Novel *Peridinium* sp. CCMP626 Δ5 Desaturase

In the present invention, a nucleotide sequence (SEQ ID NO:1) has been isolated from *Peridinium* sp. CCMP626 encoding a Δ5 desaturase (SEQ ID NO:2), designated herein as "RD5".

Comparison of the RD5 nucleotide base and deduced amino acid sequences to public databases reveals that the most similar known sequences are about 67% identical to the amino acid sequence of RD5 reported herein over a length of 463 amino acids using a BLASTP search algorithm. More preferred amino acid fragments are at least about 70%-80% identical to the sequences herein, where those sequences that are at least about 80%-90% identical are particularly suitable and those sequences that are at least about 90%-95% identical are most preferred. Similarly, preferred RD5 encoding nucleic acid sequences corresponding to the instant ORF are those encoding active proteins and which are at least about 70%-80% identical to the nucleic acid sequences of RD5 reported herein, where those sequences that are at least about 80%-90% identical are particularly suitable and those sequences that are at least about 90%-95% identical are most preferred.

In alternate embodiments, the instant RD5 desaturase sequence can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species.

In one preferred embodiment of the invention herein, RD5 was codon-optimized for expression in *Yarrowia lipolytica*. This was possible by first determining the *Y. lipolytica* codon usage profile (see PCT Publication No. WO 04/101757 and U.S. Pat. No. 7,125,672) and identifying those codons that were preferred. Then, for further optimization of gene expression in *Y. lipolytica*, the consensus sequence around the 'ATG' initiation codon was determined. This optimization resulted in modification of 247 bp of the 1392 bp coding region (17.7%) and optimization of 229 codons of the total 463 codons (49.4%). None of the modifications in the codon-optimized gene ("RD5S"; SEQ ID NO:3) changed the amino acid sequence of the encoded protein (SEQ ID NO:2). As described in Example 11, the codon-optimized gene was 8.9% more efficient desaturating DGLA to ARA than the wildtype gene, when expressed in *Y. lipolytica*.

One skilled in the art would be able to use the teachings herein to create various other codon-optimized Δ5 desaturase proteins suitable for optimal expression in alternate hosts (i.e., other than *Yarrowia lipolytica*), based on the wildtype RD5 sequence. Accordingly, the instant invention relates to any codon-optimized Δ5 desaturase protein that is derived from the wildtype RD5 (i.e., encoded by SEQ ID NO:2). This includes, but is not limited to, the nucleotide sequence set forth in SEQ ID NO:3, which encodes a synthetic Δ5 desaturase protein (i.e., RD5S) that was codon-optimized for expression in *Yarrowia lipolytica*.

Identification and Isolation of Homologs

Any of the instant desaturase sequences (i.e., RD5, RD5S) or portions thereof may be used to search for Δ5 desaturase homologs in the same or other bacterial, algal, fungal, or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of Δ5 homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ5 desaturase nucleic acid fragments described herein (or any homologs identified thereof) may be used to isolate genes encoding homologous proteins from the same or other bacterial, algal, fungal, or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Natl. Acad. Sci. U.S.A.*, 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the Δ5 desaturases described herein could be isolated directly by using all or a portion of the instant nucleic acid fragments as DNA hybridization probes to screen libraries from e.g., any desired yeast or fungus using methodology well known to those skilled in the art (wherein those organisms producing ARA [or derivatives thereof] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Natl Acad. Sci. U.S.A.*, 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *Proc. Natl Acad. Sci. U.S.A.*, 86:5673 (1989); Loh et al., *Science*, 243:217 (1989)).

In other embodiments, any of the Δ5 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Alternatively, improved fatty acids may be synthesized by domain swapping, wherein a functional domain from any of the Δ5 desaturase nucleic acid fragments described herein are exchanged with a functional domain in an alternate desaturase gene to thereby result in a novel protein.

Methods for Production of Various ω-3 and/or ω-6 Fatty Acids

It is expected that introduction of chimeric genes encoding the Δ5 desaturases described herein (i.e., RD5, RD5S or other mutant enzymes, codon-optimized enzymes or homologs thereof), under the control of the appropriate promoters will result in increased production of ARA and/or EPA in the transformed host organism, respectively. As such, the present invention encompasses a method for the direct production of PUFAs comprising exposing a fatty acid substrate (i.e., DGLA or ETA) to the desaturase enzymes described herein (e.g., RD5, RD5S), such that the substrate is converted to the desired fatty acid product (i.e., ARA or EPA, respectively).

More specifically, it is an object of the present invention to provide a method for the production of ARA in a host cell (e.g., oleaginous yeast), wherein the host cell comprises:
(i) an isolated nucleotide molecule encoding a Δ5 desaturase polypeptide having at least 95% identity when compared to a polypeptide having an amino acid sequence as set forth in SEQ ID NO:2, based on BLASTP algorithms; and,
(ii) a source of dihomo-γ-linoleic acid;

wherein the host cell is grown under conditions such that the Δ5 desaturase is expressed and the DGLA is converted to ARA, and wherein the ARA is optionally recovered.

The person of skill in the art will recognize that the broad substrate range of the Δ5 desaturase may additionally allow for the use of the enzyme for the conversion of ETA to EPA. Accordingly the invention provides a method for the production of EPA, wherein the host cell comprises:
(i) an isolated nucleotide molecule encoding a Δ5 desaturase polypeptide having at least 95% identity when compared to a polypeptide having an amino acid sequence as set forth in SEQ ID NO:2, based on BLASTP algorithms; and,
(ii) a source of ETA;

wherein the host cell is grown under conditions such that the Δ5 desaturase is expressed and the ETA is converted to EPA, and wherein the EPA is optionally recovered.

Alternatively, each Δ5 desaturase gene and its corresponding enzyme product described herein can be used indirectly for the production of ω-3 fatty acids (see U.S. Patent Publication No. 2005/0136519). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ5 desaturases described herein (e.g., RD5, RD5S or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases, $C_{20/22}$ elongases) to result in higher levels of production of longer-chain ω-3 fatty acids (e.g., EPA, DPA and DHA). The particular genes included within a particular expression cassette will depend on the host cell (and its PUFA profile and/or desaturase/elongase profile), the availability of substrate and the desired end product(s).

In alternative embodiments, it may be useful to disrupt a host organism's native Δ5 desaturase, based on the complete sequences described herein, the complement of those complete sequences, substantial portions of those sequences, codon-optimized desaturases derived therefrom and those sequences that are substantially homologous thereto.

Expression Systems, Cassettes and Vectors

The genes and gene products of the instant sequences described herein may be expressed in heterologous host cells. Expression in recombinant hosts may be useful for the production of various PUFA pathway intermediates, or for the modulation of PUFA pathways already existing in the host for the synthesis of new products heretofore not possible using the host.

Expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate host cells via transformation to provide high-level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed host cell, although it is to be understood that such control regions need not be derived from the genes native to the specific species chosen as a production host.

Initiation control regions or promoters which are useful to drive expression of the instant Δ5 desaturase ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see U.S. patent application Ser. No. 11/265,761, corresponding to PCT Publication No. WO 2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation and correct folding of the protein in the host organism; 5.) the intrinsic stability of the mRNA and protein of the cloned gene within the host cell; and, 6.) the codon usage within the cloned gene, such that its frequency approaches the frequency of preferred codon usage of the host cell. Each of these types of modifications are encompassed in the present invention, as means to further optimize expression of the Δ5 desaturases described herein.

Transformation of Host Cells

Once the DNA encoding a polypeptide suitable for expression in an appropriate host cell has been obtained (e.g., a chimeric gene comprising a promoter, ORF and terminator), it is placed in a plasmid vector capable of autonomous replication in the host cell, or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell.

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by various selection techniques, as described in U.S. Patent Publications No. 2005/0136519 and No. 2005/0014270, corresponding to PCT Publications No. WO 2004/101757 and No. WO 2005/003310, respectively.

Following transformation, substrates suitable for the instant Δ5 desaturases (and, optionally other PUFA enzymes that are co-expressed within the host cell) may be produced by the host either naturally or transgenically, or they may be provided exogenously.

Metabolic Engineering of ω-3 and/or ω-6 Fatty Acid Biosynthesis

Knowledge of the sequences of the present Δ5 desaturases will be useful for manipulating ω-3 and/or ω-6 fatty acid biosynthesis in various host cells. This may require metabolic engineering directly within the PUFA biosynthetic pathway or additional manipulation of pathways that contribute carbon to the PUFA biosynthetic pathway. Methods useful for up-regulating desirable biochemical pathways and down-regulating undesirable biochemical pathways are well known to those skilled in the art. For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication No. WO 2006/055322 [U.S. Patent Publication No. 2006-0094092-A1], PCT Publication No. WO 2006/052870 [U.S. Patent Publication No. 2006-0115881-A1] and PCT Publication No. WO 2006/052871 [U.S. Patent Publication No. 2006-0110806-A1], respectively, as are desirable manipulations in the TAG biosynthetic pathway and the TAG degradation pathway (and associated techniques thereof).

Preferred Hosts for Recombinant Expression of Δ5 Desaturases

Host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. Based on the needs of the Applicants' Assignee, the genes described in the instant invention were initially isolated for expression in an oleaginous yeast (and in particular *Yarrowia lipolytica*); however, it is contemplated that because transcription, translation and the protein biosynthetic apparatus are highly conserved, any bacteria, yeast, algae, and/or fungus will be a suitable host for expression of the present nucleic acid fragments.

Preferred hosts are oleaginous organisms, such as oleaginous yeast. These oleaginous organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., *Bioresour. Technol.*, 82(1):43-9 (2002)).

Specific teachings applicable for transformation of oleaginous yeasts (i.e., *Yarrowia lipolytica*) include U.S. Pat. Nos. 4,880,741, 5,071,764 (incorporated herein by reference) and Chen, D. C. et al. (*Appl. Microbiol. Biotechnol.*, 48(2):232-235 (1997)). Specific teachings applicable for engineering ARA, EPA and DHA in *Y. lipolytica* are provided in U.S. patent application Ser. No. 11/264,784, Ser. No. 11/265,761 and Ser. No. 11/264,737, respectively and incorporated herein by reference. Detailed means for the synthesis and transformation of expression vectors comprising Δ5 desaturases in oleaginous yeast (i.e., *Yarrowia lipolytica*) are provided in PCT Publications No. WO 2004/101757 and No. WO 2006/052870. The preferred method of expressing genes in this yeast is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene locus (GenBank Accession No. M34929), the Aco2 gene locus (Gen Bank Accession No. AJ001300), the Pox3 gene locus (Pox3: GenBank Accession No. XP_503244; or, Aco3: GenBank Accession No. AJ001301), the Δ12 desaturase gene locus (PCT Publication No. WO 2004/104167), the Lip1 gene locus (GenBank Accession No. Z50020) and/or the Lip2 gene locus (GenBank Accession No. AJ012632)].

Preferred selection methods for use in *Yarrowia lipolytica* are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate; "5-FOA") is used for selection of yeast Ura⁻ mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997).

Other preferred microbial hosts include oleaginous bacteria, algae, and other fungi; and, within this broad group of microbial hosts, of particular interest are microorganisms that synthesize ω-3/ω-6 fatty acids. Thus, for example, transformation of *Mortierella alpina* (which is commercially used for production of ARA) with any of the present Δ5 desaturase genes under the control of inducible or regulated promoters could yield a transformant organism capable of synthesizing increased quantities of ARA. The method of transformation of *M. alpina* is described by Mackenzie et al. (*Appl. Environ. Microbiol.*, 66:4655 (2000)). Similarly, methods for transformation of Thraustochytriales microorganisms are disclosed in U.S. Pat. No. 7,001,772.

No matter what particular host is selected for expression of the Δ5 desaturases described herein, multiple transformants must be screened in order to obtain a strain displaying the desired expression level and pattern. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western and/or Elisa analyses of protein expression, phenotypic analysis or GC analysis of the PUFA products.

Fermentation Processes for Omega Fatty Acid Production

The transformed host cell is grown under conditions that optimize expression of chimeric desaturase genes and produce the greatest and most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in PCT Publication No. WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in *Yarrowia lipolytica*. This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(5/6):463-491 (1992)). A brief review of downstream processing is also available by A. Singh and O. Ward (*Adv. Appl. Microbiol.*, 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details.

Oils for Use in Foodstuffs, Health Food Products, Pharmaceuticals and Animal Feeds The market place currently supports a large variety of food and feed products, incorporating ω-3 and/or ω-6 fatty acids (particularly ARA, EPA and DHA). It is contemplated that the oils of the invention comprising long-chain PUFAs will function in food and feed products to impart the health benefits of current formulations. More specifically, oils of the invention containing ω-3 and/or ω-6 fatty acids will be suitable for use in a variety of food and feed products including, but not limited to food analogs, meat products, cereal products, baked foods, snack foods and dairy products (see U.S. Patent Publication No. 2006/0094092 for details).

Additionally the present oils may be used in formulations to impart health benefits in medical foods including medical nutritionals, dietary supplements, infant formula as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* (XL1-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Unless otherwise indicated herein comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strain ATCC #20362 was purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Y. lipolytica* was performed according to the method of Chen, D. C. et al. (*Appl. Microbiol. Biotechnol.*, 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 µg sheared salmon sperm DNA. Then, approximately 500 ng of linearized plasmid DNA was incubated in 100 µl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters were prepared by transesterification of the lipid extract with sodium methoxide (Roughan, G., and Nishida I., *Arch Biochem Biophys.*, 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

*Peridinium* sp. CCMP626 Lipid Profile and RNA Isolation

Figure 2:
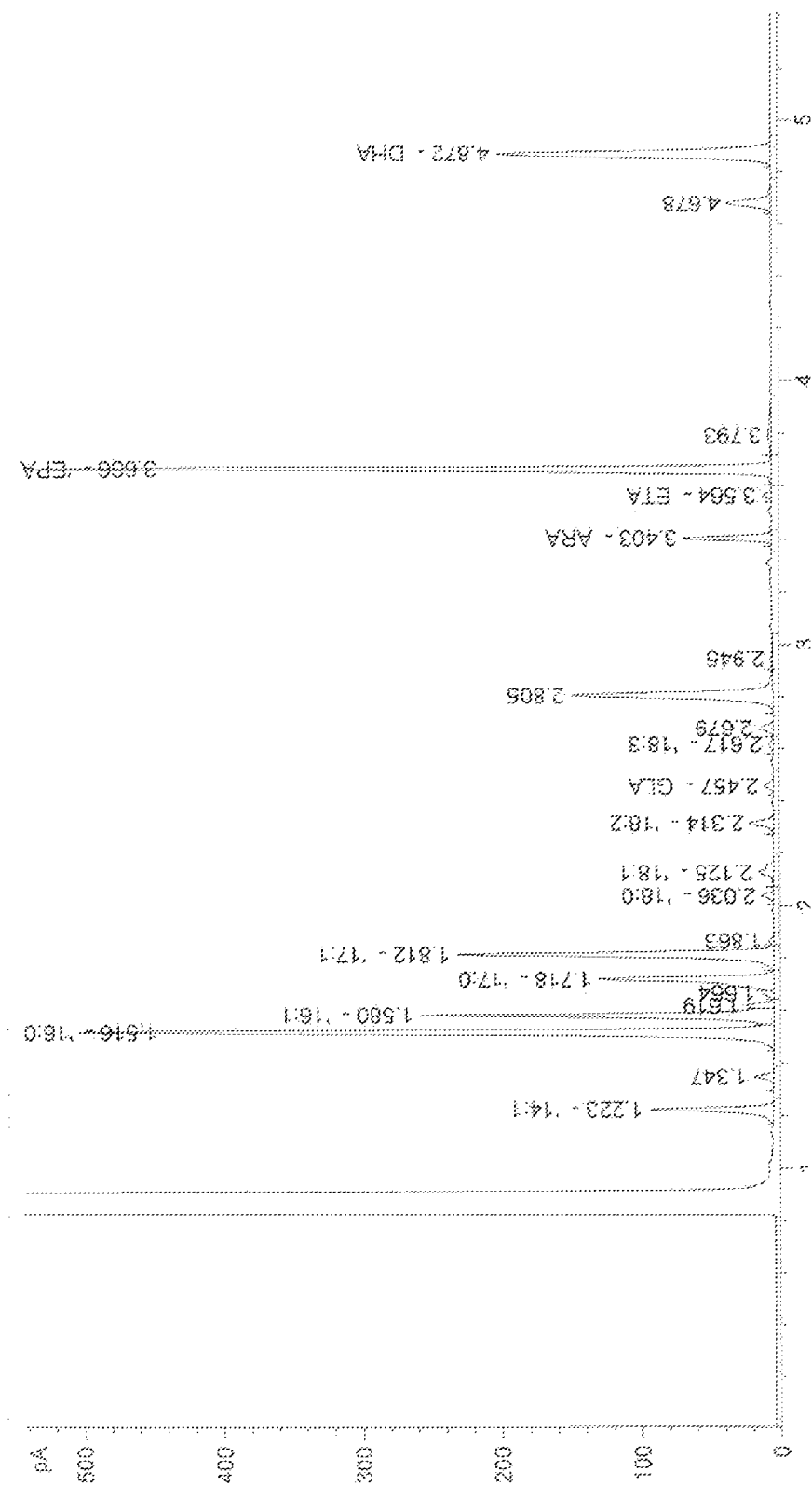
FIG. 2 shows a chromatogram of the lipid profile of a *Peridinium* sp. CCMP626 cell extract as described in Example 1.

*Peridinium* sp. CCMP626 (red algae) was purchased from The Provasoli-Guillard National Center for Culture of Marine Phytoplankton (Boothbay Harbor, Me.). About 200 mg cells were dried for 5 min under vacuum, resuspended in 100 µL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 µL injected from hexane layer) were separated and quantified using a Hewlett-Packard 6890 Gas Chromatograph fitted with an Omegawax 320 fused silica capillary column (Catalog #24152, Supelco Inc., Bellefonte, Pa.). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Catalog #U-99-A, Nu-Chek Prep, Inc., Elysian, Minn.) and the resulting chromatogram is shown in FIG. 2.

The GC profile demonstrated that *Peridinium* sp. CCMP626 cells produced large amounts of both ARA and EPA, thus suggesting the presence of a Δ5 desaturase with high efficiency. Since only a trace amount of GLA was detected, it was hypothesized that *Peridinium* sp. CCMP626 utilizes a Δ9 elongase/Δ8 desaturase pathway for PUFA production.

Total RNA was extracted from CCMP626 cells. Specifically, cells from 1 L of culture were collected by centrifugation, quick frozen in liquid $N_2$ and stored at −80° C. The cell pellet was resuspended in 1 mL of Trizol reagent (Invitrogen, Carlsbad, Calif.), mixed with 0.6 mL of glass beads (0.5 mm), and the mixture was homogenized at the highest setting on a Biospec Mini Beadbeater (Bartlesville, Okla.) for 3 min. Total RNA was then isolated, according to Invitrogen's protocol for Trizol. In this way, total RNA (34 μg) was obtained from 1 L culture. The total RNA sample was used for preparation of cDNA.

Example 2

Peridinium sp. CCMP626 cDNA Synthesis cDNA was synthesized directly from the Peridinium sp. CCMP626 total RNA as follows. Specifically, the total RNA was primered with adapter primer AP (SEQ ID NO:27) from Invitrogen's 3'-RACE kit (Carlsbad, Calif.), in the presence of the Smart IV oligonucleotide (SEQ ID NO:28) from the BD-Clontech Creator™ Smart™ cDNA library kit (Mississauga, ON, Canada). The reverse transcription was done with Superscript II reverse transcriptase from the 3'-RACE kit according to the protocol of the Creator™ Smart™ cDNA library kit.

The $1^{st}$ strand cDNA synthesis mixture was used as template for PCR amplification, using primer AP (SEQ ID NO:27) as the 3' primer and CDSIII 5' primer (SEQ ID NO:29) as the 5' primer (supplied with the BD-Clontech Creator™ Smart™ cDNA library kit). Amplification was carried out with Clontech Advantage cDNA polymerase mix at 94° C. for 30 sec, followed by 20 cycles of 94° C. for 10 sec and 68° C. for 6 min. A final extension at 68° C. for 7 min was performed.

Example 3

Isolation of a Portion of the Coding Region of the Peridinium sp. CCMP626 Δ5 Desaturase Gene The present Example describes the identification of a portion of the Peridinium sp. CCMP626 gene encoding Δ5 desaturase (designated herein as "RD5" [i.e., red algae D5] and corresponding to SEQ ID NOs:1 and 2), by use of primers derived from conserved regions of other known Δ5 and Δ8 desaturase sequences.

Various considerations were made when evaluating which desaturases might enable design of degenerate primers suitable to isolate the Peridinium sp. CCMP626 Δ5 desaturase. Specifically, the Applicants knew that only Δ5, Δ6 and Δ8 desaturase sequences comprise a conserved 'HPGG' motif at their N-terminus (wherein the 'HPGG' domain is part of the well-known cytochrome B5 domain); in contrast, Δ9 desaturases possess a 'HPGG' motif of the cytochrome B5 domain at their C-terminus, while both Δ17 and Δ12 desaturases lack the cytochrome B5 domain. Based on the GC results described in FIG. 2, it was assumed that a Δ9 elongase/Δ8 desaturase pathway operated in Peridinium sp. CCMP626; thus, among the desaturases sharing the N-terminal conserved 'HPGG' motif, only Δ5 and Δ8 desaturases were expected within the organism. Finally, although only a few Δ8 desaturase sequences are known, numerous Δ5 desaturases are publicly available. The Applicants selected those Δ5 desaturase sequences that possessed lower homology to "traditional" Δ5 desaturase genes and that also shared high homology to one another.

Based on the above, the four Δ5 desaturases and two Δ8 desaturases shown below in Table 3 were aligned, using the method of Clustal W (slow, accurate, Gonnet option; Thompson et al., Nucleic Acids Res., 22:4673-4680 (1994)) of the MegAlign™ program of DNASTAR software.

TABLE 3

Δ5 And Δ8 Desaturases Aligned To Identify Regions Of Conserved Amino Acids

| Desaturase | Organism | Reference | SEQ ID No: |
|---|---|---|---|
| Δ5 | Pythium irregulare | GenBank Accession No. AAL13311 | 12 |
| Δ5 | Phytophthora megasperma | GenBank Accession No. CAD53323 | 13 |
| Δ5 | Phaeodactylum tricornutum | GenBank Accession No. AAL92562 | 14 |
| Δ5 | Dictyostelium discoideum | GenBank Accession No. XP_640331 | 15 |
| Δ8 | Euglena gracilis | PCT Publications No. WO 2006/012325 and No. WO 2006/012326 | 16 |
| Δ8 | Pavlova lutheri | Example 12 (infra) | 18 |

Figure 3:
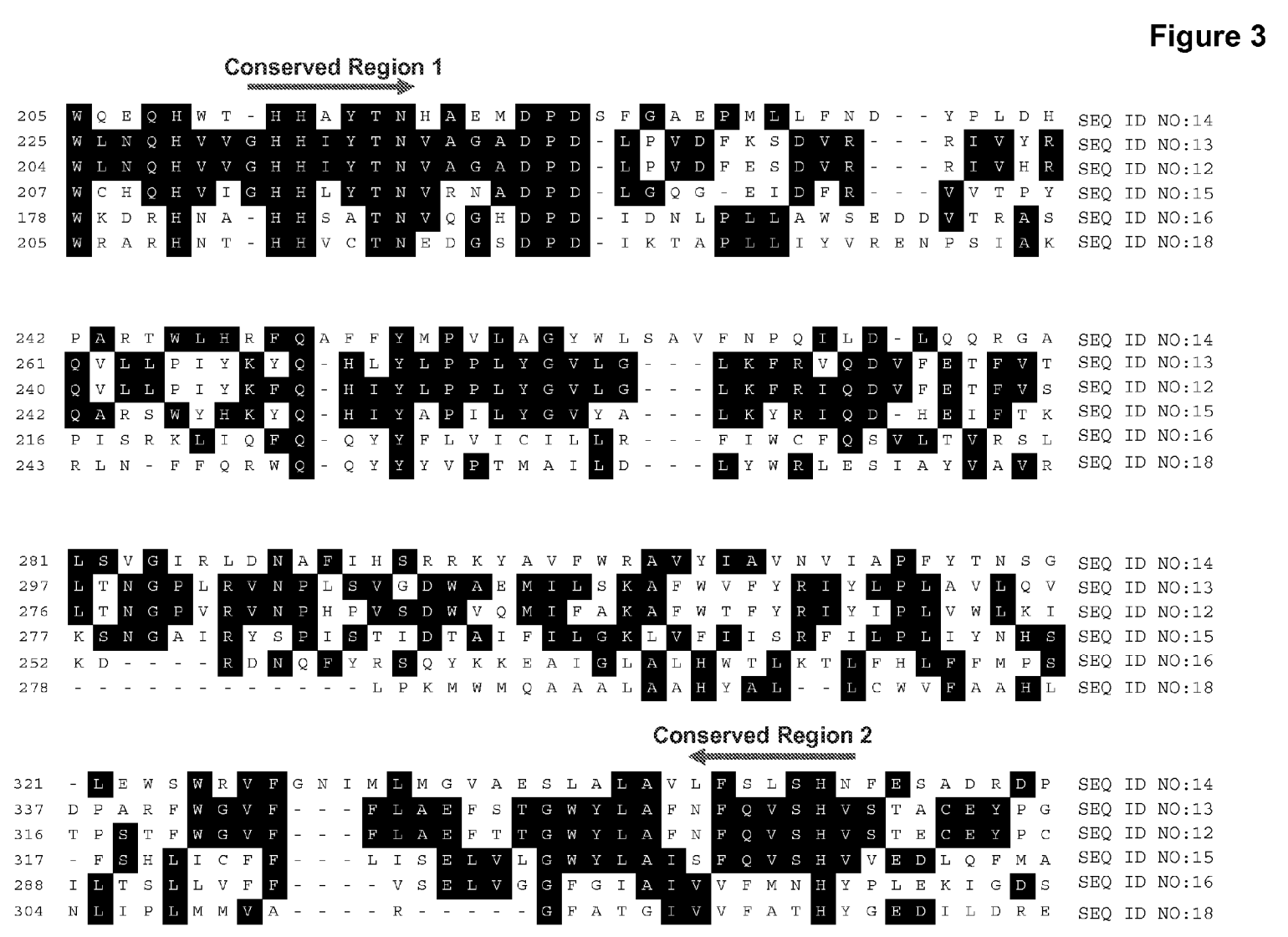

FIG. 3 shows a portion of the resulting alignment, containing several stretches of conserved amino acid sequence among the 6 different organisms. Based on this alignment, two sets of degenerate oligonucleotides were designed to amplify a portion of the coding region of the Δ5 desaturase gene from Peridinium sp. CCMP626, corresponding to the regions of FIG. 3 that are labeled as "Conserved Region 1" and "Conserved Region 2". Specifically, the conserved amino acid sequence GHH(I/V)YTN (SEQ ID NO:19) was designed to correspond to Conserved Region 1, while the conserved amino acid sequence NFQ(V/A)(S/N)HV (SEQ ID NO:20) was designed to correspond to Conserved Region 2. In order to reduce the degeneracy of the oligonucleotides, 4 sets of oligonucleotides (i.e., 5-1A, 5-1B, 5-1C and 5-1D) were designed to encode Conserved Region 1; and, 4 sets of oligonucleotides (i.e., 5-4AR, 5-4BR, 5-4CR and 5-4DR) were designed to encode the anti-sense strand of Conserved Region 2.

TABLE 4

Degenerate Oligonucleotides Used To Amplify The Δ5 Desaturase Gene From Peridinium sp. CCMP626

| Oligonucleotide Name | Sequence | SEQ ID NO |
|---|---|---|
| 5-1A | GGHCAYCAYRTBTAYACAAA | SEQ ID NO: 30 |
| 5-1B | GGHCAYCAYRTBTAYACCAA | SEQ ID NO: 31 |
| 5-1C | GGHCAYCAYRTBTAYACGAA | SEQ ID NO: 32 |
| 5-1D | GGHCAYCAYRTBTAYACTAA | SEQ ID NO: 33 |
| 5-4AR | ACRTGRYTNACYTGRAAGTT | SEQ ID NO: 34 |
| 5-4BR | ACRTGRYTNACYTGRAAATT | SEQ ID NO: 35 |
| 5-4CR | ACRTGNGANACYTGRAAGTT | SEQ ID NO: 36 |
| 5-4DR | ACRTGNGANACYTGRAAATT | SEQ ID NO: 37 |

[Note: The nucleic acid degeneracy code used for SEQ ID NOs: 30 to 37 was as follows: R = A/G; Y = C/T; B = G/T/C; and H = A/C/T.]

Based on the full-length sequences of the Δ5 sequences of FIG. 3, it was hypothesized that the Peridinium sp. CCMP626

Δ5 gene fragment amplified as described above would be about 630 bp in length (lacking about 210 amino acids at its N-terminal and 70 amino acids at its C-terminal).

A total of sixteen different PCR amplifications were conducted, as all combinations of the primers were tested (i.e., primer 5-1A was used with each of 5-4AR, 5-4BR, 5-4CR and 5-4DR, individually; similarly, primer 5-1B was used with each 5-4AR, 5-4BR, 5-4CR and 5-4DR; etc.). The PCR amplifications were carried out in a 50 μl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer, 10 ng cDNA of *Peridinium* sp. CCMP626 and 1 μl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min.

The PCR products were purified using a Qiagen PCR purification kit (Valencia, Calif.). One fragment of the approximate expected size was then further purified following gel electrophoresis in 1% (w/v) agarose and then cloned into the pGEM-T-easy vector (Promega, Madison, Wis.). The ligated DNA was used to transform cells of *E. coli* DH10B and transformants were selected on LB (1% bacto-tryptone, 0.5% bacto-yeast extract and 1% NaCl) agar containing ampicillin (100 μg/mL). Analysis of the plasmid DNA from a group of 12 transformants confirmed the presence of the insert with the expected size (plasmids were designated as "pT-12-D1", "pT-12-D2", "pT-12-D3", etc. to "pT-12-D12").

Sequence analyses showed that pT-12-D5 contained a 563 bp fragment (SEQ ID NO:4), which encoded 187 amino acids (SEQ ID NO:5) (including amino acids that corresponded to Conserved Region 1 and 2). Identity of the *Peridinium* sp. CCMP626 sequence was determined by conducting BLAST (Basic Local Alignment Search Tool; Altschul, S. F., et al., *J. Mol. Biol.*, 215:403-410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). SEQ ID NO:4 was compared for similarity to all publicly available protein sequences contained in the "nr" database, using the BLASTX algorithm (Gish, W. and States, D. J., *Nature Genetics*, 3:266-272 (1993)) provided by the NCBI.

The results of the BLASTX comparison summarizing the sequence to which SEQ ID NO:4 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance. Thus, the translated amino acid sequence of SEQ ID NO:4 (i.e., SEQ ID NO:5) had 64% identity and 78% similarity with the amino acid sequence of the Δ8-sphingolipid desaturase of *Thalassiosira pseudonana* (GenBank Accession No. AAX14502; SEQ ID NO:21), with an Expectation value of 2E-64; additionally, the partial fragment of SEQ ID NO:4 had 65% identity and 78% similarity with the Δ5 fatty acid desaturase of *Phaeodactylum tricornutum* (GenBank Accession No. AAL92562; SEQ ID NO:14), with an Expectation value of 7E-62.

Example 4

Isolation of the 5'Coding Region of the *Peridinium* sp. CCMP626 Δ5 Desaturase Gene To isolate the N-terminal portion of the putative Δ5 desaturase identified in Example 3, a modified 5' RACE technique based on RACE protocols from two different companies (i.e., Invitrogen and BD-Clontech) was utilized.

Briefly, the double-stranded cDNA of *Peridinium* sp. CCMP626 (Example 2) was used as the template in a 5' RACE experiment, comprising two separate rounds of PCR amplification. In the first round of PCR amplification, the oligonucleotide primers consisted of a gene specific oligonucleotide (i.e., ODMW520; SEQ ID NO:38) and the generic oligonucleotide CDSIII 5' primer (SEQ ID NO:29) from the BD-Clontech Creator™ Smart™ cDNA library kit. The PCR amplifications were carried out in a 50 μl total volume, comprising: 25 μl of LA Taq™ pre-mix (TaKaRa Bio Inc., Otsu, Shiga, 520-2193, Japan), 10 pmole of each primer and 1 μl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min.

The second round of PCR amplification used 1 μl of the product from the first round PCR reaction as template. Primers consisted of a gene specific oligonucleotide (i.e., ODMW521; SEQ ID NO:39) and the generic oligonucleotide DNR CDS 5' (SEQ ID NO:40), supplied with BD-Clontech's Creator™ Smart™ cDNA library kit. Amplification was conducted as described above.

The products of the second round PCR reaction were electrophoresed in 1% (w/v) agarose. Products between 400 bp and 800 bp were then purified from the gel and cloned into the pGEM-T-easy vector (Promega, Madison, Wis.). The ligated DNA was used to transform *E. coli* DH10B and transformants were selected on LB agar containing ampicillin (100 μg/mL).

Analysis of the plasmid DNA from one transformant comprising the 5' region of the putative Δ5 desaturase gene confirmed the presence of the expected plasmid, designated pT-RD5-5'C2. Sequence analyses showed that pT-RD5-5'C2 contained a fragment of 693 bp (SEQ ID NO:6), which overlapped with 182 bp from the 5' end of the 563 bp fragment of pT-12-D5 (Example 3; SEQ ID NO:4) and additionally provided 511 bp of 5' upstream sequence (SEQ ID NO:7) (FIG. 4). The sequence of pT-RD5-5'C2 also corrected the sequence corresponding to Conserved Region 1, resulting from use of a degenerate oligonucleotide for initial PCR amplification of the 563 bp fragment in pT-12-D5 (Example 3). However, there was no translation initiation codon in the extended 693 bp fragment of SEQ ID NO:6.

A second round of the modified 5' RACE was carried out as described above, except that oligonucleotides ODMW541 (SEQ ID NO:41) and ODMW542 (SEQ ID NO:42) were used as gene-specific primers. Products between 200 bp and 400 bp were then purified from a gel and cloned into the pGEM-T-easy vector (Promega, Madison, Wis.). The ligated DNA was transformed into *E. coli* DH 10B and transformants were selected on LB agar containing ampicillin (100 μg/mL).

Analysis of the plasmid DNA from one transformant comprising the 5' region of the putative Δ5 desaturase gene confirmed the presence of the expected plasmid, designated pT-RD5-5'2$^{nd}$. Sequence analyses showed that pT-RD5-

5'2$^{nd}$ contained a fragment of 358 bp (SEQ ID NO:8), which over-lapped with 197 bp of the 5' end of the DNA fragment in pT-RD5-5'C2 described above and additionally provided 161 bp of 5' upstream sequence (SEQ ID NO:9). One-hundred sixteen (116) bp of the 5' extended fragment encoded the N-terminal portion of the putative Δ5 desaturase gene, including the translation initiation codon, thus providing the complete 5' sequence of the gene.

Example 5

Isolation of the 3'Coding Region of the *Peridinium* sp. CCMP626 Δ5 Desaturase Gene To isolate the C-terminal portion of the putative Δ5 desaturase identified in Example 3, a 3' RACE technique was utilized. The methodology was described above in Example 4; however, the primers used on both the first and second round of PCR amplification were as shown below in Table 5.

TABLE 5

Oligonucleotide Primers Used For 3' RACE

| PCR Amplification | Gene Specific Oligonucleotide | Generic Oligonucleotide |
|---|---|---|
| 1$^{st}$ Round | ODMW523 (SEQ ID NO: 43) | AUAP (SEQ ID NO: 44) |
| 2$^{nd}$ Round | ODMW524 (SEQ ID NO: 45) | AUAP (SEQ ID NO: 44) |

* Primer AUAP was supplied in Invitrogen's 3'-RACE kit (Carlsbad, CA).

Following isolation and purification of products (i.e., 200-500 bp), the fragments were cloned into the pGEM-T-easy vector (Promega) and transformed into *E. coli* DH10B, as in Example 4.

Analysis of the plasmid DNA from one transformant comprising the 3' region of the Δ5 desaturase gene confirmed the presence of the expected plasmid, designated pT-RD5-3'. Sequence analyses showed that pT-RD5-3' contained a fragment of 299 bp (SEQ ID NO:10), which over-lapped with 52 bp from the 3' end of the 563 bp fragment of pT-12-D5 (Example 3, SEQ ID NO:4) and provided 247 bp of additional 3' downstream sequence (SEQ ID NO:11). The first 202 bp of the extended 247 bp fragment included within pT-RD5-3' encoded the C-terminal coding region (including the translation stop codon) of the putative Δ5 desaturase gene. The sequence of pT-RD5-3' also corrected the sequence corresponding to Conserved Region 2, resulting from use of a degenerate oligonucleotide for initial PCR amplification of the 563 bp fragment in pT-12-D5 (Example 3).

After 2 rounds of 5' RACE and one round of 3' RACE, the DNA sequence of the entire putative *Peridinium* sp. CCMP626 Δ5 desaturase (RD5) coding region was determined. As shown in FIG. 4, the RD5 CDS was 1392 bp in length (SEQ ID NO:1) and encoded a polypeptide with 463 amino acids (SEQ ID NO:2), based on alignment of SEQ ID NOs:4, 6, 8 and 10. The results of BLASTP sequence analysis algorithms using the full length RD5 gene as the query sequence showed that it shared 67% identity and 81% similarity with the Δ5 fatty acid desaturase of *Phaeodactylum tricornutum* (GenBank Accession No. AAL92562; SEQ ID NO:14), with an Expectation value of 0.0. Additionally, the full length RD5 gene shared 64% identity and 76% similarity with the Δ8-sphingolipid desaturase of *Thalassiosira pseud-* *onana* (GenBank Accession No. AAX14502; SEQ ID NO:21), with an Expectation value of 2E-178.

Example 6

Generation of Construct pDMW368, Comprising RD5

The present Example describes the generation of pDMW368, comprising a chimeric FBAIN::RD5::Pex20 gene (FIG. 5C). This was designed to integrate the chimeric gene into the genome of *Yarrowia lipolytica* and then study the function of the *Peridinium* sp. CCMP626 Δ5 desaturase in *Yarrowia lipolytica*.

Based on the full length cDNA of RD5 (SEQ ID NO:1), oligonucleotides YL807 and YL810 (SEQ ID NOs:46 and 47, respectively) were used as primers to amplify the first portion of RD5 (FIG. 5A). Primer YL807 contained a NcoI site and primer YL810 contained a BamH1 site. Then, primers YL808 and YL809 (SEQ ID NOs:48 and 49, respectively) were used as primers to amplify the second portion of RD5. Primer YL809 contained a BamH1 site, while primer YL808 contained a NotI site. The PCR reactions, using primer pairs YL807/YL810 or YL808/YL809, with *Peridinium* sp. CCMP626 cDNA (Example 2) as template, were individually carried out in a 50 µl total volume comprising: PCR buffer (containing 10 mM KCl, 10 mM (NH$_4$)$_2$SO$_4$, 20 mM Tris-HCl (pH 8.75), 2 mM MgSO$_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.). The thermocycler conditions were set for 35 cycles at 95° C. for 1 min, 56° C. for 30 sec and 72° C. for 1 min, followed by a final extension at 72° C. for 10 min.

The individual PCR products were purified using a Qiagen PCR purification kit. The PCR products from the reaction amplified with primers YL807/YL810 were digested with NcoI and BamH1, while the PCR products from the reaction amplified with primers YL808/YL809 were digested with BamH1 and NotI. The NcoI/BamH1- and the BamH1/NotI-digested DNA fragments were purified following gel electrophoresis in 1% (w/v) agarose, and then directionally ligated with NcoI/NotI-digested pZUF17 (FIG. 5B; SEQ ID NO:22; comprising a synthetic Δ17 desaturase gene ["D17$^{s*}$"] derived from *Saprolegnia diclina* (U.S. Patent Publication No. 2003/0196217 A1), codon-optimized for expression in *Yarrowia lipolytica* (PCT Publication No. WO 2004/101757)). The product of this ligation was pDMW368 (FIG. 5C; SEQ ID NO:23, which thereby contained the following components:

TABLE 6

Components Of Plasmid pDMW368

| RE Sites And Nucleotides Within SEQ ID NO: 23 | Description Of Fragment And Chimeric Gene Components |
|---|---|
| EcoR I/BsiW I (6063-318) | FBAIN::RD5::Pex20, comprising: FBAIN: *Yarrowia lipolytica* FBAIN promoter (PCT Publication No. WO 2005/049805; U.S. Pat. No. 7,202,356) RD5: *Peridinium* sp. CCMP626 Δ5 desaturase (SEQ ID NO: 1 described herein) Pex20: Pex20 terminator sequence of Yarrowia Pex20 gene (GenBank Accession No. AF054613) |

TABLE 6-continued

Components Of Plasmid pDMW368

| RE Sites And Nucleotides Within SEQ ID NO: 23 | Description Of Fragment And Chimeric Gene Components |
|---|---|
| 1354-474 | ColE1 plasmid origin of replication |
| 2284-1424 | ampicillin-resistance gene (Amp$^R$) for selection in *E. coli* |
| 3183-4487 | *Yarrowia* autonomous replication sequence (ARS18; GenBank Accession No. A17608) |
| 6020-4533 | *Yarrowia Ura* 3 gene (GenBank Accession No. AJ306421) |

The term "FBAIN promoter" or "FBAIN promoter region" refers to the 5' upstream untranslated region in front of the 'ATG' translation initiation codon of the *Yarrowia lipolytica* fructose-bisphosphate aldolase enzyme (E.C. 4.1.2.13) encoded by the fba1 gene and that is necessary for expression, plus a portion of 5' coding region that has an intron of the fba1 gene.

Example 7

Generation of *Yarrowia lipolytica* Strain M4 to Produce about 8% DGLA of Total Lipids The present Example describes the construction of strain M4, derived from *Yarrowia lipolytica* ATCC #20362, capable of producing 8% DGLA relative to the total lipids. This strain was engineered to express the Δ6 desaturase/Δ6 elongase pathway, via introduction of construct pKUNF12T6E (FIG. 6A; SEQ ID NO:24). This construct was generated to integrate four chimeric genes (comprising a Δ12 desaturase, a Δ6 desaturase and two C$_{18/20}$ elongases) into the Ura3 loci of wild type *Yarrowia* strain ATCC #20362, to thereby enable production of DGLA. Thus, pKUNF12T6E contained the following components:

TABLE 7

Description of Plasmid pKUNF12T6E (SEQ ID NO: 24)

| RE Sites And Nucleotides Within SEQ ID NO: 24 | Description Of Fragment And Chimeric Gene Components |
|---|---|
| AscI/BsiWI (9420-8629) | 784 bp 5' portion of *Yarrowia Ura*3 gene (GenBank Accession No. AJ306421) |
| SphI/PacI (12128-1) | 516 bp 3' portion of *Yarrowia Ura*3 gene (GenBank Accession No. AJ306421) |
| SwaI/BsiWI (6380-8629) | FBAIN::EL1A::Pex20, comprising: FBAIN: *Yarrowia lipolytica* FBAIN promoter (PCT Publication No. WO 2005/049805; U.S. Pat. No. 7,202,356; labeled as "Fba1 + intron" in FIGURE) EL1S: codon-optimized elongase 1 gene (PCT Publication No. WO 2004/101753), derived from *Mortierella alpina* (GenBank Accession No. AX464731) Pex20: Pex20 terminator sequence from *Yarrowia* Pex20 gene (GenBank Accession No. AF054613) |
| Bgl/II/SwaI (4221-6380) | TEF::Δ6S::Lip1, comprising: TEF: *Yarrowia lipolytica* TEF promoter (GenBank Accession No. AF054508) Δ6S: codon-optimized Δ6 desaturase gene (PCT Publication No. WO 2004/101753), derived from *Mortierella alpina* (GenBank Accession No. AF465281) Lip1: Lip1 terminator sequence from *Yarrowia* Lip1 gene (GenBank Accession No. Z50020) |

TABLE 7-continued

Description of Plasmid pKUNF12T6E (SEQ ID NO: 24)

| RE Sites And Nucleotides Within SEQ ID NO: 24 | Description Of Fragment And Chimeric Gene Components |
|---|---|
| PmeI/ClaI (4207-1459) | FBA::F. Δ12::Lip2, comprising: FBA: *Yarrowia lipolytica* FBA promoter (PCT Publication No. WO 2005/049805; U.S. Pat. No. 7,202,356; labeled as "FBA1" in FIGURE) F. Δ12: *Fusarium moniliforme* Δ12 desaturase gene (PCT Publication No. WO 2005/047485) Lip2: Lip2 terminator sequence from *Yarrowia* Lip2 gene (GenBank Accession No. AJ012632) |
| ClaI/PacI (1459-1) | TEF::EL2Syn::XPR2, comprising: TEF: *Yarrowia lipolytica* TEF promoter (GenBank Accession No. AF054508) EL2Syn: codon-optimized elongase gene (SEQ ID NO: 25), derived from *Thraustochytrium aureum* (U.S. Pat. No. 6,677,145) XPR2: ~100 bp of the 3' region of the *Yarrowia* Xpr gene (GenBank Accession No. M17741) |

Plasmid pKUNF12T6E was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura-strains. Single colonies of Ura-strains were then inoculated into liquid MMU at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E, but not in the wild type *Yarrowia* control strain. Most of the selected 32 Ura⁻ strains produced about 6% DGLA of total lipids. There were 2 strains (i.e., strains M4 and 13-8) that produced about 8% DGLA of total lipids.

Example 8

Functional Analysis of RD5 Gene in *Yarrowia lipolytica* Strain M4

Plasmid pDMW368 (Example 6; comprising a chimeric FBAIN::RD5::Pex20 gene was transformed into strain M4 (Example 7), as described in the General Methods. The transformants were selected on MM plates. After 2 days grown at 30° C., 3 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 4.2% DGLA and 2.2% ARA of total lipids produced in all three transformants, wherein the conversion efficiency of DGLA to ARA in these three strains was determined to be about 35% (average). The conversion efficiency was measured according to the following formula: ([product]/[substrate+product])*100, where 'product' includes the immediate product and all products in the pathway derived from it. Thus, this experimental data demonstrated that the cloned *Peridinium* sp. CCMP626

Δ5 desaturase, described herein as SEQ ID NOs:1 and 2, efficiently desaturated DGLA to ARA.

Example 9

Synthesis of a Codon-Optimized Δ5 Desaturase Gene ("RD5S") for Expression in *Yarrowia lipolytica*

The codon usage of the Δ5 desaturase gene of *Peridinium* sp. CCMP626 (SEQ ID NOs:1 and 2; RD5) was optimized for expression in *Yarrowia lipolytica*, in a manner similar to that described in PCT Publication No. WO 2004/101753 and U.S. Pat. No. 7,125,672. Specifically, a codon-optimized Δ5 desaturase gene (designated "RD5S", SEQ ID NO:3) was designed based on the coding sequence of the Δ5 desaturase gene of RD5 (SEQ ID NO:2), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene*, 265(1-2):11-23 (2001)). In addition to modification of the translation initiation site, 247 bp of the 1392 bp coding region was modified (17.7%, FIGS. 7A and 7B) and 229 codons were optimized (49.4%). The GC content was increased from 49.3% within the wild type gene (i.e., RD5) to 54.2% within the synthetic gene (i.e., RD5S). A NcoI site and NotI sites were incorporated around the translation initiation codon and after the stop codon of RD5S (SEQ ID NO:3), respectively. None of the modifications in the codon-optimized gene changed the amino acid sequence of the encoded protein (SEQ ID NO:2). The designed RD5S gene was synthesized by GenScript Corporation (Piscataway, N.J.) and cloned into pUC57 (GenBank Accession No. Y14837) to generate pRD5S (SEQ ID NO:50; FIG. 6B) (RD5S labeled as "RD5S(626)" in Figure).

Example 10

Generation of Construct pZURD5S, Comprising RD5S

The present Example describes the construction of plasmid pZURD5S comprising a chimeric FBAIN::RD5S::Pex20 gene. Plasmid pZURD5S (SEQ ID NO:51; FIG. 6C) was constructed by replacing the Nco I/Not I fragment of pZUF17 (FIG. 5B; SEQ ID NO:22) with the Nco I/Not I RD5S fragment from pRD5S (SEQ ID NO:50; FIG. 6B). The product of this ligation was pZURD5S (FIG. 6C; SEQ ID NO:51), which thereby contained the following components:

TABLE 8

Components Of Plasmid pZURD5S

| RE Sites And Nucleotides Within SEQ ID NO:51 | Description Of Fragment And Chimeric Gene Components |
|---|---|
| EcoR I/BsiW I (7458-1713) | FBAIN::RD5S::Pex20, comprising: |
| | FBAIN: *Yarrowia lipolytica* FBAIN promoter (PCT Publication No. WO 2005/049805; U.S. Pat. No. 7,202,356) |
| | RD5S: codon-optimized Δ5 desaturase (SEQ ID NO: 3, described herein as RD5S), derived from *Peridinium* sp. CCMP626 (labeled as "RD5S(626)" in FIGURE) |
| | Pex20: Pex20 terminator sequence of *Yarrowia* Pex20 gene (GenBank Accession No. AF054613) |
| 2749-1869 | ColE1 plasmid origin of replication |
| 3679-2819 | ampicillin-resistance gene (Amp$^R$) for selection in *E. coli* |

TABLE 8-continued

Components Of Plasmid pZURD5S

| RE Sites And Nucleotides Within SEQ ID NO:51 | Description Of Fragment And Chimeric Gene Components |
|---|---|
| 4578-5882 | *Yarrowia* autonomous replication sequence (ARS18; GenBank Accession No. A17608) |
| 7415-5928 | *Yarrowia* Ura 3 gene (GenBank Accession No. AJ306421) |

Example 11

Expression of the Codon-Optimized Δ5 Desaturase ("RD5S") in *Yarrowia lipolytica* Strain M4

Plasmid pZURD5S (Example 10; comprising a chimeric FBAIN::RD5S::Pex20 gene) was used for transformation into strain M4 (Example 7), as described in the General Methods. Eight (8) transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by transesterification, and subsequently analyzed with a Hewlett-Packard 6890 GC.

The GC results showed that there were about 5.4% DGLA and 3.3% ARA of total lipids produced in all 8 transformants. The conversion efficiency whereby RD5S converted DGLA to ARA in these 8 strains was at an average rate of about 38%. The conversion efficiency was measured according to the following formula: ([product]/[substrate+product])*100, where 'product' includes the immediate product and all products in the pathway derived from it. Thus, this experimental data demonstrated that the codon-optimized Δ5 desaturase gene (RD5S, as set forth in SEQ ID NO:3) derived from *Peridinium* sp. CCMP626 was about 8.9% more efficient converting DGLA to ARA than the wild type RD5 (Example 8).

Example 12

Isolation of a *Pavlova lutheri* (CCMP459) Δ8 Desaturase

The present example describes the isolation of the *Pavlova lutheri* (CCMP459) Δ8 desaturase utilized in Example 3 and in FIG. 3 (also described in U.S. patent application Ser. No. 11/737,772 incorporated herein by reference). This required: synthesis of *Pavlova lutheri* (CCMP459) cDNA; library construction and sequencing; identification of Δ8 desaturase homologs; and, cloning of a full-length Δ8 desaturase from genomic DNA.

*Pavlova lutheri* (CCMP459) cDNA Synthesis, Library Construction and Sequencing

A cDNA library of *Pavlova lutheri* (CCMP459) was synthesized as described in PCT Publication No. WO 2004/071467 (published Aug. 26, 2004). Briefly, frozen pellets of Pav459 were obtained from the Provasoli-Guillard National Center for Culture of Marine Phytoplankton (CCMP, West Boothbay Harbor, Me.). These pellets were crushed in liquid nitrogen and total RNA was extracted from Pav459 by using the Qiagen RNeasy® Maxi Kit (Qiagen, Valencia, Calif.), per the manufacturer's instructions. From this total RNA, mRNA was isolated using oligo dT cellulose resin, which was then used for the construction of a cDNA library using the pSport1 vector (Invitrogen, Carlsbad, Calif.). The cDNA thus produced was directionally cloned (5' SalI/3' NotI into pSport1 vector. The Pav459 library contained approximately $6.1 \times 10^5$ clones per mL, each with an average insert size of approximately 1200 bp. The *Pavlova lutheri* library was named eps1c.

For sequencing, clones first were recovered from archived glycerol cultures grown/frozen in 384-well freezing media plates, and inoculated with an automatic QPix® colony picker (Genetix) in 96-well deep-well plates containing LB+100 mg/mL ampicillin. After growing 20 hrs at 37° C., cells were pelleted by centrifugation and stored at −20° C. Plasmids then were isolated on an Eppendorf 5Prime robot, using a modified 96-well format alkaline lysis miniprep method (Eppendorf PerfectPrep®). Briefly, a filter and vacuum manifold was used to facilitate removal of cellular debris after acetate precipitation. Plasmid DNA was then bound on a second filter plate directly from the filtrate, washed, dried and eluted.

Plasmids were end-sequenced in 384-well plates, using vector-primed T7 primer (SEQ ID NO:52) and the ABI Big-Dye version 3 Prism sequencing kit. For the sequencing reaction, 100-200 ng of template and 6.4 µmol. of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers.

Identification of Δ8 Desaturase Enzyme Homologs from *Pavlova lutheri* cDNA Library eps1c cDNA clones encoding *Pavlova lutheri* Δ8 desaturase homologs (hereby called Δ8 desaturases) were identified by conducting BLAST searches for similarity to sequences contained in the BLAST "nr" database (as described in Example 3). The P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone eps1c.pk002.f22 revealed similarity of the protein encoded by the cDNA to the Δ6 desaturase from *Rhizopus stolonifer* (SEQ ID NO:53) (NCBI Accession No. AAX22052 (GI 60499699), locus AAX22052, CDS AY795076; Lu et al., unpublished). The sequence of a portion of the cDNA insert from clone eps1c.pk002.f22 is shown in SEQ ID NO:54 (5' end of cDNA insert). Subsequently, the full insert sequence (eps1c.pk002.f22:fis) was obtained and is shown in SEQ ID NO:55. Sequence for the deduced amino acid sequence (from nucleotide 1 of SEQ ID NO:55 to the first stop codon at nucleotide 864 of SEQ ID NO:55) is shown in SEQ ID NO:56. Full insert sequencing was carried out using a modified transposition protocol. Clones identified for full insert sequencing were recovered from archived glycerol stocks as single colonies, and plasmid DNA was isolated via alkaline lysis. Plasmid templates were transposed via the Template Generation System (TGS II) transposition kit (Finnzymes Oy, Espoo, Finland), following the manufacturer's protocol. The transposed DNA was transformed into EH10B electro-competent cells (Edge BioSystems, Gaithersburg, Md.) via electroporation. Multiple transformants were randomly selected from each transposition reaction, plasmid DNA was prepared, and templates were sequenced as above (ABI BigDye v3.1) outward from the transposition event site, utilizing unique primers SeqE (SEQ ID NO:57) and SeqW (SEQ ID NO:58).

Sequence data was collected (ABI Prism Collections software) and assembled using the Phrap sequence assembly program (P. Green, University of Washington, Seattle). Assemblies were viewed by the Consed sequence editor (D. Gordon, University of Washington, Seattle) for final editing.

The amino acid sequence set forth in SEQ ID NO:56 was evaluated by BLASTP, yielding a pLog value of 19.52 (E value of 3e-20) versus the Δ6 desaturase from *Mortierella alpina* (NCBI Accession No. BAC82361 (GI 34221934), locus BAC82361, CDS AB070557; Sakuradani and Shimizu, *Biosci. Biotechnol. Biochem.*, 67:704-711 (2003)). Based on the results from the BLASTP comparison to the *Mortierella alpina* and other fatty acid desaturases, the *Pavlova lutheri* Δ8 desaturase was not full length and was lacking sequence at the 5' end.

Cloning a Full-Length Δ8 Desaturase from *Pavlova lutheri* Genomic DNA

Genomic DNA was isolated from *Pavlova lutheri* (CCMP459) using the Qiagen DNeasy® Plant Maxi Prep Kit according to the manufacturer's protocol. Using 1 maxi column per 1 gm of frozen cell pellet, a total of 122 µg of genomic DNA was isolated from 4 gm of *Pavlova lutheri* culture. The final concentration of genomic DNA was 22.8 ng/µL. GenomeWalker libraries were synthesized using the Universal GenomeWalker™ kit (BD Biosciences Clonetech, Palo Alto, Calif.) following the manufacturer's protocol (Prot #PT3042-1, version PRO3300). Briefly, four restriction digests were set up as per the protocol using 300 ng of genomic DNA per reaction. After phenol clean up, pellets were dissolved in 4 µL of water and adapters were ligated as per the protocol.

For the primary PCR, the Advantage®-GC Genomic PCR kit (BD Biosciences Clonetech) was used following the manufacturer's protocol (Prot #PT3090-1, version PR1X433). For each restriction digest, 1 µL of library was combined with 22.8 µL of PCR grade water, 10 µL of 5×GC Genomic PCR Reaction Buffer, 2.2 µL of 25 mM $Mg(CH_3CO_2)_2$, 10 µL of GC-Melt (5 M), 1 µL of 50×dNTP mix (10 mM each), 1 µL of Advantage-GC Genomic Pol. Mix (50×), 1 µL of Universal GenomeWalker™ primer AP1 (10 µM, SEQ ID NO:59) and 1 µL of GSP PvDES (10 µM, SEQ ID NO:60). After denaturation at 95° C., the following reaction conditions were repeated 35 times: 94° C. for 30 sec, 68° C. for 6 min. After these reaction conditions, an additional extension at 68° C. was carried out for 6 min followed by cooling to 15° C. until removed.

The primary PCR reaction for each library was analyzed by agarose gel electrophoresis and DNA bands with molecular weights around 6 kB, 3.5 kB, 2.5 kB and 1.2 kB were observed. DNA bands for each library were purified using the Zymoclean™ Gel DNA Recovery Kit (Zymo Research, Orange, Calif.) following the manufacturer's protocol. The resulting DNA was cloned into the PGEM®-T Easy Vector (Promega) following the manufacturer's protocol and inserts were sequenced using the T7 (SEQ ID NO:52) and M13-28Rev (SEQ ID NO:61) primers as described above. Additional sequence was then obtained using a gene-specific sequencing primer PavDES seq (SEQ ID NO:62) that was derived from the newly acquired sequence data. The full 5' end sequence obtained by genome walking is shown in SEQ ID NO:63. The sequence of the overlapping regions of the genomic sequence (SEQ ID NO:63) and the fully sequenced EST eps1c.pk002.f22:fis (SEQ ID NO:55) were aligned using Sequencher™ (Version 4.2, Gene Codes Corporation, Ann Arbor, Mich.) using the Large Gap assembly algorithm. Interestingly, the comparison showed that the EST that was originally sequenced (SEQ ID NO:55) was lacking 459 bp when compared to the genomic sequence (SEQ ID NO:63). This missing sequence in the EST appeared to be a deletion rather than an intron as no clear intron splice sites were identified in the genomic DNA at the 5' end of the gene. The genomic sequence for the 5' end (SEQ ID NO:63) was combined with the 3' end of the EST sequence (SEQ ID NO:55) to yield SEQ ID NO:64. Using EditSeq™ 6.1 sequence analysis software (DNASTAR Inc., Madison, Wis.), an ORF was identified (SEQ ID NO:17). The amino acid sequence coded for by SEQ ID NO:17 is shown in SEQ ID NO:18.

The amino acid sequence set forth in SEQ ID NO:18 was evaluated by BLASTP, yielding a pLog value of 35.10 (E value of 8e-36) versus the Δ6 desaturase from *Rhizopus stolonifer* (SEQ ID NO:65) (NCBI Accession No. ABB96724 (GI 83027409), locus ABB96724, CDS DQ291156; Zhang et al., unpublished). Furthermore, the *Pavlova lutheri* Δ8 desaturase is 78.0% identical to the *Pavlova salina* Δ8 desaturase sequence (SEQ ID NO:66) disclosed in PCT Publication No. WO 2005/103253 (published Apr. 22, 2005) using the Jotun Hein method. Sequence percent identity calculations performed by the Jotun Hein method (Hein, J. J., *Meth. Enz.*, 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2). The *Pavlova lutheri* Δ8 desaturase is 76.4% identical to the *Pavlova salina* Δ8 desaturase sequence using the Clustal V method. Sequence percent identity calculations performed by the Clustal V method (Higgins, D. G. and Sharp, P. M., *Comput. Appl. Biosci.*, 5:151-153 (1989); Higgins et al., *Comput. Appl. Biosci.*, 8:189-191 (1992)) were done using the MegAlign™ v6.1 program of the LASERGENE bioinformatics computing suite (DNASTAR Inc.) with the default parameters for pairwise alignment (KTUPLE=1, GAP PENALTY=3, WINDOW=5, DIAGONALS SAVED=5 and GAP LENGTH PENALTY=10). BLAST scores and probabilities indicate that the fragment of SEQ ID NO:17 encodes an entire *Pavlova lutheri* Δ8 desaturase.

FIGS. 8A and 8B show a Clustal V alignment (with default parameters) of SEQ ID NO:18 (the amino acid sequence of the *Pavlova lutheri* Δ8 desaturase), SEQ ID NO:66 (the amino acid sequence of *Pavlova salina* Δ8 desaturase sequence, supra), SEQ ID NO:16 (the amino acid sequence of *Euglena gracilis* Δ8 desaturase sequence disclosed as SEQ ID NO:2 in PCT Publication No. WO 2006/012325; published Feb. 2, 2006), SEQ ID NO:65 (the amino acid sequence for the *Rhizopus stolonifer* Δ6 fatty acid desaturase (NCBI Accession No. ABB96724, supra)) and SEQ ID NO:53 (the amino acid sequence for the *Rhizopus stolonifer* Δ6 fatty acid desaturase (NCBI Accession No. AAX22052, supra)). The results of the Clustal V alignment show that SEQ ID NO:18 is 76.4%, 22.6%, 22.2% and 22.2% identical to SEQ ID NO:66, SEQ ID NO:16, SEQ ID NO:65 and SEQ ID NO:53, respectively.

Example 13

Comparing the Substrate Specificity of the *Mortierella alpina* Δ5 Desaturase (MaD5) with the *Peridinium* sp. CCMP626 Δ5 Desaturase (RD5) in *Yarrowia lipolytica*

The present Example describes comparison of the substrate specificity of a *Mortierella alpina* Δ5 desaturase (MaD5; SEQ ID NOs:67 and 68), which is described in U.S. Pat. No. 6,075,183 and PCT Publication Nos. WO 2004/071467 and No. WO 2005/047479) to that of RD5 (SEQ ID NO:2) in *Yarrowia lipolytica*.

This work included the following steps: (1) construction of *Yarrowia* expression vector pY98 comprising MaD5; (2) transformation of pY98 and pDMW368 into *Yarrowia* strain Y2224; and, 3.) comparison of lipid profiles within transformant organisms comprising pY98 or pDMW368 after feeding fatty acid substrates.

Construction of *Yarrowia* Expression Vector pY98, Comprising MaD5

Plasmid pY5-22 (SEQ ID NO:69) is a shuttle plasmid that can replicate both in *E. coli* and *Yarrowia lipolytica*, containing the following: a *Yarrowia* autonomous replication sequence (ARS18; GenBank Accession No. M91600); a ColE1 plasmid origin of replication; an ampicillin-resistance gene (Amp$^R$) for selection in *E. coli*; a *Yarrowia* URA3 gene (GenBank Accession No. AJ306421) for selection in *Yarrowia*; and, a chimeric TEF::NcoI/NotI::XPR cassette, wherein "XPR" was ~100 bp of the 3' region of the *Yarrowia* Xpr gene (GenBank Accession No. M17741). Although the construction of plasmid pY5-22 is not described herein in detail, it was derived from pY5 (previously described in PCT Publication No. WO 2004/101757).

Plasmid pY5-22GPD (SEQ ID NO:70) was created from pY5-22 (SEQ ID NO:69), by replacing the TEF promoter with the *Yarrowia lipolytica* GPD promoter (SEQ ID NO:71) using techniques well known to one skilled in the art. The *Yarrowia* "GPD promoter" refers to the 5' upstream untranslated region in front of the 'ATG' translation initiation codon of a protein encoded by the *Yarrowia lipolytica* glyceraldehyde-3-phosphate dehydrogenase (GPD) gene and that is necessary for expression (PCT Publication No. WO 2005/003310). More specifically, the *Yarrowia lipolytica* GPD promoter was amplified from plasmid pYZDE2-S (SEQ ID NO:72; which was previously described in U.S. Patent Application No. 60/795,810 (the contents of which are hereby incorporated by reference)) using oligonucleotides GPDsense (SEQ ID NO:73) and GPDantisense (SEQ ID NO:74). The resulting DNA fragment was digested with SalI/NotI and cloned into the SalI/NotI fragment of pY5-22 (SEQ ID NO:69), thus replacing the TEF promoter and NcoI/NotI site with the GPD promoter and a unique NotI site, and thereby producing pY5-22GPD (SEQ ID NO:70).

The *Mortierella alpina* Δ5 desaturase gene (SEQ ID NO:67) was released from pKR136 (SEQ ID NO:75; which was previously described in PCT Publication No. WO 2004/071467 (the contents of which are hereby incorporated by reference)) by digestion with NotI and cloned into the NotI site of pY5-22GPD to produce pY98 (SEQ ID NO:76; FIG. 9).

Transformation of pY98 (Comprising MaD5) and pDMW368 (Comprising RD5) into *Yarrowia* Strain Y2224 and Comparison of Lipid Profiles Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Strain Y2224 was transformed with pY98 (SEQ ID NO:76, FIG. 9) and pDMW368 (SEQ ID NO:23; FIG. 5C; Example 6) as described in the General Methods.

Single colonies of transformant *Yarrowia lipolytica* containing pY98 (SEQ ID NO:76) or pDMW368 (SEQ ID NO:23) were grown in 3 mL MM lacking uracil supplemented with 0.2% tergitol at 30° C. for 1 day. After this, 0.1 mL was transferred to 3 mL of the same medium supplemented with either EDA, ETrA, DGLA, ETA or no fatty acid. These were incubated for 16 h at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.*, 276(1):38-46 (1990)) with 500 µL of 1% sodium methoxide for 30 min at 50° C. after which 500 µL of 1M NaCl and 100 µL of heptane were added. After thorough mixing and centrifugation, fatty acid methyl esters (FAMEs) were analyzed by GC.

FAMEs (5 µL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.).

The fatty acid profiles for *Yarrowia lipolytica* expressing pY98 (SEQ ID NO:76) or pDMW368 (SEQ ID NO:23) and fed various substrates are shown in FIG. 10A. In FIG. 10A shading indicates the substrates fed and products produced; fatty acids are identified as 16:0 (palmitate), 16:1, 18:0 (stearic acid), 18:1 (oleic acid), LA, GLA, ALA, STA, EDA, SCI (sciadonic acid or cis-5,11,14-eicosatrienoic acid; 20:3 ω-6), DGLA, ARA, ETrA, JUP (juniperonic acid or cis-5,11,14,17-eicosatrienoic acid; 20:4 ω-3), ETA and EPA. Fatty acid compositions were expressed as the weight percent (wt. %) of total fatty acids.

Percent Δ5 desaturation ("% delta-5 desat") of RD5 and MaD5 for each substrate is shown in FIG. 10B and was calculated by dividing the wt. % for product (either SCI, JUP, ARA or EPA) by the sum of the wt. % for the substrate and product (either EDA and SCI, ETrA and JUP, DGLA and ARA, or ETA and EPA, respectively) and multiplying by 100 to express as a %, depending on which substrate was fed.

The activities of MaD5 and RD5 are compared using the ratio of the percent Δ5 desaturation ("Ratio Desat R/Ma") in FIG. 10B and are calculated by dividing the percent Δ5 desaturation for RD5 on a particular substrate by the percent Δ5 desaturation for MaD5 on the same substrate.

The substrate specificity of RD5 and MaD5 for the correct ω-6 fatty acid substrate (i.e., DGLA) versus the by-product fatty acid (i.e., SCI) or the correct ω-3 fatty acid substrate (i.e., ETA) versus the by-product fatty acid (i.e., JUP) is also shown in FIG. 10B. Specifically, the substrate specificity ("Ratio Prod/By-Prod") for ω-6 substrates was calculated by dividing the percent Δ5 desaturation (% delta-5 desat) for DGLA by the percent Δ5 desaturation (% delta-5 desat) for EDA and is shown on the same lines as the results for DGLA. The substrate specificity ("Ratio Prod/By-Prod") for ω-3 substrates was calculated by dividing the percent Δ5 desaturation (% delta-5 desat) for ETA by the percent Δ5 desaturation (% delta-5 desat) for ETrA and is shown on the same lines as the results for ETA. Furthermore, the ratio of substrate specificity ("Ratio Prod/By-Prod R/Ma") for ω-6 substrates was determined by dividing the substrate specificity for RD5 on the ω-6 substrates (i.e., DGLA/EDA) by that for MaD5. The ratio of substrate specificity ("Ratio Prod/By-Prod R/Ma") for ω-3 substrates was calculated by dividing the substrate specificity for RD5 on the ω-3 substrates (i.e., ETA/ETrA) by that for MaD5.

The preference of RD5 and MaD5 for ω-6 or ω-3 substrates is compared using the ratio of the percent Δ5 desaturation ("Ratio n-6/n-3") in FIG. 10B and is calculated by dividing the percent Δ5 desaturation for RD5 and MaD5 on a particular ω-6 substrate (either DGLA or EDA) by the percent Δ5 desaturation on the corresponding ω-3 substrate (either ETA or ETrA, respectively).

From the results in FIG. 10B, it is clear that RD5 is approximately 3.0- to 9,7-fold more active in *Yarrowia* than MaD5 when DGLA, EDA, ETrA and ETA are used as substrates. The substrate specificity of RD5 compared to MaD5 (RD5/MaD5) for the correct ω-6 substrate (i.e., DGLA versus EDA) is approximately 0.4 and for the ω-3 substrate (i.e., ETA versus ETrA) is approximately 0.6. RD5 also has an approximate 1,4-fold preference for ω-6 substrates (i.e., EDA and DGLA) over the ω-3 substrates (i.e., ETrA and ETA), respectively.

What is claimed is:

1. An isolated nucleic acid molecule selected from the group consisting of:
   a) an isolated nucleotide sequence encoding a Δ5 desaturase enzyme as set forth in SEQ ID NO:2;
   b) an isolated nucleotide sequence that hybridizes with (a) under the following hybridization conditions: 0.1×SSC, 0.1% SDS, 65° C. and washed with 2×SSC, 0.1% SDS, wherein said nucleotide sequence encodes a delta-5 desaturase followed by 0.1×SSC, 0.1% SDS; and,
   c) an isolated nucleotide sequence that is completely complementary to (a) or (b).

2. The isolated nucleic acid molecule of claim 1, wherein at least 229 codons are codon-optimized for expression in *Yarrowia*.

3. The isolated nucleic acid molecule of claim 1 selected from the group of SEQ ID NOs:1 and 3.

4. An isolated nucleic acid fragment of claim 1 isolated from *Peridinium* sp. CCMP626.

5. An isolated nucleic acid molecule comprising a first nucleotide sequence encoding a Δ5 desaturase enzyme of at least 463 amino acids that has at least 95% identity based on BLASTP algorithms when compared to a polypeptide having the sequence as set forth in SEQ ID NO:2;
   or a second nucleotide sequence comprising the complement of the first nucleotide sequence.

6. A chimeric gene comprising the isolated nucleic acid molecule of any one of claims 1-5 operably linked to at least one regulatory sequence.

7. A transformed *Yarrowia* sp. comprising the isolated nucleic acid molecule of claim 1.

8. A method for the production of arachidonic acid comprising:
   a) providing a host cell comprising:
      (i) an isolated nucleotide molecule encoding a Δ5 desaturase polypeptide having at least 95% identity when compared to a polypeptide having the amino acid sequence as set forth in SEQ ID NO:2, based on BLASTP algorithms; and,
      (ii) a source of dihomo-γ-linolenic acid;
   b) growing the host cell of step (a) under conditions wherein the nucleic acid fragment encoding the Δ5 desaturase polypeptide is expressed and the dihomo-γ-linolenic acid is converted to arachidonic acid; and,
   c) optionally recovering the arachidonic acid of step (b).

9. A method for the production of eicosapentaenoic acid comprising:
   a) providing a host cell comprising:
      (i) an isolated nucleotide molecule encoding a Δ5 desaturase polypeptide having at least 95% identity when compared to a polypeptide having the amino acid sequence as set forth in SEQ ID NO:2, based on BLASTP algorithms; and,
      (ii) a source of eicosatetraenoic acid;
   b) growing the host cell of step (a) under conditions wherein the nucleic acid fragment encoding the Δ5 desaturase polypeptide is expressed and the eicosatetraenoic acid is converted to eicosapentaenoic acid; and,
   c) optionally recovering the eicosapentaenoic acid of step (b).

10. A method according to either of claims 8 or 9 wherein the isolated nucleic acid molecule encoding the Δ5 desaturase polypeptide is set forth in SEQ ID NO:2, wherein at least 229 codons are codon-optimized for expression in *Yarrowia*.

11. A method according to either of claims 8 or 9 wherein the isolated nucleic acid molecule encodes a Δ5 desaturase polypeptide having the amino acid sequence as set forth in SEQ ID NO:2.

12. A method according to either of claims 8 or 9 wherein:
   a) the isolated nucleic acid molecule has the nucleic acid sequence selected from the group consisting of SEQ ID NOs:1 and SEQ ID NO:3; and,
   b) the host cell is *Yarrowia lipolytica*.

13. A method according to either of claims 8 or 9, wherein the host cell is selected from the group consisting of: algae, bacteria, yeast, and fungi.

14. A method according to claim 13 wherein the host cell is a fungus selected from the group consisting of: *Thraustochytrium*, *Schizochytrium* and *Mortierella*.

15. A method according to claim 13 wherein the yeast is an oleaginous yeast.

16. A method according to claim 15 wherein the oleaginous yeast is selected from the group consisting of: *Yarrowia*, *Candida*, *Rhodotorula*, *Rhodosporidium*, *Cryptococcus*, *Trichosporon* and *Lipomyces*.

* * * * *

SEQUENCE LISTING

<160> NUMBER OF SEQ ID NOS: 76

<210> SEQ ID NO 1
<211> LENGTH: 1392
<212> TYPE: DNA
<213> ORGANISM: Peridinium sp. CCMP626
<220> FEATURE:
<221> NAME/KEY: misc_feature
<223> OTHER INFORMATION: delta-5 desaturase

```
<400> SEQUENCE: 1
atggctccag atgcggacaa gttgagacag cgcaaggcgc aatcgattca agacacggct      60
gattcgcaag ctaccgaact caagattggc accctgaagg gcttgcaggg gacagaaatc     120
gtcattgatg gagacattta cgatataaaa gactttgatc accccggtgg tgaatccatc     180
atgactttg gggaaacga tgtcaccgcc acgtacaaga tgatccaccc ctaccactct       240
aagcaccatt tggagaagat gaagaaagtg gacgagttc cggactacac ctcggaatac      300
aagtttgata ctcccttga gcgtgaaatc aagcaagagg tcttcaagat tgtgcgacga      360
ggccgcgagt ttggaacacc tggatacttc ttccgggctt tctgctacat tggacttttc     420
ttttacttgc agtatttgtg ggtcacgact cccactacct tgccttggc gatcttctat      480
ggtgtttcgc aagctttcat tggtttgaac gtacaacatg atgccaacca cggagctgcc     540
tccaagaagc cttggatcaa taacttgcta ggattggggg ctgactttat cggaggttcc     600
aaatggttgt ggatgaacca gcactggacg caccacacat acaccaacca ccatgagaag     660
gatcccgatg ccttgggcgc tgaaccaatg ttgttgttca atgattatcc cttgggtcac     720
ccaaagcgta ctttgattca ccacttccag gccttctatt accttttcgt cttggccgga     780
tactgggtct cttcggtctt caaccctcaa atttttggact tgcaacaccg cggtgctcaa     840
gcggttggaa tgaaaatgga gaacgattac attgccaaaa gccgaaagta tgccatcttc     900
ttgcgtctct tgtatattta caccaacatt gtcgctccga tccaaaacca aggcttctcg     960
ttgaccgtgg tcgcccacat tttgaccatg ggcgtcgctt ccagtttgac tttggcgact    1020
cttttttgcct tgtcgcacaa ttttgaaaac gcggatcgcg atcccactta cgaggcccgc    1080
aagggaggag agcctgtttg ttggttcaag tcgcaagtcg aaacctcgtc aacttacgga    1140
ggtttcatct cgggttgctt gacgggcgga ctcaacttcc aagtggaaca ccacttgttc    1200
cctcgtatga gttcggcctg gtaccccctac attgccccta ctgttcgaga ggtttgcaaa    1260
aagcacggag tcaagtacgc atactatccc tgggtctggc aaaacttgat ttcaactgtc    1320
aagtatctgc atcaaagcgg aactggatcc aactggaaga atggcgccaa ccccctactcg    1380
ggaaaattgt aa                                                         1392

<210> SEQ ID NO 2
<211> LENGTH: 463
<212> TYPE: PRT
<213> ORGANISM: Peridinium sp. CCMP626

<400> SEQUENCE: 2

Met Ala Pro Asp Ala Asp Lys Leu Arg Gln Arg Lys Ala Gln Ser Ile
1               5                   10                  15

Gln Asp Thr Ala Asp Ser Gln Ala Thr Glu Leu Lys Ile Gly Thr Leu
            20                  25                  30

Lys Gly Leu Gln Gly Thr Glu Ile Val Ile Asp Gly Asp Ile Tyr Asp
        35                  40                  45

Ile Lys Asp Phe Asp His Pro Gly Gly Glu Ser Ile Met Thr Phe Gly
    50                  55                  60

Gly Asn Asp Val Thr Ala Thr Tyr Lys Met Ile His Pro Tyr His Ser
65                  70                  75                  80

Lys His His Leu Glu Lys Met Lys Lys Val Gly Arg Val Pro Asp Tyr
                85                  90                  95

Thr Ser Glu Tyr Lys Phe Asp Thr Pro Phe Glu Arg Glu Ile Lys Gln
            100                 105                 110
```

```
Glu Val Phe Lys Ile Val Arg Arg Gly Arg Glu Phe Gly Thr Pro Gly
            115                 120                 125

Tyr Phe Phe Arg Ala Phe Cys Tyr Ile Gly Leu Phe Phe Tyr Leu Gln
        130                 135                 140

Tyr Leu Trp Val Thr Thr Pro Thr Thr Phe Ala Leu Ala Ile Phe Tyr
145                 150                 155                 160

Gly Val Ser Gln Ala Phe Ile Gly Leu Asn Val Gln His Asp Ala Asn
                165                 170                 175

His Gly Ala Ala Ser Lys Lys Pro Trp Ile Asn Asn Leu Leu Gly Leu
            180                 185                 190

Gly Ala Asp Phe Ile Gly Gly Ser Lys Trp Leu Trp Met Asn Gln His
        195                 200                 205

Trp Thr His His Thr Tyr Thr Asn His His Glu Lys Asp Pro Asp Ala
    210                 215                 220

Leu Gly Ala Glu Pro Met Leu Leu Phe Asn Asp Tyr Pro Leu Gly His
225                 230                 235                 240

Pro Lys Arg Thr Leu Ile His His Phe Gln Ala Phe Tyr Tyr Leu Phe
                245                 250                 255

Val Leu Ala Gly Tyr Trp Val Ser Ser Val Phe Asn Pro Gln Ile Leu
            260                 265                 270

Asp Leu Gln His Arg Gly Ala Gln Ala Val Gly Met Lys Met Glu Asn
        275                 280                 285

Asp Tyr Ile Ala Lys Ser Arg Lys Tyr Ala Ile Phe Leu Arg Leu Leu
    290                 295                 300

Tyr Ile Tyr Thr Asn Ile Val Ala Pro Ile Gln Asn Gln Gly Phe Ser
305                 310                 315                 320

Leu Thr Val Val Ala His Ile Leu Thr Met Gly Val Ala Ser Ser Leu
                325                 330                 335

Thr Leu Ala Thr Leu Phe Ala Leu Ser His Asn Phe Glu Asn Ala Asp
            340                 345                 350

Arg Asp Pro Thr Tyr Glu Ala Arg Lys Gly Gly Glu Pro Val Cys Trp
        355                 360                 365

Phe Lys Ser Gln Val Glu Thr Ser Ser Thr Tyr Gly Gly Phe Ile Ser
370                 375                 380

Gly Cys Leu Thr Gly Gly Leu Asn Phe Gln Val Glu His His Leu Phe
385                 390                 395                 400

Pro Arg Met Ser Ser Ala Trp Tyr Pro Tyr Ile Ala Pro Thr Val Arg
                405                 410                 415

Glu Val Cys Lys Lys His Gly Val Lys Tyr Ala Tyr Tyr Pro Trp Val
            420                 425                 430

Trp Gln Asn Leu Ile Ser Thr Val Lys Tyr Leu His Gln Ser Gly Thr
        435                 440                 445

Gly Ser Asn Trp Lys Asn Gly Ala Asn Pro Tyr Ser Gly Lys Leu
450                 455                 460

<210> SEQ ID NO 3
<211> LENGTH: 1392
<212> TYPE: DNA
<213> ORGANISM: Peridinium sp. CCMP626
<220> FEATURE:
<221> NAME/KEY: misc_feature
<223> OTHER INFORMATION: synthetic delta-5 desaturase (codon-optimized)
      for Yarrowia lipolytica

<400> SEQUENCE: 3
atggctcccg acgccgacaa gctgcgacag cgaaaggctc agtccatcca ggacactgcc      60
```

```
gattctcagg ctaccgagct caagattggc accctgaagg gtctccaagg caccgagatc      120
gtcattgatg gcgacatcta cgacatcaaa gacttcgatc accctggagg cgaatccatc      180
atgacctttg gtggcaacga cgttactgcc acctacaaga tgattcatcc ctaccactcg      240
aagcatcacc tggagaagat gaaaaaggtc ggtcgagtgc ccgactacac ctccgagtac      300
aagttcgata ctcccttcga acgagagatc aaacaggagg tcttcaagat tgtgcgaaga      360
ggtcgagagt ttggaacacc tggctacttc tttcgagcct tctgctacat cggtctcttc      420
ttttacctgc agtatctctg ggttaccact cctaccactt tcgcccttgc tatcttctac      480
ggtgtgtctc aggccttcat tggcctgaac gtccagcacg acgccaacca cggagctgcc      540
tccaaaaagc cctggatcaa caatttgctc ggcctgggtg ccgactttat cggaggctcc      600
aagtggctct ggatgaacca gcactggacc catcacactt acaccaacca tcacgagaag      660
gatcccgacg ccctgggtgc agagcctatg ctgctcttca cgactatccc tttgggtcac      720
cccaagcgaa ccctcattca tcacttccaa gccttctact atctgtttgt ccttgctggc      780
tactgggtgt cttcggtgtt caaccctcag atcctggacc tccagcaccg aggtgcccag      840
gctgtcggca tgaagatgga gaacgactac attgccaagt ctcgaaagta cgctatcttc      900
ctgcgactcc tgtacatcta caccaacatt gtggctccca tccagaacca aggcttttcg      960
ctcaccgtcg ttgctcacat tcttactatg ggtgtcgcct ccagcctgac cctcgctact     1020
ctgttcgccc tctcccacaa cttcgagaac gcagatcggg atcccaccta cgaggctcga     1080
aagggaggcg agcctgtctg ttggttcaag tcgcaggtgg aaacctcctc tacttacggt     1140
ggcttcattt ccggttgcct tacaggcgga ctcaactttc aggtcgagca tcacctgttt     1200
cctcgaatgt cctctgcctg gtaccctac atcgctccta ccgttcgaga ggtctgcaaa     1260
aagcacggcg tcaagtacgc ctactatccc tgggtgtggc agaacctcat ctcgaccgtc     1320
aagtacctgc atcagtccgg aactggctcg aactggaaga acggtgccaa tccctactct     1380
ggcaagctgt aa                                                         1392

<210> SEQ ID NO 4
<211> LENGTH: 563
<212> TYPE: DNA
<213> ORGANISM: Artificial Sequence
<220> FEATURE:
<223> OTHER INFORMATION: 563 bp fragment of pT-12-D5

<400> SEQUENCE: 4
ggtcatcatg tttataccaa ccaccatgag aaggatcccg atgccttggg cgctgaacca       60
atgttgttgt tcaatgatta tcccttgggt cacccaaagc gtactttgat tcaccacttc      120
caggccttct attacttttt cgtcttggcc ggatactggg tctcttcggt cttcaaccct      180
caaattttgg acttgcaaca ccgcggtgct caagcggttg gaatgaaaat ggagaacgat      240
tacattgcca aaagccgaaa gtatgccatc ttcttgcgtc tcttgtatat ttacaccaac      300
attgtcgctc cgatccaaaa ccaaggcttc tcgttgaccg tggtcgccca cattttgacc      360
atgggcgtcg cttccagttt gactttggcg actcttttg cctcgtcgca caattttgaa      420
aacgcggatc gcgatcccac ttacgaggcc cgcaaggggg agagcctgt tgttggttc       480 aagtcgcaag tcgaaacctc gtcaacttac ggaggtttca tctcggggttg cttgacgggc      540 ggactcaact tccaagtatc aca                                             563

<210> SEQ ID NO 5
```

-continued

```
<211> LENGTH: 187
<212> TYPE: PRT
<213> ORGANISM: Artificial Sequence
<220> FEATURE:
<223> OTHER INFORMATION: translation of 563 bp fragment of pT-12-D5

<400> SEQUENCE: 5

Gly His His Val Tyr Thr Asn His His Glu Lys Asp Pro Asp Ala Leu
1               5                   10                  15

Gly Ala Glu Pro Met Leu Leu Phe Asn Asp Tyr Pro Leu Gly His Pro
            20                  25                  30

Lys Arg Thr Leu Ile His His Phe Gln Ala Phe Tyr Tyr Leu Phe Val
        35                  40                  45

Leu Ala Gly Tyr Trp Val Ser Ser Val Phe Asn Pro Gln Ile Leu Asp
    50                  55                  60

Leu Gln His Arg Gly Ala Gln Ala Val Gly Met Lys Met Glu Asn Asp
65                  70                  75                  80

Tyr Ile Ala Lys Ser Arg Lys Tyr Ala Ile Phe Leu Arg Leu Leu Tyr
                85                  90                  95

Ile Tyr Thr Asn Ile Val Ala Pro Ile Gln Asn Gln Gly Phe Ser Leu
            100                 105                 110

Thr Val Val Ala His Ile Leu Thr Met Gly Val Ala Ser Ser Leu Thr
        115                 120                 125

Leu Ala Thr Leu Phe Ala Ser Ser His Asn Phe Glu Asn Ala Asp Arg
    130                 135                 140

Asp Pro Thr Tyr Glu Ala Arg Lys Gly Gly Glu Pro Val Cys Trp Phe
145                 150                 155                 160

Lys Ser Gln Val Glu Thr Ser Ser Thr Tyr Gly Gly Phe Ile Ser Gly
                165                 170                 175

Cys Leu Thr Gly Gly Leu Asn Phe Gln Val Ser
            180                 185

<210> SEQ ID NO 6
<211> LENGTH: 693
<212> TYPE: DNA
<213> ORGANISM: Artificial Sequence
<220> FEATURE:
<223> OTHER INFORMATION: 693 bp fragment of pT-RD5-5'C2
<220> FEATURE:
<221> NAME/KEY: misc_feature
<222> LOCATION: (10)..(10)
<223> OTHER INFORMATION: n is a, c, g, or t

<400> SEQUENCE: 6
aatcgtcatn gatggagaca tttacgatat aaaagacttt gatcaccccg gtggtgaatc      60
catcatgact tttgggggaa acgatgtcac cgccacgtac aagatgatcc accctacca     120 ctctaagcac catttggaga agatgaagaa agtgggacga gttccggact acacctcgga     180
atacaagttt gatactccct tgagcgtga aatcaagyaa gaggtcttca agattgtgcg      240
acgaggccgc gagtttggaa cacctggata cttcttccgg gctttctgct acattggact     300
tttcttttac ttgcagtatt tgtgggtcac gactcccact acctttgcct tggcgatctt     360
ctatggtgtt tcgcaagctt tcattggttt gaacgtacaa catgatgcca accacggagc     420
tgcctccaag aagccttgga tcaataactt gctaggattg gggctgact ttatcggagg      480 ttccaaatgg ttgtggatga accagcactg gacgcaccac acatacacca accaccatga     540
gaaggatccc gatgccttgg gcgctgaacc aatgttgttg ttcaatgatt atcccttggg     600
tcacccaaag cgtactttga ttcaccactt ccaggccttc tattaccttt tcgtcttggc     660
```

-continued

```
cggatactgg gtctcttcgg tcttcaaccc tca                              693

<210> SEQ ID NO 7
<211> LENGTH: 511
<212> TYPE: DNA
<213> ORGANISM: Artificial Sequence
<220> FEATURE:
<223> OTHER INFORMATION: 511 bp 5' extended fragment of pT-RD5-5'C2

<400> SEQUENCE: 7
aatcgtcatt gatggagaca tttacgatat aaaagacttt gatcaccccg gtggtgaatc    60
catcatgact tttgggggaa acgatgtcac cgccacgtac aagatgatcc acccctacca   120
ctctaagcac catttggaga agatgaagaa agtgggacga gttccggact acacctcgga   180
atacaagttt gatactccct tgagcgtga atcaagyaa gaggtcttca agattgtgcg    240
acgaggccgc gagtttggaa cacctggata cttcttccgg gctttctgct acattggact   300
tttcttttac ttgcagtatt tgtgggtcac gactcccact acctttgcct tggcgatctt   360
ctatggtgtt tcgcaagctt tcattggttt gaacgtacaa catgatgcca accacggagc   420
tgcctccaag aagccttgga tcaataactt gctaggattg ggggctgact ttatcggagg   480
ttccaaatgg ttgtggatga accagcactg g                                  511

<210> SEQ ID NO 8
<211> LENGTH: 358
<212> TYPE: DNA
<213> ORGANISM: Artificial Sequence
<220> FEATURE:
<223> OTHER INFORMATION: 358 bp fragment of pT-RD5-5'2nd

<400> SEQUENCE: 8
gatttctttc gttggcattt ttcgttggga aagactcttg caacgatggc tccagatgcg    60
gacaagttga gacagcgcaa ggcgcaatcg attcaagaca cggctgattc gcaagctacc   120
gaactcaaga ttggcaccct gaagggcttg caggggacag aaatcgtcat tgatggagac   180
atttacgata taaaagactt tgatcacccc ggtggtgaat ccatcatgac ttttggagga   240
aacgatgtca ctgccacgta caagatgatc caccctacc actctaagca ccatttggag   300
aagatgaaga agtgggacg agttctggac tacacctcgg aatacaagtt tgatactc     358

<210> SEQ ID NO 9
<211> LENGTH: 161
<212> TYPE: DNA
<213> ORGANISM: Artificial Sequence
<220> FEATURE:
<223> OTHER INFORMATION: 161 bp 5' extended fragment of pT-RD5-5'2nd

<400> SEQUENCE: 9
gatttctttc gttggcattt ttcgttggga aagactcttg caacgatggc tccagatgcg    60
gacaagttga gacagcgcaa ggcgcaatcg attcaagaca cggctgattc gcaagctacc   120
gaactcaaga ttggcaccct gaagggcttg caggggacag a                       161

<210> SEQ ID NO 10
<211> LENGTH: 299
<212> TYPE: DNA
<213> ORGANISM: Artificial Sequence
<220> FEATURE:
<223> OTHER INFORMATION: 299 bp fragment of pT-RD5-3'

<400> SEQUENCE: 10
```

-continued

```
gaggtttcat ctcgggttgt ttgacgggcg gactcaactt tcaagtggaa caccacttgt    60
tccctcgtat gagttcggcc tggtacccct acattgcccc tgctgttcga gaggtttgca   120
aaaagcacgg agtcaagtac gcatactatc cctgggtctg gcaaaacttg atttcaactg   180
tcaagtatct gcatcaaagc ggaactggat ccaactggaa gaatggcgcc aaccccctact  240 cgggaaaatt gtaaatgaat tctagtcaag atgggtcact gcattcaaaa aaaaaaaaa    299
```

<210> SEQ ID NO 11
<211> LENGTH: 247
<212> TYPE: DNA
<213> ORGANISM: Artificial Sequence
<220> FEATURE:
<223> OTHER INFORMATION: 247 bp of 3' downstream sequence of pT-RD5-3'

<400> SEQUENCE: 11

```
ccacttgttc cctcgtatga gttcggcctg gtaccoctac attgcccctg ctgttcgaga    60
ggtttgcaaa aagcacggag tcaagtacgc atactatccc tgggtctggc aaaacttgat   120
ttcaactgtc aagtatctgc atcaaagcgg aactggatcc aactggaaga atggcgccaa   180
cccctactcg ggaaaattgt aaatgaattc tagtcaagat gggtcactgc attcaaaaaa   240
aaaaaaa                                                             247
```

<210> SEQ ID NO 12
<211> LENGTH: 456
<212> TYPE: PRT
<213> ORGANISM: Pythium irregulare (GenBank Accession No. AAL13311)
<220> FEATURE:
<221> NAME/KEY: MISC_FEATURE
<223> OTHER INFORMATION: delta-5 desaturase

<400> SEQUENCE: 12

```
Met Gly Thr Asp Gln Gly Lys Thr Phe Thr Trp Gln Glu Val Ala Lys
1               5                   10                  15

His Asn Thr Ala Lys Ser Ala Trp Val Ile Ile Arg Gly Glu Val Tyr
            20                  25                  30

Asp Val Thr Glu Trp Ala Asp Lys His Pro Gly Gly Ser Glu Leu Ile
        35                  40                  45

Val Leu His Ser Gly Arg Glu Cys Thr Asp Thr Phe Tyr Ser Tyr His
    50                  55                  60

Pro Phe Ser Asn Arg Ala Asp Lys Ile Leu Ala Lys Tyr Lys Ile Gly
65                  70                  75                  80

Lys Leu Val Gly Gly Tyr Glu Phe Pro Val Phe Lys Pro Asp Ser Gly
                85                  90                  95

Phe Tyr Lys Glu Cys Ser Glu Arg Val Ala Glu Tyr Phe Lys Thr Asn
            100                 105                 110

Asn Leu Asp Pro Lys Ala Ala Phe Ala Gly Leu Trp Arg Met Val Phe
        115                 120                 125

Val Phe Ala Val Ala Ala Leu Ala Tyr Met Gly Met Asn Glu Leu Ile
    130                 135                 140

Pro Gly Asn Val Tyr Ala Gln Tyr Ala Trp Gly Val Val Phe Gly Val
145                 150                 155                 160

Phe Gln Ala Leu Pro Leu Leu His Val Met His Asp Ser Ser His Ala
                165                 170                 175

Ala Cys Ser Ser Ser Pro Ala Met Trp Gln Ile Ile Gly Arg Gly Val
            180                 185                 190

Met Asp Trp Phe Ala Gly Ala Ser Met Val Ser Trp Leu Asn Gln His
        195                 200                 205
```

Val Val Gly His His Ile Tyr Thr Asn Val Ala Gly Ala Asp Pro Asp
            210                 215                 220

Leu Pro Val Asp Phe Glu Ser Asp Val Arg Arg Ile Val His Arg Gln
225                 230                 235                 240

Val Leu Leu Pro Ile Tyr Lys Phe Gln His Ile Tyr Leu Pro Pro Leu
            245                 250                 255

Tyr Gly Val Leu Gly Leu Lys Phe Arg Ile Gln Asp Val Phe Glu Thr
            260                 265                 270

Phe Val Ser Leu Thr Asn Gly Pro Val Arg Val Asn Pro His Pro Val
            275                 280                 285

Ser Asp Trp Val Gln Met Ile Phe Ala Lys Ala Phe Trp Thr Phe Tyr
            290                 295                 300

Arg Ile Tyr Ile Pro Leu Val Trp Leu Lys Ile Thr Pro Ser Thr Phe
305                 310                 315                 320

Trp Gly Val Phe Phe Leu Ala Glu Phe Thr Thr Gly Trp Tyr Leu Ala
            325                 330                 335

Phe Asn Phe Gln Val Ser His Val Ser Thr Glu Cys Glu Tyr Pro Cys
            340                 345                 350

Gly Asp Ala Pro Ser Ala Glu Val Gly Asp Glu Trp Ala Ile Ser Gln
            355                 360                 365

Val Lys Ser Ser Val Asp Tyr Ala His Gly Ser Pro Leu Ala Ala Phe
            370                 375                 380

Leu Cys Gly Ala Leu Asn Tyr Gln Val Thr His His Leu Tyr Pro Gly
385                 390                 395                 400

Ile Ser Gln Tyr His Tyr Pro Ala Ile Ala Pro Ile Ile Asp Val
            405                 410                 415

Cys Lys Lys Tyr Asn Ile Lys Tyr Thr Val Leu Pro Thr Phe Thr Glu
            420                 425                 430

Ala Leu Leu Ala His Phe Lys His Leu Lys Asn Met Gly Glu Leu Gly
            435                 440                 445

Lys Pro Val Glu Ile His Met Gly
    450                 455

<210> SEQ ID NO 13
<211> LENGTH: 477
<212> TYPE: PRT
<213> ORGANISM: Phytophthora megasperma (GenBank Accession No. CAD53323)
<220> FEATURE:
<221> NAME/KEY: MISC_FEATURE
<223> OTHER INFORMATION: delta-5 desaturase

<400> SEQUENCE: 13

Met Ala Pro Ile Glu Thr Val Lys Asp Ala Asn Glu Gly Leu His Gln
1               5                   10                  15

Arg Lys Gly Ala Ala Ala Ser Lys Asp Thr Thr Thr Phe Thr Trp
            20                  25                  30

Gln Asp Val Ala Lys His Asn Thr Ala Lys Ser Ala Trp Val Thr Ile
            35                  40                  45

Arg Gly Val Val Tyr Asp Val Thr Glu Trp Ala Asp Arg His Pro Gly
        50                  55                  60

Gly Arg Glu Leu Val Leu Leu His Ser Gly Arg Glu Cys Thr Asp Thr
65                  70                  75                  80

Phe Asp Ser Tyr His Pro Phe Ser Asp Arg Ala Asp Lys Ile Leu Ala
                85                  90                  95

Lys Tyr Ala Ile Gly Lys Leu Val Gly Gly Ser Glu Phe Pro Thr Tyr

```
                100                 105                 110
Lys Pro Asp Thr Gly Phe Tyr Lys Glu Cys Cys Asp Arg Val Asn Gln
        115                 120                 125

Tyr Phe Lys Asp Asn Lys Leu Asp Pro Arg Ser Pro Tyr Ser Gly Leu
    130                 135                 140

Trp Arg Met Ile Leu Val Ala Ile Val Gly Val Ala Tyr Met Gly
145                 150                 155                 160

Met Asn Gln Leu Leu Pro Gly Asn Ile Tyr Ala His Tyr Ala Trp Gly
            165                 170                 175

Ala Leu Phe Gly Val Cys Gln Ala Leu Pro Leu Leu His Val Met His
        180                 185                 190

Asp Ala Ser His Ala Ala Ile Thr Ser Ser Pro Thr Gly Trp Arg Leu
            195                 200                 205

Ile Gly Arg Leu Ala Met Asp Trp Val Ala Gly Ala Asn Met Val Ser
        210                 215                 220

Trp Leu Asn Gln His Val Val Gly His His Ile Tyr Thr Asn Val Ala
225                 230                 235                 240

Gly Ala Asp Pro Asp Leu Pro Val Asp Phe Lys Ser Asp Val Arg Arg
                245                 250                 255

Ile Val Tyr Arg Gln Val Leu Leu Pro Ile Tyr Lys Tyr Gln His Leu
            260                 265                 270

Tyr Leu Pro Pro Leu Tyr Gly Val Leu Gly Leu Lys Phe Arg Val Gln
        275                 280                 285

Asp Val Phe Glu Thr Phe Val Thr Leu Thr Asn Gly Pro Leu Arg Val
    290                 295                 300

Asn Pro Leu Ser Val Gly Asp Trp Ala Glu Met Ile Leu Ser Lys Ala
305                 310                 315                 320

Phe Trp Val Phe Tyr Arg Ile Tyr Leu Pro Leu Ala Val Leu Gln Val
                325                 330                 335

Asp Pro Ala Arg Phe Trp Gly Val Phe Leu Ala Glu Phe Ser Thr
            340                 345                 350

Gly Trp Tyr Leu Ala Phe Asn Phe Gln Val Ser His Val Ser Thr Ala
        355                 360                 365

Cys Glu Tyr Pro Gly Gly Asp Glu Val Thr Ser Ile Asp Asp Glu
    370                 375                 380

Trp Ala Ile Ser Gln Val Lys Ser Ser Val Asp Tyr Gly His Gly Ser
385                 390                 395                 400

Phe Ile Thr Thr Phe Leu Thr Gly Ala Leu Asn Tyr Gln Val Thr His
                405                 410                 415

His Leu Phe Pro Gly Val Ser Gln Tyr His Tyr Pro Ala Ile Ala Pro
            420                 425                 430

Leu Ile Leu Asp Val Cys His Lys Tyr Lys Val Lys Tyr Asn Val Leu
        435                 440                 445

Pro Asp Phe Thr Ala Ala Met Ala Gly His Phe Asp His Leu Val Ile
    450                 455                 460

Met Gly Lys Met Gly Lys Arg Val Thr Ile His Met Gly
465                 470                 475

<210> SEQ ID NO 14
<211> LENGTH: 469
<212> TYPE: PRT
<213> ORGANISM: Phaeodactylum tricornutum (GenBank Accession No.
      AAL92562)
<220> FEATURE:
<221> NAME/KEY: MISC_FEATURE
```

<223> OTHER INFORMATION: delta-5 desaturase

<400> SEQUENCE: 14

```
Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
    290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
    370                 375                 380

Gly Phe Leu Ser Gly Cys Phe Thr Gly Gly Leu Asn Phe Gln Val Glu
385                 390                 395                 400
```

```
His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465

<210> SEQ ID NO 15
<211> LENGTH: 467
<212> TYPE: PRT
<213> ORGANISM: Dictyostelium discoideum (GenBank Accession No.
      XP_640331)
<220> FEATURE:
<221> NAME/KEY: MISC_FEATURE
<223> OTHER INFORMATION: delta-5 desaturase

<400> SEQUENCE: 15

Met Met Glu Thr Asn Asn Glu Asn Lys Glu Lys Leu Lys Leu Tyr Thr
1               5                   10                  15

Trp Asp Glu Val Ser Lys His Asn Gln Lys Asn Asp Leu Trp Ile Ile
            20                  25                  30

Val Asp Gly Lys Val Tyr Asn Ile Thr Lys Trp Val Pro Leu His Pro
        35                  40                  45

Gly Gly Glu Asp Ile Leu Leu Leu Ser Ala Gly Arg Asp Ala Thr Asn
    50                  55                  60

Leu Phe Glu Ser Tyr His Pro Met Thr Asp Lys His Tyr Ser Leu Ile
65                  70                  75                  80

Lys Gln Tyr Glu Ile Gly Tyr Ile Ser Ser Tyr Glu His Pro Lys Tyr
                85                  90                  95

Val Glu Lys Ser Glu Phe Tyr Ser Thr Leu Lys Gln Arg Val Arg Lys
            100                 105                 110

His Phe Gln Thr Ser Ser Gln Asp Pro Lys Val Ser Val Gly Val Phe
        115                 120                 125

Thr Arg Met Val Leu Ile Tyr Leu Phe Leu Phe Val Thr Tyr Tyr Leu
    130                 135                 140

Ser Gln Phe Ser Thr Asp Arg Phe Trp Leu Asn Cys Ile Phe Ala Val
145                 150                 155                 160

Leu Tyr Gly Val Ala Asn Ser Leu Phe Gly Leu His Thr Met His Asp
                165                 170                 175

Ala Cys His Thr Ala Ile Thr His Asn Pro Met Thr Trp Lys Ile Leu
            180                 185                 190

Gly Ala Thr Phe Asp Leu Phe Ala Gly Ala Ser Phe Tyr Ala Trp Cys
        195                 200                 205

His Gln His Val Ile Gly His His Leu Tyr Thr Asn Val Arg Asn Ala
    210                 215                 220

Asp Pro Asp Leu Gly Gln Gly Glu Ile Asp Phe Arg Val Val Thr Pro
225                 230                 235                 240

Tyr Gln Ala Arg Ser Trp Tyr His Lys Tyr Gln His Ile Tyr Ala Pro
                245                 250                 255

Ile Leu Tyr Gly Val Tyr Ala Leu Lys Tyr Arg Ile Gln Asp His Glu
            260                 265                 270

Ile Phe Thr Lys Lys Ser Asn Gly Ala Ile Arg Tyr Ser Pro Ile Ser
```

```
                    275                 280                 285
Thr Ile Asp Thr Ala Ile Phe Ile Leu Gly Lys Leu Val Phe Ile Ile
    290                 295                 300

Ser Arg Phe Ile Leu Pro Leu Ile Tyr Asn His Ser Phe Ser His Leu
305                 310                 315                 320

Ile Cys Phe Phe Leu Ile Ser Glu Leu Val Leu Gly Trp Tyr Leu Ala
                325                 330                 335

Ile Ser Phe Gln Val Ser His Val Val Glu Asp Leu Gln Phe Met Ala
                340                 345                 350

Thr Pro Glu Ile Phe Asp Gly Ala Asp His Pro Leu Pro Thr Thr Phe
            355                 360                 365

Asn Gln Asp Trp Ala Ile Leu Gln Val Lys Thr Thr Gln Asp Tyr Ala
    370                 375                 380

Gln Asp Ser Val Leu Ser Thr Phe Phe Ser Gly Gly Leu Asn Leu Gln
385                 390                 395                 400

Val Ile His His Cys Phe Pro Thr Ile Ala Gln Asp Tyr Tyr Pro Gln
                405                 410                 415

Ile Val Pro Ile Leu Lys Glu Val Cys Lys Glu Tyr Asn Val Thr Tyr
                420                 425                 430

His Tyr Lys Pro Thr Phe Thr Glu Ala Ile Lys Ser His Ile Asn Tyr
            435                 440                 445

Leu Tyr Lys Met Gly Asn Asp Pro Asp Tyr Val Arg Lys Pro Val Asn
    450                 455                 460

Lys Asn Asp
465

<210> SEQ ID NO 16
<211> LENGTH: 421
<212> TYPE: PRT
<213> ORGANISM: Euglena gracilis
<220> FEATURE:
<221> NAME/KEY: MISC_FEATURE
<223> OTHER INFORMATION: delta-8 desaturase
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO2006012325
<311> PATENT FILING DATE: 2005-06-24
<312> PUBLICATION DATE: 2006-02-02
<313> RELEVANT RESIDUES: (1)..(421)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO2006012326
<311> PATENT FILING DATE: 2005-06-24
<312> PUBLICATION DATE: 2006-02-02
<313> RELEVANT RESIDUES: (1)..(421)

<400> SEQUENCE: 16

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
                20                  25                  30

Ile Glu Asn Tyr Gln Gly Arg Asp Ala Thr Asp Ala Phe Met Val Met
            35                  40                  45

His Ser Gln Glu Ala Phe Asp Lys Leu Lys Arg Met Pro Lys Ile Asn
        50                  55                  60

Pro Ser Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
```

```
                        85                  90                  95
Ala Ser Pro Leu Trp Tyr Ser Tyr Lys Ile Ser Thr Thr Leu Gly Leu
                100                 105                 110

Gly Val Leu Gly Tyr Phe Leu Met Val Gln Tyr Gln Met Tyr Phe Ile
            115                 120                 125

Gly Ala Val Leu Leu Gly Met His Tyr Gln Gln Met Gly Trp Leu Ser
        130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Phe Met Pro Ser Ile
        275                 280                 285

Leu Thr Ser Leu Leu Val Phe Phe Val Ser Glu Leu Val Gly Gly Phe
290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 17
<211> LENGTH: 1269
<212> TYPE: DNA
<213> ORGANISM: Pavlova lutheri CCMP459
<220> FEATURE:
<221> NAME/KEY: misc_feature
<223> OTHER INFORMATION: delta-8 desaturase

<400> SEQUENCE: 17
atgggcaagg gtggagacgg cggcgcgcag gcggtgagcg ggaccgacgc gtctctcgct      60
gaggtgagct ccgtcgatag caagagcgtg cacgtcgtgc tctacggcaa gcgcgtggat     120
```

-continued

```
gtcacaaagt tccagaaggc acacccgggc gggagcaagg tgttccgcat cttccaggag    180
cgcgacgcga cggagcagtt cgagtcttac cactcgccca aggccatcaa gatgatggag    240
ggcatgctca agaagtcgga ggatgcgccc gcttccgtgc ccctgccctc gcggtccacc    300
atgggcacgg agttcaagga gatgattgag cgccacaaga gggctggtct ctacgaccct    360
tgcccgttgg acgagctgtt caagctcacc atcgtccttg cgccatcttt cgtgggcgcc    420
tatctcgtgc ggagcggcgt ctcgcccctc gcgggcgcgc tctccatggg ctttggcttc    480
tacctcgacg gctggcttgc tcacgactac ctgcatcacg cagtcttcaa gggctcggtc    540
aacacgctcg tcaaggcgaa caacgccatg ggatacgccc tcggcttcct ccagggctac    600
gacgtggcct ggtggcgcgc gcgccataac acgcaccacg tgtgcaccaa cgaggatggt    660
tcggacccgg acatcaagac ggcgcccctg ctcatctacg tgcgagagaa cccgtccatt    720
gccaagcggc tcaacttctt ccagcgctgg cagcagtact actatgtgcc gaccatggcc    780
atcctcgacc tctactggcg cctggagtcc atcgcgtacg tggctgtgcg cctgcctaag    840
atgtggatgc aggccgccgc tcttgccgct cactacgcgc tcctgtgctg ggtcttcgca    900
gcgcatctca acctcatccc tctcatgatg gttgcacgcg gcttcgcgac gggcatcgtt    960
gtctttgcaa cccactatgg tgaggacatc ctcgaccgcg agcacgtcga gggcatgacg   1020
ctcgtcgagc agaccgccaa gacctcccgt aacatcacgg gcggctggct agtgaacgtg   1080
ctcacgggct tcatctccct gcagaccgag catcacctct tccccatgat gcccaccggc   1140
aacctaatga ctatccagcc cgaggtacgc gacttcttca gaagcatgg cctcgagtac    1200
cgcgagggca acctcttcca gtgcgtgcac cagaacatca aggctctcgc cttcgagcac   1260
ctcctccac                                                           1269
```

<210> SEQ ID NO 18
<211> LENGTH: 423
<212> TYPE: PRT
<213> ORGANISM: Pavlova lutheri CCMP459

<400> SEQUENCE: 18

```
Met Gly Lys Gly Gly Asp Gly Gly Ala Gln Ala Val Ser Gly Thr Asp
1               5                   10                  15

Ala Ser Leu Ala Glu Val Ser Ser Val Asp Ser Lys Ser Val His Val
            20                  25                  30

Val Leu Tyr Gly Lys Arg Val Asp Val Thr Lys Phe Gln Lys Ala His
        35                  40                  45

Pro Gly Gly Ser Lys Val Phe Arg Ile Phe Gln Glu Arg Asp Ala Thr
    50                  55                  60

Glu Gln Phe Glu Ser Tyr His Ser Pro Lys Ala Ile Lys Met Met Glu
65                  70                  75                  80

Gly Met Leu Lys Lys Ser Glu Asp Ala Pro Ala Ser Val Pro Leu Pro
                85                  90                  95

Ser Arg Ser Thr Met Gly Thr Glu Phe Lys Glu Met Ile Glu Arg His
            100                 105                 110

Lys Arg Ala Gly Leu Tyr Asp Pro Cys Pro Leu Asp Glu Leu Phe Lys
        115                 120                 125

Leu Thr Ile Val Leu Ala Pro Ile Phe Val Gly Ala Tyr Leu Val Arg
    130                 135                 140

Ser Gly Val Ser Pro Leu Ala Gly Ala Leu Ser Met Gly Phe Gly Phe
145                 150                 155                 160
```

```
Tyr Leu Asp Gly Trp Leu Ala His Asp Tyr Leu His His Ala Val Phe
            165                 170                 175

Lys Gly Ser Val Asn Thr Leu Val Lys Ala Asn Asn Ala Met Gly Tyr
            180                 185                 190

Ala Leu Gly Phe Leu Gln Gly Tyr Asp Val Ala Trp Trp Arg Ala Arg
            195                 200                 205

His Asn Thr His His Val Cys Thr Asn Glu Asp Gly Ser Asp Pro Asp
            210                 215                 220

Ile Lys Thr Ala Pro Leu Leu Ile Tyr Val Arg Glu Asn Pro Ser Ile
225                 230                 235                 240

Ala Lys Arg Leu Asn Phe Phe Gln Arg Trp Gln Gln Tyr Tyr Val
            245                 250                 255

Pro Thr Met Ala Ile Leu Asp Leu Tyr Trp Arg Leu Glu Ser Ile Ala
            260                 265                 270

Tyr Val Ala Val Arg Leu Pro Lys Met Trp Met Gln Ala Ala Leu
            275                 280                 285

Ala Ala His Tyr Ala Leu Leu Cys Trp Val Phe Ala Ala His Leu Asn
            290                 295                 300

Leu Ile Pro Leu Met Met Val Ala Arg Gly Phe Ala Thr Gly Ile Val
305                 310                 315                 320

Val Phe Ala Thr His Tyr Gly Glu Asp Ile Leu Asp Arg Glu His Val
            325                 330                 335

Glu Gly Met Thr Leu Val Glu Gln Thr Ala Lys Thr Ser Arg Asn Ile
            340                 345                 350

Thr Gly Gly Trp Leu Val Asn Val Leu Thr Gly Phe Ile Ser Leu Gln
            355                 360                 365

Thr Glu His His Leu Phe Pro Met Met Pro Thr Gly Asn Leu Met Thr
            370                 375                 380

Ile Gln Pro Glu Val Arg Asp Phe Phe Lys Lys His Gly Leu Glu Tyr
385                 390                 395                 400

Arg Glu Gly Asn Leu Phe Gln Cys Val His Gln Asn Ile Lys Ala Leu
            405                 410                 415

Ala Phe Glu His Leu Leu His
            420

<210> SEQ ID NO 19
<211> LENGTH: 7
<212> TYPE: PRT
<213> ORGANISM: Artificial Sequence
<220> FEATURE:
<223> OTHER INFORMATION: Conserved Region 1
<220> FEATURE:
<221> NAME/KEY: MISC_FEATURE
<222> LOCATION: (4)..(4)
<223> OTHER INFORMATION: Xaa = Ile or Val

<400> SEQUENCE: 19

Gly His His Xaa Tyr Thr Asn
1               5

<210> SEQ ID NO 20
<211> LENGTH: 7
<212> TYPE: PRT
<213> ORGANISM: Artificial Sequence
<220> FEATURE:
<223> OTHER INFORMATION: Conserved Region 2
<220> FEATURE:
<221> NAME/KEY: MISC_FEATURE
<222> LOCATION: (4)..(4)
<223> OTHER INFORMATION: Xaa = Val or Ala
```

```
<220> FEATURE:
<221> NAME/KEY: MISC_FEATURE
<222> LOCATION: (5)..(5)
<223> OTHER INFORMATION: Xaa = Ser or Asn

<400> SEQUENCE: 20

Asn Phe Gln Xaa Xaa His Val
1               5

<210> SEQ ID NO 21
<211> LENGTH: 476
<212> TYPE: PRT
<213> ORGANISM: Thalassiosira pseudonana (GenBank Accession No.
      AAX14502)
<220> FEATURE:
<221> NAME/KEY: MISC_FEATURE
<223> OTHER INFORMATION: delta-8 desaturase

<400> SEQUENCE: 21

Met Pro Pro Asn Ala Asp Ile Ser Arg Ile Arg Asn Arg Ile Pro Thr
1               5                   10                  15

Lys Thr Gly Thr Val Ala Ser Ala Asp Asn Asn Asp Pro Ala Thr Gln
            20                  25                  30

Ser Val Arg Thr Leu Lys Ser Leu Lys Gly Asn Glu Val Val Ile Asn
        35                  40                  45

Gly Thr Ile Tyr Asp Ile Ala Asp Phe Val His Pro Gly Gly Glu Val
    50                  55                  60

Val Lys Phe Phe Gly Gly Asn Asp Val Thr Ile Gln Tyr Asn Met Ile
65                  70                  75                  80

His Pro Tyr His Thr Gly Lys His Leu Glu Lys Met Lys Ala Val Gly
                85                  90                  95

Lys Val Val Asp Trp Gln Ser Asp Tyr Lys Phe Asp Thr Pro Phe Glu
            100                 105                 110

Arg Glu Ile Lys Ser Glu Val Phe Lys Ile Val Arg Arg Gly Arg Glu
        115                 120                 125

Phe Gly Thr Thr Gly Tyr Phe Leu Arg Ala Phe Phe Tyr Ile Ala Leu
    130                 135                 140

Phe Phe Thr Met Gln Tyr Thr Phe Ala Thr Cys Thr Thr Phe Thr Thr
145                 150                 155                 160

Tyr Asp His Trp Tyr Gln Ser Gly Val Phe Ile Ala Ile Val Phe Gly
                165                 170                 175

Ile Ser Gln Ala Phe Ile Gly Leu Asn Val Gln His Asp Ala Asn His
            180                 185                 190

Gly Ala Ala Ser Lys Arg Pro Trp Val Asn Asp Leu Leu Gly Phe Gly
        195                 200                 205

Thr Asp Leu Ile Gly Ser Asn Lys Trp Asn Trp Met Ala Gln His Trp
    210                 215                 220

Thr His His Ala Tyr Thr Asn His Ser Glu Lys Asp Pro Asp Ser Phe
225                 230                 235                 240

Ser Ser Glu Pro Met Phe Ala Phe Asn Asp Tyr Pro Ile Gly His Pro
                245                 250                 255

Lys Arg Lys Trp Trp His Arg Phe Gln Gly Gly Tyr Phe Leu Phe Met
            260                 265                 270

Leu Gly Leu Tyr Trp Leu Pro Thr Val Phe Asn Pro Gln Phe Ile Asp
        275                 280                 285

Leu Arg Gln Arg Gly Ala Gln Tyr Val Gly Ile Gln Met Glu Asn Asp
    290                 295                 300
```

```
Phe Ile Val Lys Arg Arg Lys Tyr Ala Val Ala Leu Arg Met Met Tyr
305                 310                 315                 320
Ile Tyr Leu Asn Ile Val Ser Pro Phe Met Asn Asn Gly Leu Ser Trp
            325                 330                 335
Ser Thr Phe Gly Ile Ile Met Leu Met Gly Ile Ser Glu Ser Leu Thr
        340                 345                 350
Leu Ser Val Leu Phe Ser Leu Ser His Asn Phe Ile Asn Ser Asp Arg
    355                 360                 365
Asp Pro Thr Ala Asp Phe Lys Lys Thr Gly Glu Gln Val Cys Trp Phe
370                 375                 380
Lys Ser Gln Val Glu Thr Ser Ser Thr Tyr Gly Gly Phe Ile Ser Gly
385                 390                 395                 400
Cys Leu Thr Gly Gly Leu Asn Phe Gln Val Glu His His Leu Phe Pro
                405                 410                 415
Arg Met Ser Ser Ala Trp Tyr Pro Tyr Ile Ala Pro Thr Val Arg Glu
            420                 425                 430
Val Cys Lys Lys His Gly Met Ser Tyr Ala Tyr Tyr Pro Trp Ile Gly
        435                 440                 445
Gln Asn Leu Val Ser Thr Phe Lys Tyr Met His Arg Ala Gly Ser Gly
    450                 455                 460
Ala Asn Trp Glu Leu Lys Pro Leu Ser Gly Ser Ala
465                 470                 475

<210> SEQ ID NO 22
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 22
gtacgagccg gaagcataaa gtgtaaagcc tggggtgcct aatgagtgag ctaactcaca      60
ttaattgcgt tgcgctcact gcccgctttc cagtcgggaa acctgtcgtg ccagctgcat     120
taatgaatcg gccaacgcgc ggggagaggc ggtttgcgta ttgggcgctc ttccgcttcc     180
tcgctcactg actcgctgcg ctcggtcgtt cggctgcggc gagcggtatc agctcactca     240
aaggcggtaa tacggttatc cacagaatca ggggataacg caggaaagaa catgtgagca     300
aaaggccagc aaaaggccag gaaccgtaaa aaggccgcgt tgctggcgtt tttccatagg     360
ctccgccccc ctgacgagca tcacaaaaat cgacgctcaa gtcagaggtg gcgaaacccg     420
acaggactat aaagatacca ggcgtttccc cctggaagct ccctcgtgcg ctctcctgtt     480
ccgaccctgc cgcttaccgg atacctgtcc gcctttctcc cttcgggaag cgtggcgctt     540
tctcatagct cacgctgtag gtatctcagt tcggtgtagg tcgttcgctc caagctgggc     600
tgtgtgcacg aaccccccgt tcagcccgac cgctgcgcct tatccggtaa ctatcgtctt     660
gagtccaacc cggtaagaca cgacttatcg ccactggcag cagccactgg taacaggatt     720
agcagagcga ggtatgtagg cggtgctaca gagttcttga agtggtggcc taactacggc     780
tacactagaa ggacagtatt tggtatctgc gctctgctga agccagttac cttcggaaaa     840
agagttggta gctcttgatc cggcaaacaa accaccgctg gtagcggtgg tttttttgtt     900
tgcaagcagc agattacgcg cagaaaaaaa ggatctcaag aagatccttt gatcttttct     960
acggggtctg acgctcagtg gaacgaaaac tcacgttaag ggattttggt catgagatta    1020
tcaaaaagga tcttcaccta gatcctttta aattaaaaat gaagttttaa atcaatctaa    1080
```

```
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agcccacgc    1260 tcaccggctc cagatttatc agcaataaac cagccagccg aagggccga gcgcagaagt    1320 ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaataaaaca aatagggatt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tattttattt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
```

```
agtcatttca tcccacatat tccttggatt tctctccaat gaatgacatt ctatcttgca   3540
aattcaacaa ttataataag ataccaaa gtagcggtat agtggcaatc aaaaagcttc     3600
tctggtgtgc ttctcgtatt tattttatt ctaatgatcc attaaaggta tatatttatt   3660
tcttgttata taatcctttt gtttattaca tgggctggat acataaaggt attttgattt   3720
aattttttgc ttaaattcaa tcccccctcg ttcagtgtca actgtaatgg taggaaatta   3780
ccatactttt gaagaagcaa aaaaatgaa agaaaaaaaa aatcgtattt ccaggttaga    3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttacttt agcttatgca   4140 tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccacccg ggggtcagaa taagccagtc    4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcgtg acaccggtac tggtgcttga cagtgttgcc    5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg gggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgcccggag aagacggcca    5820
```

```
ggccgcctag atgacaaatt caacaactca cagctgactt tctgccattg ccactagggg    5880 ggggccttttt tatatggcca agccaagctc tccacgtcgg ttgggctgca cccaacaata    5940
aatgggtagg gttgcaccaa caaagggatg ggatgggggg tagaagatac gaggataacg    6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagaggt tccgagcact ttaggttgca ccaaatgtcc caccaggtgc aggcagaaaa    6180
cgctggaaca gcgtgtacag tttgtcttaa caaaagtga gggcgctgag gtcgagcagg    6240
gtggtgtgac ttgttatagc ctttagagct gcgaaagcgc gtatggattt ggctcatcag    6300
gccagattga gggtctgtgg acacatgtca tgttagtgta cttcaatcgc ccctggata    6360 tagccccgac aataggccgt ggcctcattt ttttgccttc cgcacatttc cattgctcgg    6420
tacccacacc ttgcttctcc tgcacttgcc aaccttaata ctggtttaca ttgaccaaca    6480
tcttacaagc ggggggcttg tctagggtat atataaacag tggctctccc aatcggttgc    6540
cagtctcttt tttcctttct ttccccacag attcgaaatc taaactacac atcacacaat    6600
gcctgttact gacgtcctta agcgaaagtc cggtgtcatc gtcggcgacg atgtccgagc    6660
cgtgagtatc cacgacaaga tcagtgtcga gacgacgcgt tttgtgtaat gacacaatcc    6720
gaaagtcgct agcaacacac actctctaca caaactaacc cagctctcca tggctgagga    6780
taagaccaag gtcgagttcc ctaccctgac tgagctgaag cactctatcc ctaacgcttg    6840
ctttgagtcc aacctcggac tctcgctcta ctacactgcc cgagcgatct tcaacgcatc    6900
tgcctctgct gctctgctct acgctgcccg atctactccc ttcattgccg ataacgttct    6960
gctccacgct ctggtttgcg ccacctacat ctacgtgcag ggtgtcatct tctgggggttt    7020 ctttaccgtc ggtcacgact gtggtcactc tgccttctcc cgataccact ccgtcaactt    7080
catcattggc tgcatcatgc actctgccat tctgactccc ttcgagtcct ggcgagtgac    7140
ccaccgacac catcacaaga acactggcaa cattgataag gacgagatct tctaccctca    7200
tcggtccgtc aaggacctcc aggacgtgcg acaatgggtc tacaccctcg gaggtgcttg    7260
gtttgtctac ctgaaggtcg gatatgctcc tcgaaccatg tcccactttg accctggga    7320 ccctctcctg cttcgacgag cctccgctgt catcgtgtcc ctcggagtct gggctgcctt    7380
cttcgctgcc tacgcctacc tcacatactc gctcggcttt gccgtcatgg gcctctacta    7440
ctatgctcct ctctttgtct ttgcttcgtt cctcgtcatt actaccttct tgcatcacaa    7500
cgacgaagct actccctggt acggtgactc ggagtggacc tacgtcaagg gcaacctgag    7560
ctccgtcgac cgatcgtacg gagctttcgt ggacaacctg tctcaccaca ttggcaccca    7620
ccaggtccat cacttgttcc ctatcattcc ccactacaag ctcaacgaag ccaccaagca    7680
ctttgctgcc gcttaccctc acctcgtgag acgtaacgac gagcccatca ttactgcctt    7740
cttcaagacc gctcacctct ttgtcaacta cggagctgtg cccgagactg ctcagatttt    7800
caccctcaaa gagtctgccg ctgcagccaa ggccaagagc gactaagcgg ccgcaagtgt    7860
ggatggggaa gtgagtgccc ggttctgtgt gcacaattgg caatccaaga tggatggatt    7920
caacacaggg atatagcgag ctacgtggtg gtgcgaggat atagcaacgg atatttatgt    7980
ttgacacttg agaatgtacg atacaagcac tgtccaagta caatactaaa catactgtac    8040
atactcatac tcgtacccgg gcaacggttt cacttgagtg cagtggctag tgctcttact    8100
cgtacagtgt gcaatactgc gtatcatagt ctttgatgta tatcgtattc attcatgtta    8160
gttgc                                                                8165
```

<210> SEQ ID NO 23
<211> LENGTH: 8480
<212> TYPE: DNA
<213> ORGANISM: Artificial Sequence
<220> FEATURE:
<223> OTHER INFORMATION: Plasmid pDMW368

<400> SEQUENCE: 23

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca caaaaatcga cgctcaagtc     720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac cccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg gggtctgacg ctcagtggaa cgaaaactca cgttaaggga    1320
ttttggtcat gagattatca aaaggatct cacctagat cctttttaaat taaaaatgaa    1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt cgcaacgtt gttgccattg    1740
ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
```

```
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttccttttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cgggggctcc    2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaattta acaaaatatt aacgcttaca atttccattc    2880
gccattcagg ctgcgcaact gttgggaagg gcgatcggtg cgggcctctt cgctattacg    2940
ccagctggcg aaaggggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg ctggatacaa    4020
taaaggtatt ttgatttaat tttttgctta aattcaatcc cccctcgttc agtgtcaact    4080
gtaatggtag gaaattacca tacttttgaa gaagcaaaaa aatgaaaga aaaaaaaat    4140 cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg ttttttttg    4320 tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
```

```
tactttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcgcaag ctcaatgagc    5520
tccttggtgg tggtaacatc cagagaagca cacaggttgg ttttcttggc tgccacgagc    5580
ttgagcactc gagcggcaaa gcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgactcag gcgacgacgg aattcctgca gcccatctgc    6060
agaattcagg agagaccggg ttggcggcgt atttgtgtcc caaaaaacag ccccaattgc    6120
cccggagaag acggccaggc cgcctagatg acaaattcaa caactcacag ctgactttct    6180
gccattgcca ctaggggggg gccttttat atggccaagc caagctctcc acgtcggttg    6240
ggctgcaccc aacaataaat gggtagggtt gcaccaacaa agggatggga tgggggtag    6300
aagatacgag gataacgggg ctcaatggca caaataagaa cgaatactgc cattaagact    6360
cgtgatccag cgactgacac cattgcatca tctaagggcc tcaaaactac ctcggaactg    6420
ctgcgctgat ctggacacca cagaggttcc gagcacttta ggttgcacca aatgtcccac    6480
caggtgcagg cagaaaacgc tggaacagcg tgtacagttt gtcttaacaa aaagtgaggg    6540
cgctgaggtc gagcagggtg gtgtgacttg ttatagcctt tagagctgcg aaagcgcgta    6600
tggatttggc tcatcaggcc agattgaggg tctgtggaca catgtcatgt tagtgtactt    6660
caatcgcccc ctggatatag ccccgacaat aggccgtggc ctcatttttt tgccttccgc    6720
acatttccat tgctcggtac ccacaccttg cttctcctgc acttgccaac cttaatactg    6780
```

| | |
|---|---|
| gtttacattg accaacatct acaagcggg gggcttgtct agggtatata taaacagtgg | 6840 |
| ctctcccaat cggttgccag tctcttttt cctttcttc cccacagatt cgaaatctaa | 6900 |
| actacacatc acacaatgcc tgttactgac gtccttaagc gaaagtccgg tgtcatcgtc | 6960 |
| ggcgacgatg tccgagccgt gagtatccac gacaagatca gtgtcgagac gacgcgtttt | 7020 |
| gtgtaatgac acaatccgaa agtcgctagc aacacacact ctctacacaa actaacccag | 7080 |
| ctctccatgg ctccagatgc ggacaagttg agacagcgca aggcgcaatc gattcaagac | 7140 |
| acggctgatt cgcaagctac cgaactcaag attggcaccc tgaagggctt gcaggggaca | 7200 |
| gaaatcgtca ttgatggaga catttacgat ataaaagact ttgatcaccc cggtggtgaa | 7260 |
| tccatcatga cttttggggg aaacgatgtc accgccacgt acaagatgat ccaccccta c | 7320 |
| cactctaagc accatttgga gaagatgaag aaagtgggac gagttccgga ctacacctcg | 7380 |
| gaatacaagt ttgatactcc ctttgagcgt gaaatcaagc aagaggtctt caagattgtg | 7440 |
| cgacgaggcc gcgagtttgg aacacctgga tacttcttcc gggctttctg ctacattgga | 7500 |
| cttttctttt acttgcagta tttgtgggtc acgactccca ctacctttgc cttggcgatc | 7560 |
| ttctatggtg tttcgcaagc tttcattggt ttgaacgtac aacatgatgc caaccacgga | 7620 |
| gctgcctcca agaagccttg gatcaataac ttgctaggat tggggctga ctttatcgga | 7680 |
| ggttccaaat ggttgtggat gaaccagcac tggacgcacc acacatacac caaccaccat | 7740 |
| gagaaggatc ccgatgcctt gggcgctgaa ccaatgttgt tgttcaatga ttatcccttg | 7800 |
| ggtcacccaa agcgtacttt gattcaccac ttccaggcct tctattacct tttcgtcttg | 7860 |
| gccggatact gggtctcttc ggtcttcaac cctcaaattt tggacttgca acaccgcggt | 7920 |
| gctcaagcgg ttggaatgaa aatggagaac gattacattg ccaaaagccg aaagtatgcc | 7980 |
| atcttcttgc gtctcttgta tatttacacc aacattgtcg ctccgatcca aaaccaaggc | 8040 |
| ttctcgttga ccgtggtcgc ccacattttg accatgggcg tcgcttccag tttgactttg | 8100 |
| gcgactcttt ttgccttgtc gcacaatttt gaaaacgcgg atcgcgatcc cacttacgag | 8160 |
| gcccgcaagg gaggagagcc tgtttgttgg ttcaagtcgc aagtcgaaac ctcgtcaact | 8220 |
| tacggaggtt tcatctcggg ttgcttgacg ggcggactca acttccaagt ggaacaccac | 8280 |
| ttgttccctc gtatgagttc ggcctggtac ccctacattg cccctactgt tcgagaggtt | 8340 |
| tgcaaaaagc acggagtcaa gtacgcatac tatccctggg tctggcaaaa cttgatttca | 8400 |
| actgtcaagt atctgcatca aagcggaact ggatccaact ggaagaatgg cgccaaccc c | 8460 |
| tactcgggaa aattgtaagc | 8480 |

```
<210> SEQ ID NO 24
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 24
```

| | |
|---|---|
| taaccctcac taagggaac aaaagctgga gctccaccgc ggacacaata tctggtcaaa | 60 |
| tttcagtttc gttacataaa tcgttatgtc aaaggagtgt gggaggttaa gagaattatc | 120 |

```
accggcaaac tatctgttaa ttgctaggta cctctagacg tccacccggg tcgcttggcg    180
gccgaagagg ccggaatctc gggccgcggt ggcggccgct tagttggtct tggacttctt    240
gggcttcttc aggtaggact ggacaaagaa gttgccgaac agagcgagca gggtgatcat    300
gtacacgccg agcagctgga ccagagcctg agggtagtcg caggggaaga ggtagtcgta    360
cagggactgc accagcatag ccatgaactg ggtcatctgc agagtggtga tgtagggctt    420
gatgggcttg acgaagccga agccctgaga ggaaaagaag tagtaggcgt acatgacggt    480
gtggacgaag gagttgagga tgacggagaa gtaggcgtcg ccaccaggag cgtacttggc    540
aatagcccac cagatggcga agatggtggc atggtggtac acgtgcagga aggagacctg    600
gttgaacttc ttgcacagga tcatgatagc ggtgtccagg aactcgtagg ccttggagac    660
gtagaacacg tagacgattc gggacatgcc ctgagcgtgg gactcgttgc ccttctccat    720
gtcgttgccg aagaccttgt agccacccag gatagcctgt cggatggtct cgacgcacat    780
gtagagggac agtccgaaga ggaacaggtt gtggagcagc ttgatggtct tcagctcgaa    840
gggcttctcc atctgcttca tgatgggaat gccgaagagc agcatggcca tgtagccgac    900
ctcgaaggcg agcatggtgg agacgtccat catgggcaga ccgtcggtca gagcgtaggg    960
cttagctccg tccatccact ggtcgacacc ggtctcgact cgtccgacca cgtcgtccca    1020
gacagaggag ttggccatgg tgaatgattc ttatactcag aaggaaatgc ttaacgattt    1080
cgggtgtgag ttgacaagga gagagagaaa agaagaggaa aggtaattcg gggacggtgg    1140
tcttttatac ccttggctaa agtcccaacc acaaagcaaa aaaatttttca gtagtctatt    1200
ttgcgtccgg catgggttac ccggatggcc agacaaagaa actagtacaa agtctgaaca    1260
agcgtagatt ccagactgca gtaccctacg cccttaacgg caagtgtggg aaccggggga    1320
ggtttgatat gtggggtgaa gggggctctc gccggggttg ggcccgctac tgggtcaatt    1380
tggggtcaat tggggcaatt ggggctgttt tttgggacac aaatacgccg ccaacccggt    1440
ctctcctgaa ttctgcatcg atcgaggaag aggacaagcg gctgcttctt aagtttgtga    1500
catcagtatc caaggcacca ttgcaaggat tcaaggcttt gaacccgtca tttgccattc    1560
gtaacgctgg tagacaggtt gatcggttcc ctacggcctc cacctgtgtc aatcttctca    1620
agctgcctga ctatcaggac attgatcaac ttcggaagaa actttttgtat gccattcgat    1680
cacatgctgg tttcgatttg tcttagagga acgcatatac agtaatcata gagaataaac    1740
gatattcatt tattaaagta gatagttgag gtagaagttg taaagagtga taaatagcgg    1800
ccgcgcctac ttaagcaacg ggcttgataa cagcgggggg ggtgcccacg ttgttgcggt    1860
tgcggaagaa cagaacaccc ttaccagcac cctcggcacc agcgctgggc tcaacccact    1920
ggcacatacg cgcactgcgg tacatggcgc ggatgaagcc acgaggacca tcctggacat    1980
cagcccggta gtgcttgccc atgatgggct taatggcctc ggtggcctcg tccgcgttgt    2040
agaaggggat gctgctgacg tagtggtgga ggacatgagt ctcgatgatg ccgtggagaa    2100
ggtggcggcc gatgaagccc atctcacggt caatggtagc agcggcacca cggacgaagt    2160
tccactcgtc gttggtgtag tggggaaggg tagggtcggt gtgctggagg aaggtgatgg    2220
caacgagcca gtggttaacc cagaggtagg gaacaaagta ccagatggcc atgttgtaga    2280
aaccgaactt ctgaacgagg aagtacagag cagtggccat cagaccgata ccaatatcgc    2340
tgaggacgat gagcttagcg tcactgttct cgtacagagg gctgcgggga tcgaagtggt    2400
taacaccacc gccgaggccg ttatgcttgc ccttgccgcg accctcacgc tggcgctcgt    2460
```

```
ggtagttgtg gccggtaaca ttggtgatga ggtagttggg ccagccnacg annnnctcag    2520
taagatgagc gagctcgtgg gtcatctttc cgagacgagt agcctgctgc tcgcgggttc    2580
ggggaacgaa gaccatgtca cgctccatgt tgccagtggc cttgtggtgc tttcggtggg    2640
agatttgcca gctgaagtag gggacaagga gggaagagtg aagaacccag ccagtaatgt    2700
cgttgatgat gcgagaatcg gagaaagcac cgtgaccgca ctcatgggca ataacccaga    2760
gaccagtacc gaaaagaccc tgaagaacgg tgtacacggc ccacagacca gcgcgggcgg    2820
gggtggaggg gatatattcg ggggtcacaa agttgtacca gatgctgaaa gtggtagtca    2880
ggaggacaat gtcgcggagg atataaccgt atcccttgag agcggagcgc ttgaagcagt    2940
gcttagggat ggcattgtag atgtccttga tggtaaagtc gggaacctcg aactggttgc    3000
cgtaggtgtc gagcatgaca ccatactcgg acttgggctt ggcgtatatca acctcggaca    3060 tggacgagag cgatgtggaa gaggccgagt ggcgggggaga gtctgaagga gagacggcgg    3120
cagactcaga atccgtcaca gtagttgagg tgacggtgcg tctaagcgca gggttctgct    3180
tgggcagagc cgaagtggac gccatggaga gctgggttag tttgtgtaga gagtgtgtgt    3240
tgctagcgac tttcggattg tgtcattaca caaaacgcgt cgtctcgaca ctgatcttgt    3300
cgtggatact cacggctcgg acatcgtcgc cgacgatgac accggacttt cgcttaagga    3360
cgtcagtaac aggcattgtg tgatgtgtag tttagatttc gaatctgtgg ggaaagaaag    3420 gaaaaagag actggcaacc gattgggaga gccactgttt atatataccc tagacaagcc    3480
ccccgcttgt aagatgttgg tcaatgtaaa ccagtattaa ggttggcaag tgcaggagaa    3540
gcaaggtgtg ggtaccgagc aatggaaatg tgcggaaggc aaaaaaatga ggccacggcc    3600
tattgtcggg gctatatcca gggggcgatt gaagtacact aacatgacat gtgtccacag    3660
accctcaatc tggcctgatg agccaaatcc atacgcgctt tcgcagctct aaaggctata    3720
acaagtcaca ccaccctgct cgacctcagc gccctcactt tttgttaaga caaactgtac    3780
acgctgttcc agcgttttct gcctgcacct ggtgggacat ttggtgcaac ctaaagtgct    3840
cggaacctct gtggtgtcca gatcagcgca gcagttccga ggtagttttg aggcccttag    3900
atgatgcaat ggtgtcagtc gctggatcac gagtcttaat ggcagtattc gttcttattt    3960
gtgccattga gccccgttat cctcgtatct tctacccccc atcccatccc tttgttggtg    4020
caaccctacc catttattgt tgggtgcagc ccaaccgacg tggagagctt ggcttggcca    4080
tataaaaagg cccccccta gtggcaatgg cagaaagtca gctgtgagtt gttgaatttg    4140
tcatctaggc ggcctggccg tcttctccgg ggcaattgtt cctctatagt actgcgtaca    4200
ctgtttaaac agtgtacgca gatctgcgac gacggaattc ctgcagccca tctgcagaat    4260
tcaggagaga ccgggttggc ggcgtatttg tgtcccaaaa aacagcccca attgccccaa    4320
ttgaccccaa attgacccag tagcgggccc aaccccggcg agagccccct tcacccccaca    4380 tatcaaacct ccccggttc ccacacttgc cgttaagggc gtagggtact gcagtctgga    4440
atctacgctt gttcagactt tgtactagtt tctttgtctg gccatccggg taacccatgc    4500
cggacgcaaa atagactact gaaaattttt ttgctttgtg gttgggactt tagccaaggg    4560
tataaaagac caccgtcccc gaattacctt tcctcttctt ttctctctct ccttgtcaac    4620
tcacacccga aatcgttaag catttccttc tgagtataag aatcattcac catgctgcc    4680 gctccctctg tgcgaacctt tacccgagcc gaggttctga acgctgaggc tctgaacgag    4740
ggcaagaagg acgctgaggc tcccttcctg atgatcatcg acaacaaggt gtacgacgtc    4800
cgagagttcg tccctgacca tcctggaggc tccgtgattc tcacccacgt tggcaaggac    4860
```

```
ggcaccgacg tctttgacac ctttcatccc gaggctgctt gggagactct cgccaacttc   4920
tacgttggag acattgacga gtccgaccga gacatcaaga acgatgactt tgccgctgag   4980
gtccgaaagc tgcgaaccct gttccagtct ctcggctact acgactcctc taaggcctac   5040
tacgccttca aggtctcctt caacctctgc atctgggac tgtccaccgt cattgtggcc    5100
aagtggggtc agacctccac cctcgccaac gtgctctctg ctgccctgct cggcctgttc   5160
tggcagcagt gcggatggct ggctcacgac tttctgcacc accaggtctt ccaggaccga   5220
ttctggggtg atctcttcgg agccttcctg ggaggtgtct gccagggctt ctcctcttcc   5280
tggtggaagg acaagcacaa cactcaccat gccgctccca acgtgcatgg cgaggatcct   5340
gacattgaca cccacccctct cctgacctgg tccgagcacg ctctggagat gttctccgac   5400
gtccccgatg aggagctgac ccgaatgtgg tctcgattca tggtcctgaa ccagacctgg   5460
ttctacttcc ccattctctc cttcgctcga ctgtcttggt gcctccagtc cattctcttt   5520
gtgctgccca acggtcaggc tcacaagccc tccggagctc gagtgcccat ctccctggtc   5580
gagcagctgt ccctcgccat gcactggacc tggtacctcg ctaccatgtt cctgttcatc   5640
aaggatcctg tcaacatgct cgtgtacttc ctggtgtctc aggctgtgtg cggaaacctg   5700
ctcgccatcg tgttctccct caaccacaac ggtatgcctg tgatctccaa ggaggaggct   5760
gtcgacatgg atttctttac caagcagatc atcactggtc gagatgtcca tcctggactg   5820
ttcgccaact ggttcaccgg tggcctgaac taccagatcg agcatcacct gttcccttcc   5880
atgcctcgac acaacttctc caagatccag cctgccgtcg agaccctgtg caagaagtac   5940
aacgtccgat accacaccac tggtatgatc gagggaactg ccgaggtctt ctcccgactg   6000
aacgaggtct ccaaggccac ctccaagatg gcaaggctc agtaagcggc cgcatgagaa    6060
gataaatata taaatacatt gagatattaa atgcgctaga ttagagagcc tcatactgct   6120
cggagagaag ccaagacgag tactcaaagg ggattacacc atccatatcc acagacacaa   6180
gctggggaaa ggttctatat acactttccg gaataccgta gtttccgatg ttatcaatgg   6240
gggcagccag gatttcaggc acttcggtgt ctcggggtga aatggcgttc ttggcctcca   6300
tcaagtcgta ccatgtcttc atttgcctgt caaagtaaaa cagaagcaga tgaagaatga   6360
acttgaagtg aaggaattta aattgccccg gagaagacgg ccaggccgcc tagatgacaa   6420
attcaacaac tcacagctga cttttctgcca ttgccactag ggggggggcct ttttatatgg   6480 ccaagccaag ctctccacgt cggttgggct gcacccaaca ataaatgggt agggttgcac   6540
caacaaaggg atgggatggg gggtagaaga tacgaggata acggggctca atggcacaaa   6600
taagaacgaa tactgccatt aagactcgtg atccagcgac tgacaccatt gcatcatcta   6660
agggcctcaa aactacctcg gaactgctgc gctgatctgg acaccacaga ggttccgagc   6720
actttaggtt gcaccaaatg tcccaccagg tgcaggcaga aaacgctgga acagcgtgta   6780
cagtttgtct taacaaaaag tgagggcgct gaggtcgagc agggtggtgt gacttgttat   6840
agcctttaga gctgcgaaag cgcgtatgga tttggctcat caggccagat tgagggtctg   6900
tggacacatg tcatgttagt gtacttcaat cgcccctgg atatagcccc gacaataggc     6960
cgtggcctca tttttttgcc ttccgcacat ttccattgct cggtacccac accttgcttc   7020
tcctgcactt gccaacctta atactggttt acattgacca acatcttaca agcgggggc    7080 ttgtctaggg tatatataaa cagtggctct cccaatcggt tgccagtctc ttttttcctt   7140 tctttccccca cagattcgaa atctaaacta cacatcacac aatgcctgtt actgacgtcc   7200
```

```
ttaagcgaaa gtccggtgtc atcgtcggcg acgatgtccg agccgtgagt atccacgaca    7260
agatcagtgt cgagacgacg cgttttgtgt aatgacacaa tccgaaagtc gctagcaaca    7320
cacactctct acacaaacta acccagctct ccatggagtc cattgctccc ttcctgccct    7380
ccaagatgcc tcaggacctg ttcatggacc tcgccagcgc tatcggtgtc cgagctgctc    7440
cctacgtcga tcccctggag gctgccctgg ttgcccaggc cgagaagtac attcccacca    7500
ttgtccatca cactcgaggc ttcctggttg ccgtggagtc tccccctggct cgagagctgc    7560
ctctgatgaa cccettccac gtgctcctga tcgtgctcgc ctacctggtc accgtgtttg    7620
tgggtatgca gatcatgaag aactttgaac gattcgaggt caagaccttc tccctcctgc    7680
acaacttctg tctggtctcc atctccgcct acatgtgcgg tggcatcctg tacgaggctt    7740
atcaggccaa ctatggactg tttgagaacg ctgccgatca caccttcaag ggtctcccta    7800
tggctaagat gatctggctc ttctacttct ccaagatcat ggagtttgtc gacaccatga    7860
tcatggtcct caagaagaac aaccgacaga tttcctttct gcacgtgtac caccactctt    7920
ccatcttcac catctggtgg ctggtcacct tcgttgctcc caacggtgaa gcctacttct    7980
ctgctgccct gaactccttc atccacgtca tcatgtacgg ctactacttt ctgtctgccc    8040
tgggcttcaa gcaggtgtcg ttcatcaagt tctacatcac tcgatcccag atgacccagt    8100
tctgcatgat gtctgtccag tcttcctggg acatgtacgc catgaaggtc cttggccgac    8160
ctggataccc cttcttcatc accgctctgc tctggttcta catgtggacc atgctcggtc    8220
tcttctacaa cttttaccga aagaacgcca agctcgccaa gcaggccaag gctgacgctg    8280
ccaaggagaa ggccagaaag ctccagtaag cggccgcaag tgtggatggg gaagtgagtg    8340
cccggttctg tgtgcacaat tggcaatcca agatggatgg attcaacaca gggatatagc    8400
gagctacgtg gtggtgcgag gatatagcaa cggatattta tgtttgacac ttgagaatgt    8460
acgatacaag cactgtccaa gtacaatact aaacatactg tacatactca tactcgtacc    8520
cgggcaacgg tttcacttga gtgcagtggc tagtgctctt actcgtacag tgtgcaatac    8580
tgcgtatcat agtctttgat gtatatcgta ttcattcatg ttagttgcgt acgaagtcgt    8640
caatgatgtc gatatggagtt tgatcatgc acacataagg tccgaccttta tcggcaagct    8700
caatgagctc cttggtggtg gtaacatcca gagaagcaca caggttggtt ttcttggctg    8760
ccacgagctt gagcactcga gcggcaaagg cggacttgtg gacgttagct cgagcttcgt    8820
aggagggcat tttggtggtg aagaggagac tgaaataaat ttagtctgca gaactttta    8880
tcggaacctt atctggggca gtgaagtata tgttatggta atagttacga gttagttgaa    8940
cttatagata gactggacta tacggctatc ggtccaaatt agaaagaacg tcaatggctc    9000
tctgggcgtc gcctttgccg acaaaaatgt gatcatgatg aaagccagca atgacgttgc    9060
agctgatatt gttgtcggcc aaccgcgccg aaaacgcagc tgtcagaccc acagcctcca    9120
acgaagaatg tatcgtcaaa gtgatccaag cacactcata gttggagtcg tactccaaag    9180
gcggcaatga cgagtcagac agatactcgt cgacctttc cttgggaacc accaccgtca    9240
gcccttctga ctcacgtatt gtagccaccg acacaggcaa cagtccgtgg atagcagaat    9300
atgtcttgtc ggtccatttc tcaccaactt taggcgtcaa gtgaatgttg cagaagaagt    9360
atgtgccttc attgagaatc ggtgttgctg atttcaataa agtcttgaga tcagtttggc    9420
gcgccagctg cattaatgaa tcggccaacg cgcggggaga ggcggtttgc gtattgggcg    9480
ctcttccgct tcctcgctca ctgactcgct gcgctcggtc gttcggctgc ggcgagcggt    9540
atcagctcac tcaaaggcgg taatacggtt atccacagaa tcagggggata acgcaggaaa    9600
```

```
gaacatgtga gcaaaaggcc agcaaaaggc caggaaccgt aaaaaggccg cgttgctggc   9660
gttttccat  aggctccgcc ccctgacga  gcatcacaaa aatcgacgct caagtcagag   9720
gtggcgaaac ccgacaggac tataaagata ccaggcgttt ccccctggaa gctccctcgt   9780
gcgctctcct gttccgaccc tgccgcttac cggatacctg tccgcctttc tcccttcggg   9840
aagcgtggcg ctttctcata gctcacgctg taggtatctc agttcggtgt aggtcgttcg   9900
ctccaagctg ggctgtgtgc acgaaccccc cgttcagccc gaccgctgcg ccttatccgg   9960
taactatcgt cttgagtcca acccggtaag acacgactta tcgccactgg cagcagccac  10020
tggtaacagg attagcagag cgaggtatgt aggcggtgct acagagttct tgaagtggtg  10080
gcctaactac ggctacacta agaacagt   atttggtatc tgcgctctgc tgaagccagt  10140
taccttcgga aaagagttg  gtagctcttg atccggcaaa caaccaccg  ctggtagcgg  10200
tggttttttt gtttgcaagc agcagattac gcgcagaaaa aaaggatctc aagaagatcc  10260
tttgatcttt tctacggggt ctgacgctca gtggaacgaa aactcacgtt aagggatttt  10320
ggtcatgaga ttatcaaaaa ggatcttcac ctagatcctt ttaaattaaa aatgaagttt  10380
taaatcaatc taaagtatat atgagtaaac ttggtctgac agttaccaat gcttaatcag  10440
tgaggcacct atctcagcga tctgtctatt tcgttcatcc atagttgcct gactccccgt  10500
cgtgtagata actacgatac gggagggctt accatctggc cccagtgctg caatgatacc  10560
gcgagaccca cgctcaccgg ctccagattt atcagcaata aaccagccag ccggaagggc  10620
cgagcgcaga agtggtcctg caactttatc cgcctccatc cagtctatta attgttgccg  10680
ggaagctaga gtaagtagtt cgccagttaa tagtttgcgc aacgttgttg ccattgctac  10740
aggcatcgtg gtgtcacgct cgtcgtttgg tatggcttca ttcagctccg gttcccaacg  10800
atcaaggcga gttacatgat cccccatgtt gtgcaaaaaa gcggttagct ccttcggtcc  10860
tccgatcgtt gtcagaagta agttggccgc agtgttatca ctcatggtta tggcagcact  10920
gcataattct cttactgtca tgccatccgt aagatgcttt tctgtgactg gtgagtactc  10980
aaccaagtca ttctgagaat agtgtatgcg gcgaccgagt tgctcttgcc cggcgtcaat  11040
acgggataat accgcgccac atagcagaac tttaaaagtg ctcatcattg gaaaacgttc  11100
ttcggggcga aaactctcaa ggatcttacc gctgttgaga tccagttcga tgtaacccac  11160
tcgtgcaccc aactgatctt cagcatcttt tactttcacc agcgtttctg ggtgagcaaa  11220
aacaggaagg caaaatgccg caaaaaaggg aataagggcg acacggaaat gttgaatact  11280
catactcttc ctttttcaat attattgaag catttatcag ggttattgtc tcatgagcgg  11340
atacatattt gaatgtattt agaaaaataa acaaataggg gttccgcgca catttccccg  11400
aaaagtgcca cctgatgcgg tgtgaaatac cgcacagatg cgtaaggaga aaataccgca  11460
tcaggaaatt gtaagcgtta atattttgtt aaaattcgcg ttaaattttt gttaaatcag  11520
ctcatttttt aaccaatagg ccgaaatcgg caaaatccct tataaatcaa agaatagac   11580
cgagataggg ttgagtgttg ttccagtttg gaacaagagt ccactattaa agaacgtgga  11640
ctccaacgtc aaagggcgaa aaaccgtcta tcagggcgat ggcccactac gtgaaccatc  11700
accctaatca agttttttgg ggtcgaggtg ccgtaaagca ctaaatcgga acctaaagg   11760
gagcccccga tttagagctt gacggggaaa gccggcgaac gtggcgagaa aggaagggaa  11820
gaaagcgaaa ggagcgggcg ctagggcgct ggcaagtgta gcggtcacgc tgcgcgtaac  11880
caccacaccc gccgcgctta atgcgccgct acagggcgcg tccattcgcc attcaggctg  11940
```

```
cgcaactgtt gggaagggcg atcggtgcgg gcctcttcgc tattacgcca gctggcgaaa      12000
gggggatgtg ctgcaaggcg attaagttgg gtaacgccag ggttttccca gtcacgacgt      12060
tgtaaaacga cggccagtga attgtaatac gactcactat agggcgaatt gggcccgacg      12120
tcgcatgcag tggtggtatt tgtgactggg gatgtagttga gaataagtca tacacaagtc      12180
agctttcttc gagcctcata taagtataag tagttcaacg tattagcact gtacccagca      12240
tctccgtatc gagaaacaca acaacatgcc ccattggaca gatcatgcgg atacacaggt      12300
tgtgcagtat catacatact cgatcagaca ggtcgtctga ccatcataca agctgaacaa      12360
gcgctccata cttgcacgct ctctatatac acagttaaat tacatatcca tagtctaacc      12420
tctaacagtt aatcttctgg taagcctccc agccagcctt ctggtatcgc ttggcctcct      12480
caataggatc tcggttctgg ccgtacgac ctcggccgac aattatgata tccgttccgg       12540
tagacatgac atcctcaaca gttcggtact gctgtccgag agcgtctccc ttgtcgtcaa      12600
gacccacccc gggggtcaga ataagccagt cctcagagtc gcccttaat                  12649
```

<210> SEQ ID NO 25
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized) for
      Yarrowia lipolytica

<400> SEQUENCE: 25

```
atggccaact cctctgtctg ggacgacgtg gtcggacgag tcgagaccgg tgtcgaccag        60
tggatggacg gagctaagcc ctacgctctg accgacggtc tgcccatgat ggacgtctcc       120
accatgctcg ccttcgaggt cggctacatg gccatgctgc tcttcggcat tcccatcatg       180
aagcagatgg agaagccctt cgagctgaag accatcaagc tgctccacaa cctgttcctc       240
ttcggactgt ccctctacat gtgcgtcgag accatccgac aggctatcct gggtggctac       300
aaggtcttcg gcaacgacat ggagaagggc aacgagtccc acgctcaggg catgtcccga       360
atcgtctacg tgttctacgt ctccaaggcc tacgagttcc tggacaccgc tatcatgatc       420
ctgtgcaaga gttcaaccca ggtctccttc ctgcacgtgt accaccatgc caccatcttc       480
gccatctggt gggctattgc caagtacgct cctggtggcg acgcctactt ctccgtcatc       540
ctcaactcct tcgtccacac cgtcatgtac gcctactact tcttttcctc tcagggcttc       600
ggcttcgtca agcccatcaa gccctacatc accactctgc agatgacccg ttcatggct       660 atgctggtgc agtccctgta cgactacctc ttccctgcg actaccctca ggctctggtc       720
cagctgctcg gcgtgtacat gatcaccctg ctcgctctgt cggcaacttt ctttgtccag      780
tcctacctga agaagcccaa gaagtccaag accaactaa                             819
```

<210> SEQ ID NO 26
<211> LENGTH: 272
<212> TYPE: PRT
<213> ORGANISM: Thraustochytrium aureum

<400> SEQUENCE: 26

```
Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
```

-continued

```
                35                  40                  45
Tyr Met Ala Met Leu Leu Phe Gly Ile Pro Ile Met Lys Gln Met Glu
 50                  55                  60

Lys Pro Phe Glu Leu Lys Thr Ile Lys Leu Leu His Asn Leu Phe Leu
 65                  70                  75                  80

Phe Gly Leu Ser Leu Tyr Met Cys Val Glu Thr Ile Arg Gln Ala Ile
                 85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
            260                 265                 270

<210> SEQ ID NO 27
<211> LENGTH: 37
<212> TYPE: DNA
<213> ORGANISM: Artificial Sequence
<220> FEATURE:
<223> OTHER INFORMATION: Primer AP

<400> SEQUENCE: 27
ggccacgcgt cgactagtac ttttttttttt tttttt                         37

<210> SEQ ID NO 28
<211> LENGTH: 39
<212> TYPE: DNA
<213> ORGANISM: Artificial Sequence
<220> FEATURE:
<223> OTHER INFORMATION: Smart IV oligonucleotide primer

<400> SEQUENCE: 28
aagcagtggt atcaacgcag agtggccatt acggccggg                       39

<210> SEQ ID NO 29
<211> LENGTH: 23
<212> TYPE: DNA
<213> ORGANISM: Artificial Sequence
<220> FEATURE:
<223> OTHER INFORMATION: Primer CDSIII 5'

<400> SEQUENCE: 29
aagcagtggt atcaacgcag agt                                        23
```

-continued

<210> SEQ ID NO 30
<211> LENGTH: 20
<212> TYPE: DNA
<213> ORGANISM: Artificial Sequence
<220> FEATURE:
<223> OTHER INFORMATION: Degenerate primer 5-1A

<400> SEQUENCE: 30
gghcaycayr tbtayacaaa                                                    20

<210> SEQ ID NO 31
<211> LENGTH: 20
<212> TYPE: DNA
<213> ORGANISM: Artificial Sequence
<220> FEATURE:
<223> OTHER INFORMATION: Degenerate primer 5-1B

<400> SEQUENCE: 31
gghcaycayr tbtayaccaa                                                    20

<210> SEQ ID NO 32
<211> LENGTH: 20
<212> TYPE: DNA
<213> ORGANISM: Artificial Sequence
<220> FEATURE:
<223> OTHER INFORMATION: Degenerate primer 5-1C

<400> SEQUENCE: 32
gghcaycayr tbtayacgaa                                                    20

<210> SEQ ID NO 33
<211> LENGTH: 20
<212> TYPE: DNA
<213> ORGANISM: Artificial Sequence
<220> FEATURE:
<223> OTHER INFORMATION: Degenerate primer 5-1D

<400> SEQUENCE: 33
gghcaycayr tbtayactaa                                                    20

<210> SEQ ID NO 34
<211> LENGTH: 20
<212> TYPE: DNA
<213> ORGANISM: Artificial Sequence
<220> FEATURE:
<223> OTHER INFORMATION: Degenerate primer 5-4AR
<220> FEATURE:
<221> NAME/KEY: misc_feature
<222> LOCATION: (9)..(9)
<223> OTHER INFORMATION: n is a, c, g, or t

<400> SEQUENCE: 34
acrtgrytna cytgraagtt                                                    20

<210> SEQ ID NO 35
<211> LENGTH: 20
<212> TYPE: DNA
<213> ORGANISM: Artificial Sequence
<220> FEATURE:
<223> OTHER INFORMATION: Degenerate primer 5-4BR
<220> FEATURE:
<221> NAME/KEY: misc_feature
<222> LOCATION: (9)..(9)
<223> OTHER INFORMATION: n is a, c, g, or t

<400> SEQUENCE: 35
acrtgrytna cytgraaatt                    20

<210> SEQ ID NO 36
<211> LENGTH: 20
<212> TYPE: DNA
<213> ORGANISM: Artificial Sequence
<220> FEATURE:
<223> OTHER INFORMATION: Degenerate primer 5-4CR
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 36
acrtgngana cytgraagtt                    20

<210> SEQ ID NO 37
<211> LENGTH: 20
<212> TYPE: DNA
<213> ORGANISM: Artificial Sequence
<220> FEATURE:
<223> OTHER INFORMATION: Degenerate primer 5-4DR
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 37
acrtgngana cytgraaatt                    20

<210> SEQ ID NO 38
<211> LENGTH: 25
<212> TYPE: DNA
<213> ORGANISM: Artificial Sequence
<220> FEATURE:
<223> OTHER INFORMATION: Primer ODMW520

<400> SEQUENCE: 38
cgttctccat tttcattcca accgc              25

<210> SEQ ID NO 39
<211> LENGTH: 28
<212> TYPE: DNA
<213> ORGANISM: Artificial Sequence
<220> FEATURE:
<223> OTHER INFORMATION: Primer ODMW521

<400> SEQUENCE: 39
ggttgaagac cgaagagacc cagtatcc           28

<210> SEQ ID NO 40
<211> LENGTH: 22
<212> TYPE: DNA
<213> ORGANISM: Artificial Sequence
<220> FEATURE:
<223> OTHER INFORMATION: Primer DNR CDS 5'

<400> SEQUENCE: 40
caacgcagag tggccattac gg                 22

<210> SEQ ID NO 41
<211> LENGTH: 28
<212> TYPE: DNA
<213> ORGANISM: Artificial Sequence
<220> FEATURE:
<223> OTHER INFORMATION: Primer ODMW541

<400> SEQUENCE: 41
ctcgcggcct cgtcgcacaa tcttgaag                                    28

<210> SEQ ID NO 42
<211> LENGTH: 29
<212> TYPE: DNA
<213> ORGANISM: Artificial Sequence
<220> FEATURE:
<223> OTHER INFORMATION: Primer ODMW542

<400> SEQUENCE: 42
gagtatcaaa cttgtattcc gaggtgtag                                   29

<210> SEQ ID NO 43
<211> LENGTH: 26
<212> TYPE: DNA
<213> ORGANISM: Artificial Sequence
<220> FEATURE:
<223> OTHER INFORMATION: Primer ODMW523

<400> SEQUENCE: 43
ggttcaagtc gcaagtcgaa acctcg                                      26

<210> SEQ ID NO 44
<211> LENGTH: 20
<212> TYPE: DNA
<213> ORGANISM: Artificial Sequence
<220> FEATURE:
<223> OTHER INFORMATION: Primer AUAP

<400> SEQUENCE: 44
ggccacgcgt cgactagtac                                             20

<210> SEQ ID NO 45
<211> LENGTH: 25
<212> TYPE: DNA
<213> ORGANISM: Artificial Sequence
<220> FEATURE:
<223> OTHER INFORMATION: Primer ODMW524

<400> SEQUENCE: 45
caacttacgg aggtttcatc tcggg                                       25

<210> SEQ ID NO 46
<211> LENGTH: 31
<212> TYPE: DNA
<213> ORGANISM: Artificial Sequence
<220> FEATURE:
<223> OTHER INFORMATION: Primer YL807

<400> SEQUENCE: 46
tttccatggc tccagatgcg gacaagttga g                                31

<210> SEQ ID NO 47
<211> LENGTH: 29
<212> TYPE: DNA
<213> ORGANISM: Artificial Sequence
<220> FEATURE:
<223> OTHER INFORMATION: Primer YL810

```
<400> SEQUENCE: 47
caaggcatcg ggatccttct catggtggt                                              29

<210> SEQ ID NO 48
<211> LENGTH: 42
<212> TYPE: DNA
<213> ORGANISM: Artificial Sequence
<220> FEATURE:
<223> OTHER INFORMATION: Primer YL808

<400> SEQUENCE: 48
tttgcggccg cttacaattt tcccgagtag gggttggcgc ca                               42

<210> SEQ ID NO 49
<211> LENGTH: 29
<212> TYPE: DNA
<213> ORGANISM: Artificial Sequence
<220> FEATURE:
<223> OTHER INFORMATION: Primer YL809

<400> SEQUENCE: 49
accaccatga aaggatccc gatgccttg                                               29

<210> SEQ ID NO 50
<211> LENGTH: 4112
<212> TYPE: DNA
<213> ORGANISM: Artificial Sequence
<220> FEATURE:
<223> OTHER INFORMATION: Plasmid pRD5S

<400> SEQUENCE: 50
tcgcgcgttt cggtgatgac ggtgaaaacc tctgacacat gcagctcccg gagacggtca            60
cagcttgtct gtaagcggat gccggagca gacaagcccg tcagggcgcg tcagcgggtg            120
ttggcgggtg tcggggctgg cttaactatg cggcatcaga gcagattgta ctgagagtgc           180
accatatgcg gtgtgaaata ccgcacagat gcgtaaggag aaaataccgc atcaggcgcc           240
attcgccatt caggctgcgc aactgttggg aagggcgatc ggtgcgggcc tcttcgctat           300
tacgccagct ggcgaaaggg ggatgtgctg caaggcgatt aagttgggta acgccagggt           360
tttcccagtc acgacgttgt aaaacgacgg ccagtgaatt cgagctcggt acctcgcgaa           420
tgcatctaga tccatggctc ccgacgccga caagctgcga cagcgaaagg ctcagtccat           480
ccaggacact gccgattctc aggctaccga gctcaagatt ggcaccctga agggtctcca           540
aggcaccgag atcgtcattg atggcgacat ctacgacatc aaagacttcg atcaccctgg           600
aggcgaatcc atcatgacct tggtggcaa cgacgttact gccacctaca agatgattca           660
tccctaccac tcgaagcatc acctggagaa gatgaaaaag gtcggtcgag tgcccgacta           720
cacctccgag tacaagttcg atactcccctt cgaacgagag atcaaacagg aggtcttcaa           780
gattgtgcga gagaggtcgag agtttggaac acctggctac ttctttcgag ccttctgcta           840
catcggtctc ttctttttacc tgcagtatct ctgggttacc actcctacca ctttcgccct           900
tgctatcttc tacggtgtgt ctcaggcctt cattggcctg aacgtccagc acgacgccaa           960
ccacggagct gcctccaaaa agccctggat caacaatttg ctcggcctgg gtgccgactt          1020
tatcggaggc tccaagtggc tctggatgaa ccagcactgg acccatcaca cttacaccaa          1080 ccatacgag aaggatcccg acgcctgggt gcagagcct atgctgctct caacgacta            1140 tcccttgggt caccccaagc gaaccctcat tcatcacttc caagccttct actatctgtt          1200
tgtccttgct ggctactggg tgtcttcggt gttcaaccct cagatcctgg acctccagca          1260
```

```
ccgaggtgcc caggctgtcg gcatgaagat ggagaacgac tacattgcca agtctcgaaa    1320
gtacgctatc ttcctgcgac tcctgtacat ctacaccaac attgtggctc ccatccagaa    1380
ccaaggcttt tcgctcaccg tcgttgctca cattcttact atgggtgtcg cctccagcct    1440
gaccctcgct actctgttcg ccctctccca caacttcgag aacgcagatc gggatcccac    1500
ctacgaggct cgaaagggag gcgagcctgt ctgttggttc aagtcgcagg tggaaacctc    1560
ctctacttac ggtggcttca tttccggttg ccttacaggc ggactcaact ttcaggtcga    1620
gcatcacctg tttcctcgaa tgtcctctgc ctggtacccc tacatcgctc ctaccgttcg    1680
agaggtctgc aaaaagcacg gcgtcaagta cgcctactat ccctgggtgt ggcagaacct    1740
catctcgacc gtcaagtacc tgcatcagtc cggaactggc tcgaactgga agaacggtgc    1800
caatccctac tctggcaagc tgtaagcggc cgcatcggat cccgggcccg tcgactgcag    1860
aggcctgcat gcaagcttgg cgtaatcatg gtcatagctg tttcctgtgt gaaattgtta    1920
tccgctcaca attccacaca acatacgagc cggaagcata agtgtaaag cctggggtgc     1980
ctaatgagtg agctaactca cattaattgc gttgcgctca ctgcccgctt tccagtcggg    2040
aaacctgtcg tgccagctgc attaatgaat cggccaacgc gcggggagag gcggtttgcg    2100
tattgggcgc tcttccgctt cctcgctcac tgactcgctg cgctcggtcg ttcggctgcg    2160
gcgagcggta tcagctcact caaaggcggt aatacggtta tccacagaat caggggataa    2220
cgcaggaaag aacatgtgag caaaaggcca gcaaaaggcc aggaaccgta aaaaggccgc    2280
gttgctggcg ttttttccata ggctccgccc ccctgacgag catcacaaaa atcgacgctc    2340
aagtcagagg tggcgaaacc cgacaggact ataaagatac caggcgtttc ccctggaag    2400
ctccctcgtg cgctctcctg ttccgaccct gccgcttacc ggatacctgt ccgcctttct    2460
cccttcggga agcgtggcgc tttctcatag ctcacgctgt aggtatctca gttcggtgta    2520
ggtcgttcgc tccaagctgg gctgtgtgca cgaacccccc gttcagcccg accgctgcgc    2580
cttatccggt aactatcgtc ttgagtccaa cccggtaaga cacgacttat cgccactggc    2640
agcagccact ggtaacagga ttagcagagc gaggtatgta ggcggtgcta cagagttctt    2700
gaagtggtgg cctaactacg gctacactag aagaacagta tttggtatct gcgctctgct    2760
gaagccagtt accttcggaa aaagagttgg tagctcttga tccggcaaac aaaccaccgc    2820
tggtagcggt ggtttttttg tttgcaagca gcagattacg cgcagaaaaa aaggatctca    2880
agaagatcct ttgatctttt ctacggggtc tgacgctcag tggaacgaaa actcacgtta    2940
agggattttg gtcatgagat tatcaaaaag gatcttcacc tagatccttt taaattaaaa    3000
atgaagtttt aaatcaatct aaagtatata tgagtaaact tggtctgaca gttaccaatg    3060
cttaatcagt gaggcaccta tctcagcgat ctgtctattt cgttcatcca tagttgcctg    3120
actccccgtc gtgtagataa ctacgatacg ggagggctta ccatctggcc ccagtgctgc    3180
aatgataccg cgagacccac gctcaccggc tccagattta tcagcaataa accagccagc    3240
cggaagggcc gagcgcagaa gtggtcctgc aactttatcc gcctccatcc agtctattaa    3300
ttgttgccgg gaagctagag taagtagttc gccagttaat agtttgcgca acgttgttgc    3360
cattgctaca ggcatcgtgg tgtcacgctc gtcgtttggt atggcttcat tcagctccgg    3420
ttcccaacga tcaaggcgag ttacatgatc ccccatgttg tgcaaaaaag cggttagctc    3480
cttcggtcct ccgatcgttg tcagaagtaa gttggccgca gtgttatcac tcatggttat    3540
ggcagcactg cataattctc ttactgtcat gccatccgta agatgctttt ctgtgactgg    3600
```

```
tgagtactca accaagtcat tctgagaata gtgtatgcgg cgaccgagtt gctcttgccc    3660
ggcgtcaata cgggataata ccgcgccaca tagcagaact ttaaaagtgc tcatcattgg    3720
aaaacgttct cgggcgaa aactctcaag gatcttaccg ctgttgagat ccagttcgat     3780
gtaacccact cgtgcaccca actgatcttc agcatctttt actttcacca gcgtttctgg    3840
gtgagcaaaa acaggaaggc aaaatgccgc aaaaaaggga ataagggcga cacggaaatg    3900
ttgaatactc atactcttcc tttttcaata ttattgaagc atttatcagg gttattgtct    3960
catgagcgga tacatatttg aatgtattta gaaaaataaa caaatagggg ttccgcgcac    4020
atttccccga aaagtgccac ctgacgtcta agaaaccatt attatcatga cattaaccta    4080
taaaaatagg cgtatcacga ggccctttcg tc                                 4112

<210> SEQ ID NO 51
<211> LENGTH: 8480
<212> TYPE: DNA
<213> ORGANISM: Artificial Sequence
<220> FEATURE:
<223> OTHER INFORMATION: Plasmid pZURD5S

<400> SEQUENCE: 51
catggctccc gacgccgaca agctgcgaca gcgaaaggct cagtccatcc aggacactgc      60
cgattctcag gctaccgagc tcaagattgg caccctgaag gtctccaag gcaccgagat     120 cgtcattgat ggcgacatct acgacatcaa agacttcgat caccctggag gcgaatccat    180
catgaccttt ggtggcaacg acgttactgc cacctacaag atgattcatc cctaccactc    240
gaagcatcac ctggagaaga tgaaaaaggt cggtcgagtg cccgactaca cctccgagta    300
caagttcgat actccctcg aacgagagat caaacaggag gtcttcaaga ttgtgcgaag    360
aggtcgagag tttggaacac ctggctactt cttcgagcc ttctgctaca tcggtctctt    420
cttttacctg cagtatctct gggttaccac tcctaccact ttcgcccttg ctatcttcta    480
cggtgtgtct caggccttca ttggcctgaa cgtccagcac gacgccaacc acggagctgc    540
ctccaaaaag ccctggatca acaattgct cggcctgggt gccgacttta tcggaggctc    600
caagtggctc tggatgaacc agcactggac ccatcacact acaccaacc atcacgagaa    660 ggatcccgac gccctgggtg cagagcctat gctgctcttc aacgactatc ccttgggtca    720
ccccaagcga accctcattc atcacttcca agccttctac tatctgtttg tccttgctgg    780
ctactgggtg tcttcggtgt tcaaccctca gatcctggac ctccagcacc gaggtgccca    840
ggctgtcggc atgaagatgg agaacgacta cattgccaag tctcgaaagt acgctatctt    900
cctgcgactc ctgtacatct acaccaacat tgtggctccc atccagaacc aaggctttc    960 gctcaccgtc gttgctcaca ttcttactat gggtgtcgcc tccagcctga ccctcgctac    1020
tctgttcgcc ctctcccaca cttcgagaa cgcagatcgg gatcccacct acgaggctcg    1080
aaagggaggc gagcctgtct gttggttcaa gtcgcaggtg gaaaccctcct ctacttacgg    1140 tggcttcatt tccggttgcc ttacaggcgg actcaacttt caggtcgagc atcacctgtt    1200
tcctcgaatg tcctctgcct ggtaccccta catcgctcct accgttcgag aggtctgcaa    1260
aaagcacggc gtcaagtacg cctactatcc ctgggtgtgg cagaacctca tctcgaccgt    1320
caagtacctg catcagtccg gaactggctc gaactggaag aacggtgcca atccctactc    1380
tggcaagctg taagcggccg caagtgtgga tggggaagtg agtgcccggt tctgtgtgca    1440
caattggcaa tccaagatgg atggattcaa cacaggatta tagcgagcta cgtggtggtg    1500
cgaggatata gcaacggata tttatgtttg acacttgaga atgtacgata caagcactgt    1560
```

```
ccaagtacaa tactaaacat actgtacata ctcatactcg tacccgggca acggtttcac   1620
ttgagtgcag tggctagtgc tcttactcgt acagtgtgca atactgcgta tcatagtctt   1680
tgatgtatat cgtattcatt catgttagtt gcgtacgagc cggaagcata aagtgtaaag   1740
cctggggtgc ctaatgagtg agctaactca cattaattgc gttgcgctca ctgcccgctt   1800
tccagtcggg aaacctgtcg tgccagctgc attaatgaat cggccaacgc gcggggagag   1860
gcggtttgcg tattgggcgc tcttccgctt cctcgctcac tgactcgctg cgctcggtcg   1920
ttcggctgcg gcgagcggta tcagctcact caaaggcggt aatacggtta tccacagaat   1980
caggggataa cgcaggaaag aacatgtgag caaaaggcca gcaaaaggcc aggaaccgta   2040
aaaaggccgc gttgctggcg ttttccata ggctccgccc ccctgacgag catcacaaaa   2100
atcgacgctc aagtcagagg tggcgaaacc cgacaggact ataaagatac caggcgtttc   2160
cccctggaag ctccctcgtg cgctctcctg ttccgaccct gccgcttacc ggatacctgt   2220
ccgcctttct cccttcggga agcgtggcgc tttctcatag ctcacgctgt aggtatctca   2280
gttcggtgta ggtcgttcgc tccaagctgg gctgtgtgca cgaaccccc gttcagcccg    2340
accgctgcgc cttatccggt aactatcgtc ttgagtccaa cccggtaaga cacgacttat   2400
cgccactggc agcagccact ggtaacagga ttagcagagc gaggtatgta ggcggtgcta   2460
cagagttctt gaagtggtgg cctaactacg gctacactag aaggacagta tttggtatct   2520
gcgctctgct gaagccagtt accttcggaa aaagagttgg tagctcttga tccggcaaac   2580
aaaccaccgc tggtagcggt ggtttttttg tttgcaagca gcagattacg cgcagaaaaa   2640
aaggatctca agaagatcct ttgatctttt ctacggggtc tgacgctcag tggaacgaaa   2700
actcacgtta agggattttg gtcatgagat tatcaaaaag gatcttcacc tagatccttt   2760
taaattaaaa atgaagtttt aaatcaatct aaagtatata tgagtaaact tggtctgaca   2820
gttaccaatg cttaatcagt gaggcaccta tctcagcgat ctgtctattt cgttcatcca   2880
tagttgcctg actccccgtc gtgtagataa ctacgatacg ggagggctta ccatctggcc   2940
ccagtgctgc aatgataccg cgagacccac gctcaccggc tccagattta tcagcaataa   3000
accagccagc cggaagggcc gagcgcagaa gtggtcctgc aactttatcc gcctccatcc   3060
agtctattaa ttgttgccgg gaagctagag taagtagttc gccagttaat agtttgcgca   3120
acgttgttgc cattgctaca ggcatcgtgg tgtcacgctc gtcgtttggt atggcttcat   3180
tcagctccgg ttcccaacga tcaaggcgag ttacatgatc ccccatgttg tgcaaaaaag   3240
cggttagctc cttcggtcct ccgatcgttg tcagaagtaa gttggccgca gtgttatcac   3300
tcatggttat ggcagcactg cataattctc ttactgtcat gccatccgta agatgctttt   3360
ctgtgactgg tgagtactca accaagtcat tctgagaata gtgtatgcgg cgaccgagtt   3420
gctcttgccc ggcgtcaata cgggataata ccgcgccaca tagcagaact ttaaaagtgc   3480
tcatcattgg aaaacgttct cggggcgaaa actctcaag gatcttaccg ctgttgagat    3540
ccagttcgat gtaacccact cgtgcaccca actgatcttc agcatctttt actttcacca   3600
gcgtttctgg gtgagcaaaa acaggaaggc aaaatgccgc aaaaaaggga ataagggcga   3660
cacggaaatg ttgaatactc atactcttcc ttttcaata ttattgaagc atttatcagg    3720
gttattgtct catgagcgga tacatatttg aatgtattta gaaaaataaa caaatagggg   3780
ttccgcgcac atttccccga aaagtgccac ctgacgcgcc ctgtagcggc gcattaagcg   3840
cggcgggtgt ggtggttacg cgcagcgtga ccgctacact tgccagcgcc ctagcgcccg   3900
```

```
ctcctttcgc tttcttccct tcctttctcg ccacgttcgc cggctttccc cgtcaagctc   3960
taaatcgggg gctcccttta gggttccgat ttagtgcttt acggcacctc gaccccaaaa   4020
aacttgatta gggtgatggt tcacgtagtg ggccatcgcc ctgatagacg gtttttcgcc   4080
ctttgacgtt ggagtccacg ttctttaata gtggactctt gttccaaact ggaacaacac   4140
tcaaccctat ctcggtctat tcttttgatt tataagggat tttgccgatt tcggcctatt   4200
ggttaaaaaa tgagctgatt taacaaaaat ttaacgcgaa ttttaacaaa atattaacgc   4260
ttacaatttc cattcgccat tcaggctgcg caactgttgg gaagggcgat cggtgcgggc   4320
ctcttcgcta ttacgccagc tggcgaaagg gggatgtgct gcaaggcgat taagttgggt   4380
aacgccaggg ttttcccagt cacgacgttg taaaacgacg ccagtgaatt gtaatacga   4440 ctcactatag gcgaattgg gtaccgggcc cccctcgag gtcgatggtg tcgataagct   4500
tgatatcgaa ttcatgtcac acaaaccgat cttcgcctca aggaaaccta attctacatc   4560
cgagagactc ccgagatcca gtctacactg attaattttc gggccaataa tttaaaaaaa   4620
tcgtgttata taatattata tgtattatat atatacatca tgatgatact gacagtcatg   4680
tcccattgct aaatagacag actccatctg ccgcctccaa ctgatgttct caatattaa    4740 ggggtcatct cgcattgttt aataataaac agactccatc taccgcctcc aaatgatgtt   4800
ctcaaaatat attgtatgaa cttattttta ttacttagta ttattagaca acttacttgc   4860
tttatgaaaa acacttccta tttaggaaac aatttataat ggcagttcgt tcatttaaca   4920
atttatgtag aataaatgtt ataaatgcgt atgggaaatc ttaaatatgg atagcataaa   4980
tgatatctgc attgcctaat tcgaaatcaa cagcaacgaa aaaaatccct tgtacaacat   5040
aaatagtcat cgagaaatat caactatcaa agaacagcta ttcacacgtt actattgaga   5100
ttattattgg acgagaatca cacactcaac tgtctttctc tcttctagaa atacaggtac   5160
aagtatgtac tattctcatt gttcatactt ctagtcattt catcccacat attccttgga   5220
tttctctcca atgaatgaca ttctatcttg caaattcaac aattataata agatataccca  5280 aagtagcggt atagtggcaa tcaaaaagct tctctggtgt gcttctcgta tttattttta   5340
ttctaatgat ccattaaagg tatatattta tttcttgtta tataatcctt tgtttatta    5400 catgggctgg atacataaag gtattttgat ttaattttt gcttaaattc aatcccccct    5460
cgttcagtgt caactgtaat ggtaggaaat taccatactt ttgaagaagc aaaaaaaatg   5520
aaagaaaaaa aaaatcgtat ttccaggtta gacgttccgc agaatctaga atgcggtatg   5580
cggtacattg ttcttcgaac gtaaagttg cgctccctga gatattgtac attttttgctt   5640 ttacaagtac aagtacatcg tacaactatg tactactgtt gatgcatcca caacagtttg   5700
ttttgttttt ttttgttttt ttttttctca atgattcatt accgctatgt atacctactt   5760
gtacttgtag taagccgggt tattggcgtt caattaatca tagacttatg aatctgcacg   5820
gtgtgcgctg cgagttactt ttagcttatg catgctactt gggtgtaata ttgggatctg   5880
ttcggaaatc aacggatgct caatcgattt cgacagtaat taattaagtc atacacaagt   5940
cagctttctt cgagcctcat ataagtataa gtagttcaac gtattagcac tgtacccagc   6000
atctccgtat cgagaaacac aacaacatgc cccattggac agatcatgcg gatacacagg   6060
ttgtgcagta tcatacatac tcgatcagac aggtcgtctg accatcatac aagctgaaca   6120
agcgctccat acttgcacgc tctctatata cacagttaaa ttacatatcc atagtctaac   6180
ctctaacagt taatcttctg gtaagcctcc cagccagcct tctggtatcg cttggcctcc   6240
tcaataggat ctcggttctg gccgtacaga cctcggccga caattatgat atccgttccg   6300
```

```
gtagacatga catcctcaac agttcggtac tgctgtccga gagcgtctcc cttgtcgtca  6360
agacccaccc cggggtcag aataagccag tcctcagagt cgcccttagg tcggttctgg   6420
gcaatgaagc caaccacaaa ctcggggtcg gatcgggcaa gctcaatggt ctgcttggag  6480
tactcgccag tggccagaga gcccttgcaa gacagctcgg ccagcatgag cagacctctg  6540
gccagcttct cgttgggaga ggggactagg aactccttgt actgggagtt ctcgtagtca  6600
gagacgtcct ccttcttctg ttcagagaca gtttcctcgg caccagctcg caggccagca  6660
atgattccgg ttccgggtac accgtgggcg ttggtgatat cggaccactc ggcgattcgg  6720
tgacaccggt actggtgctt gacagtgttg ccaatatctg cgaactttct gtcctcgaac  6780
aggaagaaac cgtgcttaag agcaagttcc ttgaggggga gcacagtgcc ggcgtaggtg  6840
aagtcgtcaa tgatgtcgat atgggttttg atcatgcaca cataaggtcc gaccttatcg  6900
gcaagctcaa tgagctcctt ggtggtggta acatccagag aagcacacag gttggttttc  6960
ttggctgcca cgagcttgag cactcgagcg gcaaaggcgg acttgtggac gttagctcga  7020
gcttcgtagg agggcatttt ggtggtgaag aggagactga aataaattta gtctgcagaa  7080 cttttatcg gaaccttatc tggggcagtg aagtatatgt tatggtaata gttacgagtt   7140
agttgaactt atagatagac tggactatac ggctatcgt ccaaattaga aagaacgtca   7200
atggctctct gggcgtcgcc tttgccgaca aaaatgtgat catgatgaaa gccagcaatg  7260 acgttcagc tgatattgtt gtcggccaac cgcgccgaaa acgcagctgt cagacccaca   7320
gcctccaacg aagaatgtat cgtcaaagtg atccaagcac actcatagtt ggagtcgtac  7380
tccaaaggcg gcaatgacga gtcagacaga tactcgtcga ctcaggcgac gacggaattc  7440
ctgcagccca tctgcagaat tcaggagaga ccgggttggc ggcgtatttg tgtcccaaaa  7500
aacagcccca attgccccgg agaagacggc caggccgcct agatgacaaa ttcaacaact  7560
cacagctgac tttctgccat tgccactagg ggggggcctt tttatatggc caagccaagc  7620
tctccacgtc ggttgggctg cacccaacaa taaatgggta gggttgcacc aacaaaggga  7680
tgggatgggg ggtagaagat acgaggataa cggggctcaa tggcacaaat aagaacgaat  7740
actgccatta agactcgtga tccagcgact gacaccattg catcatctaa gggcctcaaa  7800
actacctcgg aactgctgcg ctgatctgga caccacagag gttccgagca ctttaggttg  7860
caccaaatgt cccaccaggt gcaggcagaa aacgctggaa cagcgtgtac agtttgtctt  7920
aacaaaaagt gagggcgctg aggtcgagca gggtggtgtg acttgttata gccttaagag  7980
ctgcgaaagc gcgtatggat ttggctcatc aggccagatt gagggtctgt ggacacatgt  8040
catgttagtg tacttcaatc gcccctgga tatagcccg acaataggcc gtggcctcat   8100
ttttttgcct tccgcacatt tccattgctc ggtacccaca ccttgcttct cctgcacttg  8160
ccaaccttaa tactggttta cattgaccaa catcttacaa gcgggggct tgtctagggt    8220 atatataaac agtggctctc ccaatcggtt gccagtctct ttttccttt ctttccccac   8280 agattcgaaa tctaaactac acatcacaca atgcctgtta ctgacgtcct taagcgaaag  8340
tccggtgtca tcgtcggcga cgatgtccga gccgtgagta tccacgacaa gatcagtgtc  8400
gagacgacgc gttttgtgta atgacacaat ccgaaagtcg ctagcaacac acactctcta  8460
cacaaactaa cccagctctc                                              8480

<210> SEQ ID NO 52
<211> LENGTH: 19
<212> TYPE: DNA
```

<213> ORGANISM: Artificial Sequence
<220> FEATURE:
<223> OTHER INFORMATION: Primer T7

<400> SEQUENCE: 52
ggaaacagct atgaccatg                                                                  19

<210> SEQ ID NO 53
<211> LENGTH: 459
<212> TYPE: PRT
<213> ORGANISM: Rhizopus stolonifer (GenBank Accession No. AAX22052)

<400> SEQUENCE: 53

Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Leu Leu
130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
            180                 185                 190

Val Phe Leu Gly Asn Phe Cys Gln Gly Phe Ser Leu Ser Trp Trp Lys
        195                 200                 205

Asn Lys His Asn Thr His His Ala Ser Thr Asn Val His Gly Gln Asp
210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe Phe
            260                 265                 270

Ile Leu Ala Phe Ala Arg Leu Ser Trp Ala Leu Gln Ser Leu Ser Tyr
        275                 280                 285

Ser Phe Lys Lys Glu Ser Ile Asn Lys Ser Arg Gln Leu Asn Leu Phe
    290                 295                 300

Glu Arg Val Cys Ile Val Gly His Trp Ala Leu Phe Ala Phe Cys Ile
305                 310                 315                 320

Tyr Ser Trp Cys Ser Asn Val Tyr His Met Val Leu Phe Phe Leu Val
                325                 330                 335

```
Ser Gln Ala Thr Thr Gly Tyr Thr Leu Ala Leu Val Phe Ala Leu Asn
            340                 345                 350

His Asn Gly Met Pro Val Ile Thr Glu Glu Lys Ala Glu Ser Met Glu
            355                 360                 365

Phe Phe Glu Ile Gln Val Ile Thr Gly Arg Asp Val Thr Leu Ser Pro
            370                 375                 380

Leu Gly Asp Trp Phe Met Gly Gly Leu Asn Tyr Gln Ile Glu His His
385                 390                 395                 400

Val Phe Pro Asn Met Pro Arg His Asn Leu Pro Thr Val Lys Pro Met
                405                 410                 415

Val Lys Ser Leu Cys Gln Lys Tyr Asp Ile Asn Tyr His Asp Thr Gly
            420                 425                 430

Phe Leu Lys Gly Thr Leu Glu Val Leu Gln Thr Leu Asp Ile Thr Ser
            435                 440                 445

Lys Leu Ser Leu Gln Leu Ser Lys Lys Ser Phe
            450                 455

<210> SEQ ID NO 54
<211> LENGTH: 695
<212> TYPE: DNA
<213> ORGANISM: Pavlova lutheri

<400> SEQUENCE: 54
agggccaagg gtgccaacca ccttccacgt gagactacac accgtaggcc gatgggcaag        60
ggtggagacg gcggcgcgca ggcggtgagc gggaccgacg cgtctctcgc tgaggtgagc       120
tccgtcgata gcaagagcgt gcacgtcgtg ctctacggca agcgcgtgga tgtcacaaag       180
ttccagggct acgacgtggc ctggtggcgc gcgcgccata acacgcacca cgtgtgcacc       240
aacgaggatg gttcggaccc ggacatcaag acggcgcccc tgctcatcta cgtgcgagag       300
aacccgtcca ttgccaagcg gctcaacttc ttccagcgct ggcagcagta ctactatgtg       360
ccgaccatgg ccatcctcga cctctactgg cgcctggagt ccatcgcgta cgtggctgtg       420
cgcctgccta agatgtggat gcaggccgcc gctcttgccg ctcactacgc gctcctgtgc       480
tgggtcttcg cagcgcatct caacctcatc cctctcatga tggttgcacg cggcttcgcg       540
acgggcatcg ttgtctttgc aacccactat ggtgaggaca tcctcgaccg cgagcacgtc       600
gagggcatga cgctcgtcga gcagaccgcc aagacctccc gtaacatcac gggcggctgg       660
ctagtgaacg tgctcacggg cttcatctcc ctgca                                  695

<210> SEQ ID NO 55
<211> LENGTH: 1106
<212> TYPE: DNA
<213> ORGANISM: Pavlova lutheri

<400> SEQUENCE: 55
agggccaagg gtgccaacca ccttccacgt gagactacac accgtaggcc gatgggcaag        60
ggtggagacg gcggcgcgca ggcggtgagc gggaccgacg cgtctctcgc tgaggtgagc       120
tccgtcgata gcaagagcgt gcacgtcgtg ctctacggca agcgcgtgga tgtcacaaag       180
ttccagggct acgacgtggc ctggtggcgc gcgcgccata acacgcacca cgtgtgcacc       240
aacgaggatg gttcggaccc ggacatcaag acggcgcccc tgctcatcta cgtgcgagag       300
aacccgtcca ttgccaagcg gctcaacttc ttccagcgct ggcagcagta ctactatgtg       360
ccgaccatgg ccatcctcga cctctactgg cgcctggagt ccatcgcgta cgtggctgtg       420
cgcctgccta agatgtggat gcaggccgcc gctcttgccg ctcactacgc gctcctgtgc       480
```

-continued

```
tgggtcttcg cagcgcatct caacctcatc cctctcatga tggttgcacg cggcttcgcg      540
acgggcatcg ttgtctttgc aacccactat ggtgaggaca tcctcgaccg cgagcacgtc      600
gagggcatga cgctcgtcga gcagaccgcc aagacctccc gtaacatcac gggcggctgg      660
ctagtgaacg tgctcacggg cttcatctcc ctgcagaccg agcatcacct cttccccatg      720
atgcccaccg caacctaat gactatccag cccgaggtac gcgacttctt caagaagcat       780
ggcctcgagt accgcgaggg caacctcttc cagtgcgtgc accagaacat caaggctctc      840
gccttcgagc acctcctcca ctgagcgtca ccactcaagc gtcctaagtg cacaggtact      900
gtcttctgac cgatggccgc gcggctccct cggctggcag tggggccaac gagtggcctc      960
gcgggatcgg gcacgatcgg gcctccatga aacttcagtg ttcagagaca agccgacaac     1020
ctccgcatcg tgagaaatct tttaaagcag tatgttccat cacgccgctt ttgcagtcaa     1080
taacattacc caaaaaaaaa aaaaaa                                          1106
```

<210> SEQ ID NO 56
<211> LENGTH: 287
<212> TYPE: PRT
<213> ORGANISM: Pavlova lutheri

<400> SEQUENCE: 56

```
Arg Ala Lys Gly Ala Asn His Leu Pro Arg Glu Thr Thr His Arg Arg
1               5                   10                  15

Pro Met Gly Lys Gly Gly Asp Gly Gly Ala Gln Ala Val Ser Gly Thr
            20                  25                  30

Asp Ala Ser Leu Ala Glu Val Ser Ser Val Asp Ser Lys Ser Val His
        35                  40                  45

Val Val Leu Tyr Gly Lys Arg Val Asp Val Thr Lys Phe Gln Gly Tyr
    50                  55                  60

Asp Val Ala Trp Trp Arg Ala Arg His Asn Thr His His Val Cys Thr
65                  70                  75                  80

Asn Glu Asp Gly Ser Asp Pro Asp Ile Lys Thr Ala Pro Leu Leu Ile
                85                  90                  95

Tyr Val Arg Glu Asn Pro Ser Ile Ala Lys Arg Leu Asn Phe Phe Gln
            100                 105                 110

Arg Trp Gln Gln Tyr Tyr Val Pro Thr Met Ala Ile Leu Asp Leu
        115                 120                 125

Tyr Trp Arg Leu Glu Ser Ile Ala Tyr Val Ala Val Arg Leu Pro Lys
    130                 135                 140

Met Trp Met Gln Ala Ala Ala Leu Ala Ala His Tyr Ala Leu Leu Cys
145                 150                 155                 160

Trp Val Phe Ala Ala His Leu Asn Leu Ile Pro Leu Met Met Val Ala
                165                 170                 175

Arg Gly Phe Ala Thr Gly Ile Val Val Phe Ala Thr His Tyr Gly Glu
            180                 185                 190

Asp Ile Leu Asp Arg Glu His Val Glu Gly Met Thr Leu Val Glu Gln
        195                 200                 205

Thr Ala Lys Thr Ser Arg Asn Ile Thr Gly Gly Trp Leu Val Asn Val
    210                 215                 220

Leu Thr Gly Phe Ile Ser Leu Gln Thr Glu His Leu Phe Pro Met
225                 230                 235                 240

Met Pro Thr Gly Asn Leu Met Thr Ile Gln Pro Glu Val Arg Asp Phe
                245                 250                 255
```

Phe Lys Lys His Gly Leu Glu Tyr Arg Glu Gly Asn Leu Phe Gln Cys
            260                 265                 270

Val His Gln Asn Ile Lys Ala Leu Ala Phe Glu His Leu Leu His
        275                 280                 285

<210> SEQ ID NO 57
<211> LENGTH: 20
<212> TYPE: DNA
<213> ORGANISM: Artificial Sequence
<220> FEATURE:
<223> OTHER INFORMATION: Primer SeqE

<400> SEQUENCE: 57
cgacacactc caatctttcc                                          20

<210> SEQ ID NO 58
<211> LENGTH: 20
<212> TYPE: DNA
<213> ORGANISM: Artificial Sequence
<220> FEATURE:
<223> OTHER INFORMATION: Primer SeqW

<400> SEQUENCE: 58
ggtggctgga gttagacatc                                          20

<210> SEQ ID NO 59
<211> LENGTH: 22
<212> TYPE: DNA
<213> ORGANISM: Artificial Sequence
<220> FEATURE:
<223> OTHER INFORMATION: Primer AP1

<400> SEQUENCE: 59
gtaatacgac tcactatagg gc                                       22

<210> SEQ ID NO 60
<211> LENGTH: 20
<212> TYPE: DNA
<213> ORGANISM: Artificial Sequence
<220> FEATURE:
<223> OTHER INFORMATION: Primer GSP PvDES

<400> SEQUENCE: 60
ctgcgaagac ccagcacagg                                          20

<210> SEQ ID NO 61
<211> LENGTH: 22
<212> TYPE: DNA
<213> ORGANISM: Artificial Sequence
<220> FEATURE:
<223> OTHER INFORMATION: Primer M13-28Rev

<400> SEQUENCE: 61
gtaatacgac tcactatagg gc                                       22

<210> SEQ ID NO 62
<211> LENGTH: 21
<212> TYPE: DNA
<213> ORGANISM: Artificial Sequence
<220> FEATURE:
<223> OTHER INFORMATION: Primer PavDes seq

<400> SEQUENCE: 62
ttgtggcgct caatcatctc c                                        21

<210> SEQ ID NO 63
<211> LENGTH: 1294
<212> TYPE: DNA
<213> ORGANISM: Pavlova lutheri

<400> SEQUENCE: 63

| | | | | | |
|---|---|---|---|---|---|
| ctttgcgagc | gcggcgcaga | cgattgcggc | ccgtagtgat | cgcggtgcgc | attgctgtgt | 60 |
| ttctagtttt | gctgacgccc | ggcccgataa | tgacaccttc | tcccgtttga | aatactaata | 120 |
| agtaactata | ttataatatt | caaaggtggc | gactatggat | ctccttttct | aaagttcagc | 180 |
| ggaattggga | atcggagaaa | tttcgagata | tgtcataatc | acgtgctcta | tctcgaatga | 240 |
| accgcggccg | gtgagcgatt | actcgggaag | ccaattccta | ttaacgagtc | aggggggatc | 300 |
| tttgaggtga | gtcggccacg | cagagagagc | aaggaatcat | cctcatccgc | cgttctcgag | 360 |
| aaagagccaa | gggtgccaac | caccttccac | gtgagactac | acaccgtagg | ccgatgggca | 420 |
| agggtggaga | cggcggcgcg | caggcggcga | gcgggaccga | cgcatctctc | gctgaggtga | 480 |
| gctccgtcga | tagcaagagc | gtgcgcgtcg | tgctctacgg | caagcgcgtg | gatgtcacaa | 540 |
| agttccagag | ggcacacccg | ggcgggagca | aggtgttccg | catcttccag | gagcgcgacg | 600 |
| cgacggagca | gttcgagtct | taccactcgc | ccaaggccat | caagatgatg | gagggcatgc | 660 |
| tcaagaagtc | ggaggatgcg | cccgcttccg | tgccccctgcc | ctcgcggtcc | accatgggca | 720 |
| cggagttcaa | ggagatgatt | gagcgccaca | agagggctgg | tctctacgac | ccttgcccgt | 780 |
| tggacgagct | gttcaagctc | accatcgtcc | ttgcgcccat | cttcgtgggc | gcctatctcg | 840 |
| tgcggagcgg | cgtctcgccc | ctcgcggcg | cgctctccat | gggctttggc | ttctacctcg | 900 |
| acggctggct | tgctcacrac | tacctgcatc | acgcagtctt | caagggctcg | gtcaacacgc | 960 |
| tcgtcaaggc | gaacaacgcc | atgggatacg | ccctcggctt | cctccagggc | tacgacgtgg | 1020 |
| cctggtggcg | cgcgcgccat | aacacgcacc | acgtgtgcac | caacgaggat | ggttcggacc | 1080 |
| cggacatcaa | gacggcgccc | ctgctcatct | acgtgcgaga | gaacccgtcc | attgccaagc | 1140 |
| ggctcaactt | cttccagcgc | tggcagcagt | actactatgt | gccgaccatg | gccatcctcg | 1200 |
| acctctactg | gcgcctggag | tccatcgcgt | acgtggctgt | gcgcctgcct | aagatgtgga | 1260 |
| tgcaggccgc | gctcttgcc | gctcactacg | cgct | | | 1294 |

<210> SEQ ID NO 64
<211> LENGTH: 1927
<212> TYPE: DNA
<213> ORGANISM: Pavlova lutheri

<400> SEQUENCE: 64

| | | | | | |
|---|---|---|---|---|---|
| ctttgcgagc | gcggcgcaga | cgattgcggc | ccgtagtgat | cgcggtgcgc | attgctgtgt | 60 |
| ttctagtttt | gctgacgccc | ggcccgataa | tgacaccttc | tcccgtttga | aatactaata | 120 |
| agtaactata | ttataatatt | caaaggtggc | gactatggat | ctccttttct | aaagttcagc | 180 |
| ggaattggga | atcggagaaa | tttcgagata | tgtcataatc | acgtgctcta | tctcgaatga | 240 |
| accgcggccg | gtgagcgatt | actcgggaag | ccaattccta | ttaacgagtc | aggggggatc | 300 |
| tttgaggtga | gtcggccacg | cagagagagc | aaggaatcat | cctcatccgc | cgttctcgag | 360 |
| aaagagccaa | gggtgccaac | caccttccac | gtgagactac | acaccgtagg | ccgatgggca | 420 |
| agggtggaga | cggcggcgcg | caggcggtga | gcgggaccga | cgcgtctctc | gctgaggtga | 480 |
| gctccgtcga | tagcaagagc | gtgcacgtcg | tgctctacgg | caagcgcgtg | gatgtcacaa | 540 |
| agttccagaa | ggcacacccg | ggcgggagca | aggtgttccg | catcttccag | gagcgcgacg | 600 |

```
cgacggagca gttcgagtct taccactcgc ccaaggccat caagatgatg gagggcatgc    660
tcaagaagtc ggaggatgcg cccgcttccg tgccctgcc ctcgcggtcc accatgggca    720
cggagttcaa ggagatgatt gagcgccaca gagggctgg tctctacgac ccttgcccgt    780
tggacgagct gttcaagctc accatcgtcc ttgcgccat cttcgtgggc gcctatctcg    840
tgcggagcgg cgtctcgccc ctcgcgggcg cgctctccat gggctttggc ttctacctcg    900
acggctggct tgctcacgac tacctgcatc acgcagtctt caagggctcg gtcaacacgc    960
tcgtcaaggc gaacaacgcc atgggatacg ccctcggctt cctccagggc tacgacgtgg   1020
cctggtggcg cgcgcgccat aacacgcacc acgtgtgcac caacgaggat ggttcggacc   1080
cggacatcaa gacggcgccc ctgctcatct acgtgcgaga gaacccgtcc attgccaagc   1140
ggctcaactt cttccagcgc tggcagcagt actactatgt gccgaccatg gccatcctcg   1200
acctctactg gcgcctggag tccatcgcgt acgtggctgt gcgcctgcct aagatgtgga   1260
tgcaggccgc cgctccttgcc gctcactacg cgctcctgtg ctgggtcttc gcagcgcatc   1320
tcaacctcat ccctctcatg atggttgcac gcggcttcgc gacgggcatc gttgtctttg   1380
caacccacta tggtgaggac atcctcgacc gcgagcacgt cgagggcatg acgctcgtcg   1440
agcagaccgc caagacctcc cgtaacatca cgggcggctg gctagtgaac gtgctcacgg   1500
gcttcatctc cctgcagacc gagcatcacc tcttccccat gatgcccacc ggcaacctaa   1560
tgactatcca gcccgaggta cgcgacttct tcaagaagca tggcctcgag taccgcgagg   1620
gcaacctctt ccagtgcgtg caccagaaca tcaaggctct cgccttcgag cacctcctcc   1680
actgagcgtc accactcaag cgtcctaagt gcacaggtac tgtcttctga ccgatggccg   1740
cgcggctccc tcggctggca gtggggccaa cgagtggcct cgcgggatcg ggcacgatcg   1800
ggcctccatg aaacttcagt gttcagagac aagccgacaa cctccgcatc gtgagaaatc   1860
ttttaaagca gtatgttcca tcacgccgct tttgcagtca ataacattac ccaaaaaaaa   1920
aaaaaaa                                                           1927
```

<210> SEQ ID NO 65
<211> LENGTH: 459
<212> TYPE: PRT
<213> ORGANISM: Rhizopus stolonifer (GenBank Accession No. ABB96724)

<400> SEQUENCE: 65

```
Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Pro Leu
```

```
                130              135              140
Tyr Ala Tyr Gly Arg Thr Ser Thr Leu Ala Val Val Ala Ser Ala Ile
145                 150                  155                 160

Thr Val Gly Ile Phe Trp Gln Gln Cys Gly Trp Leu Ala His Asp Phe
                165                  170                 175

Gly His His Gln Cys Phe Glu Asp Arg Thr Trp Asn Asp Val Leu Val
            180                  185                 190

Val Phe Leu Gly Asn Phe Cys Gln Gly Phe Ser Leu Ser Trp Trp Lys
            195                  200                 205

Asn Lys His Asn Thr His His Ala Ser Thr Asn Val His Gly Gln Asp
210                 215                  220

Pro Asp Ile Asp Thr Ala Pro Val Leu Leu Trp Asp Glu Tyr Ala Ser
225                 230                  235                 240

Ala Ala Tyr Tyr Ala Ser Leu Asp Gln Glu Pro Thr Met Val Ser Arg
                245                  250                 255

Phe Leu Ala Glu Gln Val Leu Pro His Gln Thr Arg Tyr Phe Phe Phe
            260                  265                 270

Ile Leu Ala Phe Ala Arg Leu Ser Trp Ala Leu Gln Ser Leu Ser Tyr
            275                  280                 285

Ser Phe Lys Lys Glu Ser Ile Asn Lys Ser Arg Gln Leu Asn Leu Phe
            290                  295                 300

Glu Arg Val Cys Ile Val Gly His Trp Ala Leu Ser Ala Phe Cys Ile
305                 310                  315                 320

Tyr Ser Trp Cys Ser Asn Val Tyr His Met Val Leu Phe Phe Leu Val
                325                  330                 335

Ser Gln Ala Thr Thr Gly Tyr Thr Leu Ala Leu Val Phe Ala Leu Asn
                340                  345                 350

His Asn Gly Met Pro Val Ile Thr Glu Glu Lys Ala Glu Ser Met Glu
            355                  360                 365

Phe Phe Glu Ile Gln Val Ile Thr Gly Arg Asp Val Thr Leu Ser Pro
            370                  375                 380

Leu Gly Asp Trp Phe Met Gly Gly Leu Asn Tyr Gln Ile Glu His His
385                 390                  395                 400

Val Phe Pro Asn Met Pro Arg His Asn Leu Pro Thr Val Lys Pro Met
                405                  410                 415

Val Lys Ser Leu Cys Gln Lys Tyr Asp Ile Asn Tyr His Asp Thr Gly
            420                  425                 430

Phe Leu Lys Gly Thr Leu Glu Val Leu Gln Thr Leu Asp Ile Thr Ser
            435                  440                 445

Lys Leu Ser Leu Gln Leu Ser Lys Lys Ser Phe
    450                  455

<210> SEQ ID NO 66
<211> LENGTH: 427
<212> TYPE: PRT
<213> ORGANISM: Pavlova salina
<300> PUBLICATION INFORMATION:
<302> TITLE: SYNTHESIS OF LONG-CHAIN POLYUNSATURATED FATTY ACIDS BY
      RECOMBINANT CELLS
<310> PATENT DOCUMENT NUMBER: WO 2005/103253
<311> PATENT FILING DATE: 2005-04-22
<312> PUBLICATION DATE: 2005-11-03
<313> RELEVANT RESIDUES: (1)..(427)

<400> SEQUENCE: 66

Met Gly Arg Gly Gly Asp Ser Ser Gly Gln Ala His Pro Ala Ala Glu
1               5                   10                  15
```

```
Leu Ala Val Pro Ser Asp Arg Ala Glu Val Ser Asn Ala Asp Ser Lys
            20                  25                  30

Ala Leu His Ile Val Leu Tyr Gly Lys Arg Val Asp Val Thr Lys Phe
            35                  40                  45

Gln Arg Thr His Pro Gly Gly Ser Lys Val Phe Arg Ile Phe Gln Asp
            50                  55                  60

Arg Asp Ala Thr Glu Gln Phe Glu Ser Tyr His Ser Lys Arg Ala Ile
 65                  70                  75                  80

Lys Met Met Glu Gly Met Leu Lys Lys Ser Glu Asp Ala Pro Ala Asp
                    85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
            115                 120                 125

Glu Leu Phe Lys Leu Ser Leu Val Leu Leu Pro Thr Phe Ala Gly Met
            130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
            165                 170                 175

His His Ser Val Phe Lys Gly Ser Val Ala Arg Thr Val Gly Trp Asn
            180                 185                 190

Asn Ala Ala Gly Tyr Phe Leu Gly Phe Val Gln Gly Tyr Ala Val Glu
            195                 200                 205

Trp Trp Arg Ala Arg His Asn Thr His His Val Cys Thr Asn Glu Asp
            210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
            245                 250                 255

Gln Tyr Tyr Tyr Val Pro Val Met Ala Ile Leu Asp Leu Tyr Trp Arg
            260                 265                 270

Leu Glu Ser Ile Ala Tyr Val Ala Met Arg Leu Pro Lys Met Leu Pro
            275                 280                 285

Gln Ala Leu Ala Leu Val Ala His Tyr Ala Ile Val Ala Trp Val Phe
            290                 295                 300

Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
            325                 330                 335

Asp Ala Asp Gln Val Arg His Met Thr Leu Val Glu Gln Thr Ala Leu
            340                 345                 350

Thr Ser Arg Asn Ile Ser Gly Gly Trp Leu Val Asn Val Leu Thr Gly
            355                 360                 365

Phe Ile Ser Leu Gln Thr Glu His His Leu Phe Pro Met Met Pro Thr
            370                 375                 380

Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
            405                 410                 415

Asn Ile Arg Ala Leu Ala Phe Glu His Leu Leu
            420                 425
```

<210> SEQ ID NO 67
<211> LENGTH: 1338
<212> TYPE: DNA
<213> ORGANISM: Mortierella alpina

<400> SEQUENCE: 67

```
atgggaacgg accaaggaaa aaccttcacc tgggaagagc tggcggccca taacaccaag      60
gacgacctac tcttggccat ccgcggcagg gtgtacgatg tcacaaagtt cttgagccgc     120
catcctggtg gagtggacac tctcctgctc ggagctggcc gagatgttac tccggtcttt     180
gagatgtatc acgcgtttgg ggctgcagat gccattatga agaagtacta tgtcggtaca     240
ctggtctcga atgagctgcc catcttcccg gagccaacgg tgttccacaa aaccatcaag     300
acgagagtcg agggctactt tacgatcgg aacattgatc ccaagaatag accagagatc      360
tggggacgat acgctcttat ctttggatcc ttgatcgctt cctactacgc gcagctcttt     420
gtgcctttcg ttgtcgaacg cacatggctt caggtggtgt ttgcaatcat catgggattt     480
gcgtgcgcac aagtcggact caaccctctt catgatgcgt ctcactttc agtgacccac      540
aaccccactg tctggaagat tctgggagcc acgcacgact tttcaacgg agcatcgtac      600
ctggtgtgga tgtaccaaca tgctcggc catcacccct acaccaacat gctggagca       660
gatcccgacg tgtcgacgtc tgagcccgat gttcgtcgta tcaagcccaa ccaaaagtgg     720
tttgtcaacc acatcaacca gcacatgttt gttcctttcc tgtacggact gctggcgttc     780
aaggtgcgca ttcaggacat caacattttg tactttgtca agaccaatga cgctattcgt     840
gtcaatccca tctcgacatg gcacactgtg atgttctggg gcggcaaggc tttctttgtc     900
tggtatcgcc tgattgttcc cctgcagtat ctgcccctgg caaggtgct gctcttgttc      960
acggtcgcgg acatggtgtc gtcttactgg ctggcgctga ccttccaggc gaaccacgtt    1020
gttgaggaag ttcagtggcc gttgcctgac gagaacggga tcatccaaaa ggactgggca    1080
gctatgcagg tcgagactac gcaggattac gcacacgatt cgcacctctg gaccagcatc    1140
actggcagct tgaactacca ggctgtgcac catctgttcc ccaacgtgtc gcagcaccat    1200
tatcccgata ttctggccat catcaagaac acctgcagcg agtacaaggt tccataccct    1260
gtcaaggata cgttttggca agcatttgct tcacatttgg agcacttgcg tgttcttgga    1320
ctccgtccca aggaagag                                                   1338
```

<210> SEQ ID NO 68
<211> LENGTH: 446
<212> TYPE: PRT
<213> ORGANISM: Mortierella alpina

<400> SEQUENCE: 68

```
Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95
```

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
            115                 120                 125

Gly Ser Leu Ile Ala Ser Tyr Tyr Ala Gln Leu Phe Val Pro Phe Val
            130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
            165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
            195                 200                 205

Leu Gly His His Pro Tyr Thr Asn Ile Ala Gly Ala Asp Pro Asp Val
            210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
            245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
            275                 280                 285

Thr Val Met Phe Trp Gly Gly Lys Ala Phe Phe Val Trp Tyr Arg Leu
            290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
            325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
            355                 360                 365

Asp Tyr Ala His Asp Ser His Leu Trp Thr Ser Ile Thr Gly Ser Leu
            370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
            405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
            435                 440                 445

<210> SEQ ID NO 69
<211> LENGTH: 6473
<212> TYPE: DNA
<213> ORGANISM: Artificial Sequence
<220> FEATURE:
<223> OTHER INFORMATION: Plasmid pY5-22

<400> SEQUENCE: 69
ggtggagctc cagcttttgt tccctttagt gagggttaat ttcgagcttg gcgtaatcat      60

```
ggtcatagct gtttcctgtg tgaaattgtt atccgctcac aattccacac aacgtacgag    120
ccggaagcat aaagtgtaaa gcctggggtg cctaatgagt gagctaactc acattaattg    180
cgttgcgctc actgcccgct ttccagtcgg gaaacctgtc gtgccagctg cattaatgaa    240
tcggccaacg cgcggggaga ggcggttttg cgtattgggcg ctcttccgct tcctcgctca    300
ctgactcgct gcgctcggtc gttcggctgc ggcgagcggt atcagctcac tcaaaggcgg    360
taatacggtt atccacagaa tcaggggata acgcaggaaa gaacatgtga gcaaaaggcc    420
agcaaaaggc caggaaccgt aaaaaggccg cgttgctggc gtttttccat aggctccgcc    480
cccctgacga gcatcacaaa aatcgacgct caagtcagag gtggcgaaac ccgacaggac    540
tataaagata ccaggcgttt ccccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg ggctgtgtgc    720
acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaaggacagt atttggtatc tgcgctctgc tgaagccagt taccttcgga aaaagagttg    960
gtagctcttg atccggcaaa caaaccaccg ctggtagcgg tggtttttt gtttgcaagc    1020 agcagattac gcgcagaaaa aaaggatctc aagaagatcc tttgatcttt tctacggggt    1080
ctgacgctca gtggaacgaa aactcacgtt aagggatttt ggtcatgaga ttatcaaaaa    1140
ggatcttcac ctagatcctt ttaaattaaa aatgaagttt taaatcaatc taaagtatat    1200
atgagtaaac ttggtctgac agttaccaat gcttaatcag tgaggcacct atctcagcga    1260
tctgtctatt tcgttcatcc atagttgcct gactccccgt cgtgtagata actacgatac    1320
gggagggctt accatctggc cccagtgctg caatgatacc gcgagaccca cgctcaccgg    1380
ctccagattt atcagcaata aaccagccag ccggaagggc cgagcgcaga agtggtcctg    1440
caactttatc cgcctccatc cagtctatta attgttgccg ggaagctaga gtaagtagtt    1500
cgccagttaa tagtttgcgc aacgttgttg ccattgctac aggcatcgtg gtgtcacgct    1560
cgtcgtttgg tatggcttca ttcagctccg gttcccaacg atcaaggcga gttacatgat    1620
cccccatgtt gtgcaaaaaa gcggttagct ccttcggtcc tccgatcgtt gtcagaagta    1680
agttggccgc agtgttatca ctcatggtta tggcagcact gcataattct cttactgtca    1740
tgccatccgt aagatgcttt tctgtgactg gtgagtactc aaccaagtca ttctgagaat    1800
agtgtatgcg gcgaccgagt tgctcttgcc cggcgtcaat acgggataat accgcgccac    1860
atagcagaac tttaaaagtg ctcatcattg gaaaacgttc ttcggggcga aaactctcaa    1920
ggatcttacc gctgttgaga tccagttcga tgtaacccac tcgtgcaccc aactgatctt    1980
cagcatcttt tactttcacc agcgtttctg ggtgagcaaa aacaggaagg caaaatgccg    2040
caaaaaaggg aataagggcg acacggaaat gttgaatact catactcttc ctttttcaat    2100
attattgaag catttatcag ggttattgtc tcatgagcgg atacatattt gaatgtattt    2160
agaaaaataa acaaataggg gttccgcgca catttccccg aaaagtgcca cctgacgcgc    2220
cctgtagcgg cgcattaagc gcggcgggtg tggtggttac gcgcagcgtg accgctacac    2280
ttgccagcgc cctagcgccc gctcctttcg ctttcttccc ttcctttctc gccacgttcg    2340 ccggcttttcc ccgtcaagct ctaaatcggg ggctcccttt agggttccga tttagtgctt    2400
tacggcacct cgaccccaaa aaacttgatt agggtgatgg ttcacgtagt gggccatcgc    2460
```

```
cctgatagac ggttttttcgc cctttgacgt tggagtccac gttctttaat agtggactct    2520
tgttccaaac tggaacaaca ctcaacccta tctcggtcta ttcttttgat ttataaggga    2580
ttttgccgat tcggcctat tggttaaaaa atgagctgat ttaacaaaaa tttaacgcga     2640
attttaacaa atattaacg cttacaattt ccattcgcca ttcaggctgc gcaactgttg     2700
ggaagggcga tcggtgcggg cctcttcgct attacgccag ctggcgaaag ggggatgtgc    2760
tgcaaggcga ttaagttggg taacgccagg ttttcccag tcacgacgtt gtaaaacgac     2820
ggccagtgaa ttgtaatacg actcactata gggcgaattg ggtaccgggc cccccctcga    2880
ggtcgatggt gtcgataagc ttgatatcga attcatgtca cacaaaccga tcttcgcctc    2940
aaggaaacct aattctacat ccgagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatattta aggggtcatc tcgcattgtt taataataaa cagactccat    3180
ctaccgcctc caaatgatgt tctcaaaata tattgtatga acttattttt attacttagt    3240
attattagac aacttacttg ctttatgaaa aacacttcct atttaggaaa caatttataa    3300
tggcagttcg ttcatttaac aatttatgta gaataaatgt tataaatgcg tatgggaaat    3360
cttaaatatg gatagcataa atgatatctg cattgcctaa ttcgaaatca acagcaacga    3420
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttattttt attctaatga tccattaaag gtatatattt atttcttgtt    3780
atataatcct tttgtttatt acatgggctg gatacataaa ggtattttga tttaattttt    3840
tgcttaaatt caatccccccc tcgttcagtg tcaactgtaa tggtaggaaa ttaccatact    3900
tttgaagaag caaaaaaat gaaagaaaaa aaaaatcgta tttccaggtt agacgttccg     3960
cagaatctag aatgcggtat gcggtacatt gttcttcgaa cgtaaaagtt gcgctccctg    4020
agatattgta cattttgct tttacaagta caagtacatc gtacaactat gtactactgt     4080
tgatgcatcc acaacagttt gttttgtttt ttttgtttt ttttttttct aatgattcat     4140
taccgctatg tatacctact tgtacttgta gtaagccggg ttattggcgt tcaattaatc    4200
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
ttaattaagt catacacaag tcagctttct tcgagcctca tataagtata agtagttcaa    4380
cgtattagca ctgtacccag catctccgta tcgagaaaca caacaacatg ccccattgga    4440
cagatcatgc ggatacacag gttgtgcagt atcatacata ctcgatcaga caggtcgtct    4500
gaccatcata caagctgaac aagcgctcca tacttgcacg ctctctatat acacagttaa    4560
attacatatc catagtctaa cctctaacag ttaatcttct ggtaagcctc ccagccagcc    4620
ttctggtatc gcttggcctc ctcaatagga tctcggttct ggccgtacag acctcggccg    4680
acaattatga tatccgttcc ggtagacatg acatcctcaa cagttcggta ctgctgtccg    4740
agagcgtctc ccttgtcgtc aagacccacc ccggggtca gaataagcca gtcctcagag     4800
```

```
tcgcccttag gtcggttctg ggcaatgaag ccaaccacaa actcggggtc ggatcgggca    4860
agctcaatgg tctgcttgga gtactcgcca gtggccagag agcccttgca agacagctcg    4920
gccagcatga gcagacctct ggccagcttc tcgttgggag aggggactag gaactccttg    4980
tactgggagt tctcgtagtc agagacgtcc tccttcttct gttcagagac agtttcctcg    5040
gcaccagctc gcaggccagc aatgattccg gttccgggta caccgtgggc gttggtgata    5100
tcggaccact cggcgattcg gtgacaccgg tactggtgct tgacagtgtt gccaatatct    5160
gcgaactttc tgtcctcgaa caggaagaaa ccgtgcttaa gcaagttc cttgaggggg     5220 agcacagtgc cggcgtaggt gaagtcgtca atgatgtcga tatgggtttt gatcatgcac    5280
acataaggtc cgaccttatc ggcaagctca atgagctcct tggtggtggt aacatccaga    5340
gaagcacaca ggttggtttt cttggctgcc acgagcttga gcactcgagc ggcaaaggcg    5400
gacttgtgga cgttagctcg agcttcgtag gagggcattt tggtggtgaa gaggagactg    5460
aaataaattt agtctgcaga acttttatc ggaaccttat ctgggcagt gaagtatatg      5520 ttatggtaat agttacgagt tagttgaact tatagataga ctggactata cggctatcgg    5580
tccaaattag aaagaacgtc aatggctctc tgggcgtcgc ctttgccgac aaaaatgtga    5640
tcatgatgaa agccagcaat gacgttgcag ctgatattgt tgtcggccaa ccgcgccgaa    5700
aacgcagctg tcagacccac agcctccaac gaagaatgta tcgtcaaagt gatccaagca    5760
cactcatagt tggagtcgta ctccaaaggc ggcaatgacg agtcagacag atactcgtcg    5820
actcaggcga cgacggaatt cctgcagccc atctgcagaa ttcaggagag accgggttgg    5880
cggcgtattt gtgtcccaaa aaacagcccc aattgcccca attgacccca aattgaccca    5940
gtagcgggcc caaccccggc gagagccccc ttcaccccac atatcaaacc tcccccggtt    6000
cccacacttg ccgttaaggg cgtagggtac tgcagtctgg aatctacgct tgttcagact    6060
ttgtactagt ttctttgtct ggccatccgg gtaacccatg ccggacgcaa atagactac    6120 tgaaaatttt tttgctttgt ggttgggact ttagccaagg gtataaaaga ccaccgtccc    6180
cgaattacct ttcctcttct tttctctctc tccttgtcaa ctcacacccg aaatcgttaa    6240
gcatttcctt ctgagtataa gaatcattca ccatggatcc actagttcta gagcggccgc    6300
caccgcggcc cgagattccg gcctcttcgg ccgccaagcg acccgggtgg acgtctagag    6360
gtacctagca attaacagat agtttgccgg tgataattct cttaacctcc cacactcctt    6420
tgacataacg atttatgtaa cgaaactgaa atttgaccag atattgtgtc cgc           6473
```

<210> SEQ ID NO 70
<211> LENGTH: 6970
<212> TYPE: DNA
<213> ORGANISM: Artificial Sequence
<220> FEATURE:
<223> OTHER INFORMATION: Plasmid pY5-22GPD

<400> SEQUENCE: 70

```
tcgacgcagt aggatgtcct gcacgggtct ttttgtgggg tgtggagaaa ggggtgcttg      60
gagatggaag ccgtagaac cgggctgctt gtgcttggag atggaagccg gtagaaccgg      120
gctgcttggg gggatttggg gccgctgggc tccaagagg ggtaggcatt tcgttggggt     180
tacgtaattg cggcatttgg gtcctgcgcg catgtcccat tggtcagaat tagtccggat     240
aggagactta tcagccaatc acagcgccgg atccacctgt aggttgggtt gggtgggagc     300
acccctccac agagtagagt caaacagcag cagcaacatg atagttgggg gtgtgcgtgt     360
taaaggaaaa aaaagaagct tgggttatat tcccgctcta tttagaggtt gcgggataga    420
```

```
cgccgacgga gggcaatggc gccatggaac cttgcggata tcgatacgcc gcggcggact    480
gcgtccgaac cagctccagc agcgttttt ccgggccatt gagccgactg cgaccccgcc    540
aacgtgtctt ggcccacgca ctcatgtcat gttggtgttg ggaggccact ttttaagtag    600
cacaaggcac ctagctcgca gcaaggtgtc cgaaccaaag aagcggctgc agtggtgcaa    660
acggggcgga acggcggga aaagccacg ggggcacgaa ttgaggcacg ccctcgaatt    720
tgagacgagt cacggcccca ttcgcccgcg caatggctcg ccaacgcccg gtcttttgca    780
ccacatcagg ttaccccaag ccaaacccttt gtgttaaaaa gcttaacata ttataccgaa    840
cgtaggtttg ggcgggcttg ctccgtctgt ccaaggcaac atttatataa gggtctgcat    900
cgccggctca attgaatctt ttttcttctt ctcttctcta tattcattct tgaattaaac    960
acacatcaat ccgcggccgc caccgcggcc cgagattccg gcctcttcgg ccgccaagcg   1020
acccgggtgg acgtctagag gtacctagca attaacagat agtttgccgg tgataattct   1080
cttaacctcc cacactcctt tgacataacg atttatgtaa cgaaactgaa atttgaccag   1140
atattgtgtc cgcggtggag ctccagcttt tgttcccttt agtgagggtt aatttcgagc   1200
ttggcgtaat catggtcata gctgtttcct gtgtgaaatt gttatccgct cacaattcca   1260
cacaacgtac gagccggaag cataaagtgt aaagcctggg gtgcctaatg agtgagctaa   1320
ctcacattaa ttgcgttgcg ctcactgccc gctttccagt cgggaaacct gtcgtgccag   1380
ctgcattaat gaatcggcca acgcgcgggg agaggcggtt tgcgtattgg gcgctcttcc   1440
gcttcctcgc tcactgactc gctgcgctcg gtcgttcggc tgcggcgagc ggtatcagct   1500
cactcaaagg cggtaatacg gttatccaca gaatcagggg ataacgcagg aaagaacatg   1560
tgagcaaaag gccagcaaaa ggccaggaac cgtaaaaagg ccgcgttgct ggcgtttttc   1620
cataggctcc gcccccctga cgagcatcac aaaaatcgac gctcaagtca gaggtggcga   1680
aacccgacag gactataaag ataccaggcg tttccccctg gaagctccct cgtgcgctct   1740
cctgttccga ccctgccgct taccggatac ctgtccgcct ttctcccttc gggaagcgtg   1800
gcgctttctc atagctcacg ctgtaggtat ctcagttcgg tgtaggtcgt tcgctccaag   1860
ctgggctgtg tgcacgaacc ccccgttcag cccgaccgct gcgccttatc cggtaactat   1920
cgtcttgagt ccaacccggt aagacacgac ttatcgccac tggcagcagc cactggtaac   1980
aggattagca gagcgaggta tgtaggcggt gctacagagt tcttgaagtg gtggcctaac   2040
tacggctaca ctagaaggac agtatttggt atctgcgctc tgctgaagcc agttaccttc   2100
ggaaaaagag ttggtagctc ttgatccggc aaacaaacca ccgctggtag cggtggtttt   2160
tttgtttgca agcagcagat tacgcgcaga aaaaaaggat ctcaagaaga tcctttgatc   2220
ttttctacgg ggtctgacgc tcagtggaac gaaaactcac gttaagggat tttggtcatg   2280
agattatcaa aaaggatctt cacctagatc cttttaaatt aaaaatgaag ttttaaatca   2340
atctaaagta tatatgagta aacttggtct gacagttacc aatgcttaat cagtgaggca   2400
cctatctcag cgatctgtct atttcgttca tccatagttg cctgactccc cgtcgtgtag   2460
ataactacga tacgggaggg cttaccatct ggccccagtg ctgcaatgat accgcgagac   2520
ccacgctcac cggctccaga tttatcagca ataaaccagc cagccggaag ggccgagcgc   2580
agaagtggtc ctgcaacttt atccgcctcc atccagtcta ttaattgttg ccgggaagct   2640
agagtaagta gttcgccagt taatagtttg cgcaacgttg ttgccattgc tacaggcatc   2700
gtggtgtcac gctcgtcgtt tggtatggct tcattcagct ccggttccca acgatcaagg   2760
```

```
cgagttacat gatcccccat gttgtgcaaa aaagcggtta gctccttcgg tcctccgatc    2820
gttgtcagaa gtaagttggc cgcagtgtta tcactcatgg ttatggcagc actgcataat    2880
tctcttactg tcatgccatc cgtaagatgc ttttctgtga ctggtgagta ctcaaccaag    2940
tcattctgag aatagtgtat gcggcgaccg agttgctctt gcccggcgtc aatacgggat    3000
aataccgcgc cacatagcag aactttaaaa gtgctcatca ttggaaaacg ttcttcgggg    3060
cgaaaactct caaggatctt accgctgttg agatccagtt cgatgtaacc cactcgtgca    3120
cccaactgat cttcagcatc ttttactttc accagcgttt ctgggtgagc aaaaacagga    3180
aggcaaaatg ccgcaaaaaa gggaataagg gcgacacgga atgttgaat actcatactc     3240 ttcctttttc aatattattg aagcatttat cagggttatt gtctcatgag cggatacata    3300
tttgaatgta tttagaaaaa taaacaaata ggggttccgc gcacatttcc ccgaaaagtg    3360
ccacctgacg cgccctgtag cggcgcatta agcgcggcgg gtgtggtggt tacgcgcagc    3420
gtgaccgcta cacttgccag cgccctagcg cccgctcctt tcgctttctt cccttccttt    3480
ctcgccacgt tcgccggctt tccccgtcaa gctctaaatc gggggctccc tttagggttc    3540
cgatttagtg ctttacggca cctcgacccc aaaaaacttg attagggtga tggttcacgt    3600
agtgggccat cgccctgata cggttttt cgccctttga cgttggagtc cacgttcttt     3660
aatagtggac tcttgttcca aactggaaca acactcaacc ctatctcggt ctattctttt    3720
gatttataag ggattttgcc gatttcggcc tattggttaa aaatgagct gatttaacaa     3780 aaatttaacg cgaattttaa caaaatatta acgcttacaa tttccattcg ccattcaggc    3840
tgcgcaactg ttgggaaggg cgatcggtgc gggcctcttc gctattacgc cagctggcga    3900
aagggggatg tgctgcaagg cgattaagtt gggtaacgcc agggttttcc cagtcacgac    3960
gttgtaaaac gacggccagt gaattgtaat acgactcact atagggcgaa ttgggtaccg    4020
ggccccccct cgaggtcgat ggtgtcgata agcttgatat cgaattcatg tcacacaaac    4080
cgatcttcgc ctcaaggaaa cctaattcta catccgagag actgccgaga tccagtctac    4140
actgattaat tttcgggcca ataatttaaa aaaatcgtgt tatataatat tatatgtatt    4200
atatatatac atcatgatga tactgacagt catgtcccat tgctaaatag acagactcca    4260
tctgccgcct ccaactgatg ttctcaatat ttaaggggtc atctcgcatt gtttaataat    4320
aaacagactc catctaccgc ctccaaatga tgttctcaaa atatattgta tgaacttatt    4380
tttattactt agtattatta gacaacttac ttgctttatg aaaaacactt cctatttagg    4440
aaacaattta taatggcagt tcgttcattt aacaatttat gtagaataaa tgttataaat    4500
gcgtatggga atcttaaat atggatagca taaatgatat ctgcattgcc taattcgaaa     4560
tcaacagcaa cgaaaaaaat cccttgtaca acataaatag tcatcgagaa atatcaacta    4620
tcaaagaaca gctattcaca cgttactatt gagattatta ttggacgaga atcacacact    4680
caactgtctt tctctcttct agaaatacag gtacaagtat gtactattct cattgttcat    4740
acttctagtc atttcatccc acatattcct tggatttctc tccaatgaat gacattctat    4800
cttgcaaatt caacaattat aataagatat accaaagtag cggtatagtg gcaatcaaaa    4860
agcttctctg gtgtgcttct cgtatttatt tttattctaa tgatccatta aggtatata     4920 tttatttctt gttatataat cctttgtttt attacatggg ctggatacat aaaggtatt     4980 tgatttaatt ttttgcttaa attcaatccc ccctcgttca gtgtcaactg taatggtagg    5040
aaattaccat acttttgaag aagcaaaaaa aatgaaagaa aaaaaaaatc gtatttccag    5100
gttagacgtt ccgcagaatc tagaatgcgg tatgcggtac attgttcttc gaacgtaaaa    5160
```

-continued

```
gttgcgctcc ctgagatatt gtacattttt gcttttacaa gtacaagtac atcgtacaac   5220
tatgtactac tgttgatgca tccacaacag tttgttttgt ttttttttgt ttttttttt    5280 tctaatgatt cattaccgct atgtatacct acttgtactt gtagtaagcc gggttattgg   5340
cgttcaatta atcatagact tatgaatctg cacggtgtgc gctgcgagtt acttttagct   5400
tatgcatgct acttgggtgt aatattggga tctgttcgga aatcaacgga tgctcaaccg   5460
atttcgacag taattaatta agtcatacac aagtcagctt tcttcgagcc tcatataagt   5520
ataagtagtt caacgtatta gcactgtacc cagcatctcc gtatcgagaa acacaacaac   5580
atgccccatt ggacagatca tgcggataca caggttgtgc agtatcatac atactcgatc   5640
agacaggtcg tctgaccatc atacaagctg aacaagcgct ccatacttgc acgtctcta   5700 tatacacagt taaattacat atccatagtc taacctctaa cagttaatct tctggtaagc   5760
ctcccagcca gccttctggt atcgcttggc ctcctcaata ggatctcggt tctggccgta   5820
cagacctcgg ccgacaatta tgatatccgt tccggtagac atgacatcct caacagttcg   5880
gtactgctgt ccgagagcgt ctcccttgtc gtcaagaccc accccggggg tcagaataag   5940
ccagtcctca gagtcgccct taggtcggtt ctgggcaatg aagccaacca caaactcggg   6000
gtcggatcgg gcaagctcaa tggtctgctt ggagtactcg ccagtggcca gagagcccett  6060 gcaagacagc tcggccagca tgagcagacc tctggccagc ttctcgttgg gagaggggac   6120
taggaactcc ttgtactggg agttctcgta gtcagagacg tcctccttct tctgttcaga   6180
gacagtttcc tcggcaccag ctcgcaggcc agcaatgatt ccggttccgg gtacaccgtg   6240
ggcgttggtg atatcggacc actcggcgat tcggtgacac cggtactggt gcttgacagt   6300
gttgccaata tctgcgaact ttctgtcctc gaacaggaag aaaccgtgct taagagcaag   6360
ttccttgagg gggagcacag tgccggcgta ggtgaagtcg tcaatgatgt cgatatgggt   6420
tttgatcatg cacacataag gtccgacctt atcggcaagc tcaatgagct ccttggtggt   6480
ggtaacatcc agagaagcac acaggttggt tttcttggct gccacgagct tgagcactcg   6540
agcggcaaag gcggacttgt ggacgttagc tcgagcttcg taggagggca ttttggtggt   6600
gaagaggaga ctgaaataaa tttagtctgc agaactttt atcggaacct tatctggggc    6660
agtgaagtat atgttatggt aatagttacg agttagttga acttatagat agactggact   6720
atacggctat cggtccaaat tagaaagaac gtcaatggct ctctgggcgt cgcctttgcc   6780
gacaaaaatg tgatcatgat gaaagccagc aatgacgttg cagctgatat tgttgtcggc   6840
caaccgcgcc gaaaacgcag ctgtcagacc cacagcctcc aacgaagaat gtatcgtcaa   6900
agtgatccaa gcacactcat agttggagtc gtactccaaa ggcggcaatg acgagtcaga   6960
cagatactcg                                                          6970
```

<210> SEQ ID NO 71
<211> LENGTH: 968
<212> TYPE: DNA
<213> ORGANISM: Yarrowia lipolytica
<300> PUBLICATION INFORMATION:
<302> TITLE: GLYCERALDEHYDE-3-PHOSPHATE DEHYDROGENASE AND
    PHOSPHOGLYCERATE MUTASE PROMOTERS FOR GENE EXPRESSION IN
    OLEAGINOUS YEAST
<310> PATENT DOCUMENT NUMBER: US-2005-0014270-A1
<311> PATENT FILING DATE: 2004-06-16
<312> PUBLICATION DATE: 2005-01-20
<313> RELEVANT RESIDUES: (1)..(968)

<400> SEQUENCE: 71

```
tcgacgcagt aggatgtcct gcacgggtct ttttgtgggg tgtggagaaa ggggtgcttg      60
gagatggaag ccggtagaac cgggctgctt gtgcttggag atggaagccg gtagaaccgg     120
gctgcttggg gggatttggg gccgctgggc tccaaagagg ggtaggcatt tcgttgggt     180 tacgtaattg cggcatttgg gtcctgcgcg catgtcccat tggtcagaat tagtccggat     240
aggagactta tcagccaatc acagcgccgg atccacctgt aggttgggtt gggtgggagc     300 accectccac agagtagagt caaacagcag cagcaacatg atagttgggg gtgtgcgtgt     360
taaaggaaaa aaaagaagct tgggttatat tcccgctcta tttagaggtt gcgggataga     420
cgccgacgga gggcaatggc gccatggaac cttgcggata tcgatacgcc gcggcggact     480
gcgtccgaac cagctccagc agcgtttttt ccgggccatt gagccgactg cgaccccgcc     540
aacgtgtctt ggcccacgca ctcatgtcat gttggtgttg ggaggccact ttttaagtag     600
cacaaggcac ctagctcgca gcaaggtgtc cgaaccaaag aagcggctgc agtggtgcaa     660
acggggcgga acggcggga aaaagccacg ggggcacgaa ttgaggcacg ccctcgaatt     720
tgagacgagt cacggcccca ttcgcccgcg caatggctcg ccaacgcccg gtcttttgca     780
ccacatcagg ttaccccaag ccaaacccttt gtgttaaaaa gcttaacata ttataccgaa     840
cgtaggtttg ggcgggcttg ctccgtctgt ccaaggcaac atttatataa gggtctgcat     900
cgccggctca attgaatctt ttttcttcttc ctcttctcta tattcattct tgaattaaac     960
acacatca                                                             968

<210> SEQ ID NO 72
<211> LENGTH: 8630
<212> TYPE: DNA
<213> ORGANISM: Artificial Sequence
<220> FEATURE:
<223> OTHER INFORMATION: Plasmid pYZDE2-S

<400> SEQUENCE: 72
ggtggagctc cagcttttgt tccctttagt gagggttaat tcgagcttgg cgtaatcat      60 ggtcatagct gtttcctgtg tgaaattgtt atccgctcac aattccacac aacgtacgag    120
ccggaagcat aaagtgtaaa gcctggggtg cctaatgagt gagctaactc acattaattg    180
cgttgcgctc actgcccgct ttccagtcgg gaaacctgtc gtgccagctg cattaatgaa    240
tcggccaacg cgcggggaga ggcggtttgc gtattgggcg ctcttccgct tcctcgctca    300
ctgactcgct gcgctcggtc gttcggctgc ggcgagcggt atcagctcac tcaaaggcgg    360
taatacggtt atccacagaa tcaggggata acgcaggaaa gaacatgtga gcaaaaggcc    420
agcaaaaggc caggaaccgt aaaaaggccg cgttgctggc gtttttccat aggctccgcc    480
cccctgacga gcatcacaaa aatcgacgct caagtcagag gtggcgaaac ccgacaggac    540
tataaagata ccaggcgttt ccccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg ggctgtgtgc    720
acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaaggacagt atttggtatc tgcgctctgc tgaagccagt taccttcgga aaaagagttg    960
gtagctcttg atccggcaaa caaaccaccg ctggtagcgg tggtttttttt gtttgcaagc   1020 agcagattac gcgcagaaaa aaaggatctc aagaagatcc tttgatcttt tctacggggt   1080
```

```
ctgacgctca gtggaacgaa aactcacgtt aagggatttt ggtcatgaga ttatcaaaaa    1140
ggatcttcac ctagatcctt ttaaattaaa aatgaagttt taaatcaatc taaagtatat    1200
atgagtaaac ttggtctgac agttaccaat gcttaatcag tgaggcacct atctcagcga    1260
tctgtctatt tcgttcatcc atagttgcct gactccccgt cgtgtagata actacgatac    1320
gggagggctt accatctggc cccagtgctg caatgatacc gcgagaccca cgctcaccgg    1380
ctccagattt atcagcaata aaccagccag ccggaagggc cgagcgcaga agtggtcctg    1440
caactttatc cgcctccatc cagtctatta attgttgccg ggaagctaga gtaagtagtt    1500
cgccagttaa tagtttcgc aacgttgttg ccattgctac aggcatcgtg gtgtcacgct    1560
cgtcgtttgg tatggcttca ttcagctccg gttcccaacg atcaaggcga gttacatgat    1620
cccccatgtt gtgcaaaaaa gcggttagct ccttcggtcc tccgatcgtt gtcagaagta    1680
agttggccgc agtgttatca ctcatggtta tggcagcact gcataattct cttactgtca    1740
tgccatccgt aagatgcttt tctgtgactg gtgagtactc aaccaagtca ttctgagaat    1800
agtgtatgcg gcgaccgagt tgctcttgcc cggcgtcaat acgggataat accgcgccac    1860
atagcagaac tttaaaagtg ctcatcattg gaaaacgttc ttcggggcga aaactctcaa    1920
ggatcttacc gctgttgaga tccagttcga tgtaacccac tcgtgcaccc aactgatctt    1980
cagcatcttt tactttcacc agcgtttctg ggtgagcaaa aacaggaagg caaaatgccg    2040
caaaaaaggg aataagggcg acacggaaat gttgaatact catactcttc ctttttcaat    2100
attattgaag catttatcag ggttattgtc tcatgagcgg atacatattt gaatgtattt    2160
agaaaaataa acaaataggg gttccgcgca catttccccg aaaagtgcca cctgacgcgc    2220
cctgtagcgg cgcattaagc gcggcgggtg tggtggttac gcgcagcgtg accgctacac    2280
ttgccagcgc cctagcgccc gctcctttcg ctttcttccc ttcctttctc gccacgttcg    2340
ccggctttcc ccgtcaagct ctaaatcggg ggctcccttt agggttccga tttagtgctt    2400
tacggcacct cgaccccaaa aaacttgatt agggtgatgg ttcacgtagt gggccatcgc    2460
cctgatagac ggtttttcgc cctttgacgt tggagtccac gttctttaat agtggactct    2520
tgttccaaac tggaacaaca ctcaaccta tctcggtcta ttcttttgat ttataaggga    2580
ttttgccgat ttcggcctat tggttaaaaa atgagctgat ttaacaaaaa tttaacgcga    2640
attttaacaa aatattaacg cttacaattt ccattcgcca ttcaggctgc gcaactgttg    2700
ggaagggcga tcggtgcggg cctcttcgct attacgccag ctggcgaaag ggggatgtgc    2760
tgcaaggcga ttaagttggg taacgccagg gttttcccag tcacgacgtt gtaaaacgac    2820
ggccagtgaa ttgtaatacg actcactata gggcgaattg ggtaccgggc cccccctcga    2880
ggtcgatggt gtcgataagc ttgatatcga attcatgtca cacaaaccga tcttcgcctc    2940
aaggaaacct aattctacat ccagagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatattta aggggtcatc tcgcattgtt taataataaa cagactccat    3180
ctaccgcctc caaatgatgt tctcaaaata tattgtatga acttattttt attacttagt    3240
attattagac aacttacttg ctttatgaaa aacacttcct atttaggaaa caatttataa    3300
tggcagttcg ttcatttaac aatttatgta gaataaatgt tataaatgcg tatgggaaat    3360
cttaaatatg gatagcataa atgatatctg cattgcctaa ttcgaaatca acagcaacga    3420
```

```
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttattttt attctaatga tccattaaag gtatatattt atttcttgtt    3780
atataatcct tttgtttatt acatgggctg gatacataaa ggtattttga tttaattttt    3840
tgcttaaatt caatcccccc tcgttcagtg tcaactgtaa tggtaggaaa ttaccatact    3900
tttgaagaag caaaaaaaat gaaagaaaaa aaaaatcgta tttccaggtt agacgttccg    3960
cagaatctag aatgcggtat gcggtacatt gttcttcgaa cgtaaaagtt gcgctccctg    4020
agatattgta catttttgct tttacaagta caagtacatc gtacaactat gtactactgt    4080
tgatgcatcc acaacagttt gttttgtttt ttttgtttt tttttttct aatgattcat    4140
taccgctatg tatacctact tgtacttgta gtaagccggg ttattggcgt tcaattaatc    4200
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
taatttgaat cgaatcggag cctaaaatga acccgagtat atctcataaa attctcggtg    4380
agaggtctgt gactgtcagt acaaggtgcc ttcattatgc cctcaacctt accatacctc    4440
actgaatgta gtgtacctct aaaaatgaaa tacagtgcca aaagccaagg cactgagctc    4500
gtctaacgga cttgatatac aaccaattaa aacaaatgaa aagaaataca gttctttgta    4560
tcatttgtaa caattaccct gtacaaacta aggtattgaa atcccacaat attcccaaag    4620
tccaccccctt tccaaattgt catgcctaca actcatatac caagcactaa cctaccaaac    4680
accactaaaa ccccacaaaa tatatcttac cgaatataca gtaacaagct accaccacac    4740
tcgttgggtg cagtcgccag cttaaagata tctatccaca tcagccacaa ctcccttcct    4800
ttaataaacc gactcaccc ttggctattg aggttatgag tgaatatact gtagacaaga    4860
cactttcaag aagactgttt ccaaaacgta ccactgtcct ccactacaaa cacacccaat    4920
ctgcttcttc tagtcaaggt tgctacaccg gtaaattata aatcatcatt tcattagcag    4980
ggcagggccc ttttttataga gtcttataca ctagcggacc ctgccggtag accaacccgc    5040
aggcgcgtca gtttgctcct tccatcaatg cgtcgtagaa acgacttact ccttcttgag    5100
cagctccttg accttgttgg caacaagtct ccgacctcgg aggtggagga agagcctccg    5160
atatcggcgg tagtgatacc agcctcgacg gactccttga cggcagcctc aacagcgtca    5220
ccggcgggct tcatgttaag agagaacttg agcatcatgg cggcagacag aatggtggca    5280
atggggttga ccttctgctt gccgagatcg ggggcagatc cgtgacaggg ctcgtacaga    5340
ccgaacgcct cgttggtgtc gggcagagaa gccagagagg cggagggcag cagacccaga    5400
gaaccgggga tgacggaggc ctcgtcggag atgatatcgc caaacatgtt ggtggtgatg    5460
atgataccat tcatcttgga gggctgcttg atgaggatca tggcggccga gtcgatcagc    5520
tggtggttga gctcgagctg ggggaattcg tccttgagga ctcgagtgac agtctttcgc    5580
caaagtcgag aggaggccag cacgttggcc ttgtcaagag accacacggg aagagggggg    5640
ttgtgctgaa gggccaggaa ggcggccatt cgggcaattc gctcaacctc aggaacggag    5700
taggtctcgg tgtcggaagc gacgccagat ccgtcatcct cctttcgctc tccaaagtag    5760
atacctccga cgagctctcg gacaatgatg aagtcggtgc cctcaacgtt tcggatgggg    5820
```

```
gagagatcgg cgagcttggg cgacagcagc tggcagggtc gcaggttggc gtacaggttc   5880
aggtcctttc gcagcttgag gagaccctgc tcgggtcgca cgtcggttcg tccgtcggga   5940
gtggtccata cggtgttggc agcgcctccg acagcaccga gcataataga gtcagccttt   6000
cggcagatgt cgagagtagc gtcggtgatg ggctcgccct ccttctcaat ggcagctcct   6060
ccaatgagtc ggtcctcaaa cacaaactcg gtgccgagg cctcagcaac agacttgagc    6120
accttgacgg cctcggcaat cacctcgggg ccacagaagt cgccgccgag aagaacaatc   6180
ttcttggagt cagtcttggt cttcttagtt tcgggttcca ttgtggatgt gtgtggttgt   6240
atgtgtgatg tggtgtgtgg agtgaaaatc tgtggctggc aaacgctctt gtatatatac   6300
gcacttttgc ccgtgctatg tggaagacta aacctccgaa gattgtgact caggtagtgc   6360
ggtatcggct agggacccaa accttgtcga tgccgatagc gctatcgaac gtaccccagc   6420
cggccgggag tatgtcggag gggacatacg agatcgtcaa gggtttgtgg ccaactggta   6480
aatttaaatg atgtcgacgc agtaggatgt cctgcacggg tcttttgtg gggtgtggag    6540 aaaggggtgc ttggagatgg aagccggtag aaccgggctg cttgtgcttg gagatggaag    6600
ccggtagaac cgggctgctt gggggatttt ggggccgctg ggctccaaag aggggtaggc   6660
atttcgttgg ggttacgtaa ttgcggcatt tgggtcctgc gcgcatgtcc cattggtcag   6720
aattagtccg gataggagac ttatcagcca atcacagcgc cggatccacc tgtaggttgg   6780
gttgggtggg agcacccctc cacagagtag agtcaaacag cagcagcaac atgatagttg    6840
ggggtgtgcg tgttaaagga aaaaaagaa gcttgggtta tattcccgct ctatttagag     6900
gttgcgggat agacgccgac ggagggcaat ggcgccatgg aaccttgcgg atatcgatac   6960
gccgcggcgg actgcgtccg aaccagctcc agcagcgttt tttccgggcc attgagccga    7020
ctgcgacccc gccaacgtgt cttggcccac gcactcatgt catgttggtg ttgggaggcc    7080 acttttaag tagcacaagg cacctagctc gcagcaaggt gtccgaacca agaagcggc      7140 tgcagtggtg caaacggggc ggaaacggcg ggaaaagcc acggggcac gaattgaggc      7200 acgccctcga atttgagacg agtcacggcc ccattcgccc gcgcaatggc tcgccaacgc   7260
ccggtctttt gcaccacatc aggttacccc aagccaaacc tttgtgttaa aaagcttaac    7320
atattatacc gaacgtaggt ttgggcgggc ttgctccgtc tgtccaaggc aacatttata    7380
taagggtctg catcgccggc tcaattgaat ctttttttctt cttctcttct ctatattcat   7440
tcttgaatta aacacacatc aatccatggc aaacagcagc gtgtgggatg atgtggtggg    7500
ccgcgtggag accggcgtgg accagtggat ggatggcgcc aagccgtacg cactcaccga   7560
tgggctcccg atgatggacg tgtccaccat gctggcattc gaggtgggat acatggccat   7620
gctgctcttc ggcatcccga tcatgaagca gatggagaag ccttttgagc tcaagaccat   7680
caagctcttg cacaacttgt ttctcttcgg actttccttg tacatgtgcg tggagaccat   7740
ccgccaggct atcctcggag gctacaaagt gtttggaaac gacatggaga agggcaacga    7800
gtctcatgct cagggcatgt ctcgcatcgt gtacgtgttc tacgtgtcca aggcatacga   7860
gttcttggat accgccatca tgatcctttg caagaagttc aaccaggttt ccttcttgca   7920
tgtgtaccac catgccactc atttttgcca tctggtgggc tatccgccaa gtacgctcca   7980
ggaggtgatg cgtacttttt cagtgatcct caactctttc gtgcacaccg tcatgtacgg   8040
catactactt cttctcctcc caagggttcg ggttcgtgaa gccaatcaag ccgtacatca   8100
ccacccttca gatgacccag ttcatggcaa tgcttgtgca gtccttgtac gactacctct   8160
```

| | |
|---|---|
| tcccatgcga ctacccacag gctcttgtgc agctccttgg agtgtacatg atcaccttgc | 8220 |
| ttgccctctt cggcaactt tttgtgcaga gctatcttaa aaagccaaaa aagagcaaga | 8280 |
| ccaactaaaa ctgcctgcat gatatgccgc tcgccggcgt tcgaattgac tcagaaagcg | 8340 |
| agttaaggcg acacgcaaac tctatatttt ttcaaacgtg ttgccgtcac tcattcgcca | 8400 |
| tctgttact acgtgtctgt tcaatgagca tgttcttgaa tctaaagaat ctcgaatgtt | 8460 |
| ttttaaaaaa agaattcgat atcaagctta cgcgtcgacc cgggtggacg tctagaggta | 8520 |
| cctagcaatt aacagatagt ttgccggtga taattctctt aacctcccac actcctttga | 8580 |
| cataacgatt tatgtaacga aactgaaatt tgaccagata ttgtgtccgc | 8630 |

<210> SEQ ID NO 73
<211> LENGTH: 18
<212> TYPE: DNA
<213> ORGANISM: Artificial Sequence
<220> FEATURE:
<223> OTHER INFORMATION: Primer GPDsense

<400> SEQUENCE: 73
atacgagatc gtcaaggg                                                    18

<210> SEQ ID NO 74
<211> LENGTH: 26
<212> TYPE: DNA
<213> ORGANISM: Artificial Sequence
<220> FEATURE:
<223> OTHER INFORMATION: Primer GPDantisense

<400> SEQUENCE: 74
gcggccgcgg attgatgtgt gtttaa                                           26

<210> SEQ ID NO 75
<211> LENGTH: 6339
<212> TYPE: DNA
<213> ORGANISM: Artificial Sequence
<220> FEATURE:
<223> OTHER INFORMATION: Plasmid pKR136
<220> FEATURE:
<221> NAME/KEY: misc_feature
<222> LOCATION: (4078)..(4078)
<223> OTHER INFORMATION: n is a, c, g, or t

<400> SEQUENCE: 75

| | |
|---|---|
| ggccgcgaca caagtgtgag agtactaaat aaatgctttg gttgtacgaa atcattacac | 60 |
| taaataaaat aatcaaagct tatatatgcc ttccgctaag gccgaatgca aagaaattgg | 120 |
| ttctttctcg ttatcttttg ccacttttac tagtacgtat taattactac ttaatcatct | 180 |
| ttgtttacgg ctcattatat ccgtacgtcg agtcgacctg caggcatgca agcttggcgt | 240 |
| aatcatggtc atagctgttt cctgtgtgaa attgttatcc gctcacaatt ccacacaaca | 300 |
| tacgagccgg aagcataaag tgtaaagcct ggggtgccta atgagtgagc taactcacat | 360 |
| taattgcgtt gcgctcactg cccgcttcc agtcgggaaa cctgtcgtgc cagctgcatt | 420 |
| aatgaatcgg ccaacgcgcg gggagaggcg gtttgcgtat tgggcgctct tccgcttcct | 480 |
| cgctcactga ctcgctgcgc tcggtcgttc ggctgcggcg agcggtatca gctcactcaa | 540 |
| aggcggtaat acggttatcc acagaatcag gggataacgc aggaaagaac atgtgagcaa | 600 |
| aaggccagca aaaggccagg aaccgtaaaa aggccgcgtt gctggcgttt tccataggc | 660 |
| tccgcccccc tgacgagcat cacaaaaatc gacgctcaag tcagaggtgg cgaaacccga | 720 |
| caggactata aagataccag gcgtttcccc ctggaagctc cctcgtgcgc tctcctgttc | 780 |

```
cgaccctgcc gcttaccgga tacctgtccg cctttctccc ttcgggaagc gtggcgcttt    840
ctcatagctc acgctgtagg tatctcagtt cggtgtaggt cgttcgctcc aagctgggct    900
gtgtgcacga accccccgtt cagcccgacc gctgcgcctt atccggtaac tatcgtcttg    960
agtccaaccc ggtaagacac gacttatcgc cactggcagc agccactggt aacaggatta   1020
gcagagcgag gtatgtaggc ggtgctacag agttcttgaa gtggtggcct aactacggct   1080
acactagaag gacagtattt ggtatctgcg ctctgctgaa gccagttacc ttcggaaaaa   1140
gagttggtag ctcttgatcc ggcaaacaaa ccaccgctgg tagcggtggt ttttttgttt   1200
gcaagcagca gattacgcgc agaaaaaaag gatctcaaga agatcctttg atctttcta    1260 cggggtctga cgctcagtgg aacgaaaact cacgttaagg gattttggtc atgagattat   1320 caaaaggat cttcacctag atccttttaa attaaaaatg aagttttaaa tcaatctaaa   1380
gtatatatga gtaaacttgg tctgacagtt accaatgctt aatcagtgag gcacctatct   1440
cagcgatctg tctatttcgt tcatccatag ttgcctgact ccccgtcgtg tagataacta   1500
cgatacggga gggcttacca tctggcccca gtgctgcaat gataccgcga gacccacgct   1560
caccggctcc agatttatca gcaataaacc agccagccgg aagggccgag cgcagaagtg   1620
gtcctgcaac tttatccgcc tccatccagt ctattaattg ttgccgggaa gctagagtaa   1680
gtagttcgcc agttaatagt ttgcgcaacg ttgttgccat tgctacaggc atcgtggtgt   1740
cacgctcgtc gtttggtatg gcttcattca gctccggttc ccaacgatca aggcgagtta   1800
catgatcccc catgttgtgc aaaaaagcgg ttagctcctt cggtcctccg atcgttgtca   1860
gaagtaagtt ggccgcagtg ttatcactca tggttatggc agcactgcat aattctctta   1920
ctgtcatgcc atccgtaaga tgcttttctg tgactggtga gtactcaacc aagtcattct   1980
gagaatagtg tatgcggcga ccgagttgct cttgcccggc gtcaatacgg gataataccg   2040
cgccacatag cagaacttta aaagtgctca tcattggaaa acgttcttcg gggcgaaaac   2100
tctcaaggat cttaccgctg ttgagatcca gttcgatgta acccactcgt gcacccaact   2160
gatcttcagc atcttttact ttcaccagcg tttctgggtg agcaaaaaca ggaaggcaaa   2220
atgccgcaaa aaagggaata agggcgacac ggaaatgttg aatactcata ctcttccttt   2280
ttcaatatta ttgaagcatt tatcagggtt attgtctcat gagcggatac atatttgaat   2340
gtatttagaa aaataaacaa ataggggttc cgcgcacatt tccccgaaaa gtgccacctg   2400
acgtctaaga aaccattatt atcatgacat taacctataa aaataggcgt atcacgaggc   2460
cctttcgtct cgcgcgtttc ggtgatgacg gtgaaaacct ctgacacatg cagctcccgg   2520
agacggtcac agcttgtctg taagcggatg ccgggagcag acaagcccgt cagggcgcgt   2580
cagcgggtgt tggcgggtgt cggggctggc ttaactatgc ggcatcagag cagattgtac   2640
tgagagtgca ccatatgcgg tgtgaaatac cgcacagatg cgtaaggaga aaataccgca   2700
tcaggcgcca ttcgccattc aggctgcgca actgttggga agggcgatcg gtgcgggcct   2760
cttcgctatt acgccagctg gcgaaagggg gatgtgctgc aaggcgatta agttgggtaa   2820
cgccagggtt ttcccagtca cgacgttgta aaacgacggc cagtgaattc gagctcggta   2880
cccggggatc ctctagacgt acgtcctcga agagaagggt taataacaca ttttttaaca   2940
tttttaacac aaattttagt tatttaaaaa tttattaaaa aatttaaaat aagaagagga   3000
actctttaaa taaatctaac ttacaaaatt tatgattttt aataagtttt caccaataaa   3060
aaatgtcata aaaatatgtt aaaaagtata ttatcaatat tctctttatg ataaataaaa   3120
```

-continued

```
agaaaaaaaa aataaaagtt aagtgaaaat gagattgaag tgactttagg tgtgtataaa   3180
tatatcaacc ccgccaacaa tttatttaat ccaaatatat tgaagtatat tattccatag   3240
cctttattta tttatatatt tattatataa aagctttatt tgttctaggt tgttcatgaa   3300 atatttttt ggttttatct ccgttgtaag aaaatcatgt gctttgtgtc gccactcact   3360
attgcagctt tttcatgcat tggtcagatt gacggttgat tgtattttg ttttttatgg   3420 ttttgtgtta tgacttaagt cttcatctct ttatctcttc atcaggtttg atggttacct   3480
aatatggtcc atgggtacat gcatggttaa attaggtggc caactttgtt gtgaacgata   3540 gaatttttt tatattaagt aaactatttt tatattatga aataataata aaaaaaatat   3600
tttatcatta ttaacaaaat catattagtt aatttgttaa ctctataata aaagaaatac   3660
tgtaacattc acattacatg gtaacatctt tccacccttt catttgtttt ttgtttgatg   3720 acttttttc ttgtttaaat ttatttccct tcttttaaat ttggaataca ttatcatcat   3780
atataaacta aaatactaaa aacaggatta cacaaatgat aaataataac acaaatattt   3840
ataaatctag ctgcaatata tttaaactag ctatatcgat attgtaaaat aaaactagct   3900
gcattgatac tgataaaaaa atatcatgtg ctttctggac tgatgatgca gtatactttt   3960
gacattgcct ttattttatt tttcagaaaa gctttcttag ttctgggttc ttcattattt   4020
gtttcccatc tccattgtga attgaatcat ttgcttcgtg tcacaaatac aatttagnta   4080
ggtacatgca ttggtcagat tcacggttta ttatgtcatg acttaagttc atggtagtac   4140
attacctgcc acgcatgcat tatattggtt agatttgata ggcaaatttg gttgtcaaca   4200
atataaatat aaataatgtt tttatattac gaaataacag tgatcaaaac aaacagtttt   4260
atctttatta acaagatttt gttttgtttt gatgacgttt tttaatgttt acgctttccc   4320
ccttcttttg aatttagaac actttatcat cataaaatca aatactaaaa aaattacata   4380
tttcataaat aataacacaa atatttttaa aaaatctgaa ataataatga acaatattac   4440
atattatcac gaaaattcat taataaaaat attatataaa taaaatgtaa tagtagttat   4500
atgtaggaaa aaagtactgc acgcataata tatacaaaaa gattaaaatg aactattata   4560
aataataaca ctaaattaat ggtgaatcat atcaaaataa tgaaaagta aataaaattt   4620 gtaattaact tctatatgta ttacacacac aaataataaa taatagtaaa aaaaattatg   4680
ataaatattt accatctcat aagatattta aaataatgat aaaaatatag attatttttt   4740
atgcaactag ctagccaaaa agagaacacg ggtatatata aaaagagtac ctttaaattc   4800
tactgtactt cctttattcc tgacgttttt atatcaagtg gacatacgtg aagattttaa   4860
ttatcagtct aaaatatttca ttagcactta atactttct gtttattcc tatcctataa   4920 gtagtcccga ttctcccaac attgcttatt cacacaacta actaagaaag tcttccatag   4980 cccccccaagc ggccgcatgg gaacggacca aggaaaaacc ttcacctggg aagagctggc   5040
ggcccataac accaaggacg acctactctt ggccatccgc ggcagggtgt acgatgtcac   5100
aaagttcttg agccgccatc ctggtggagt ggacactctc ctgctcggag ctggccgaga   5160
tgttactccg gtctttgaga tgtatcacgc gtttggggct gcagatgcca ttatgaagaa   5220
gtactatgtc ggtacactgg tctcgaatga gctgcccatc ttcccggagc caacggtgtt   5280
ccacaaaacc atcaagacga gagtcgaggg ctactttacg gatcggaaca ttgatcccaa   5340
gaatagacca gagatctggg gacgatacgc tcttatctttt ggatccttga tcgcttccta   5400
ctacgcgcag ctcttttgtgc ctttcgttgt cgaacgcaca tggcttcagg tggtgtttgc   5460
aatcatcatg ggatttgcgt gcgcacaagt cggactcaac cctcttcatg atgcgtctca   5520
```

```
cttttcagtg acccacaacc ccactgtctg gaagattctg ggagccacgc acgacttttt     5580
caacggagca tcgtacctgg tgtggatgta ccaacatatg ctcggccatc acccctacac     5640
caacattgct ggagcagatc ccgacgtgtc gacgtctgag cccgatgttc gtcgtatcaa     5700
gcccaaccaa aagtggtttg tcaaccacat caaccagcac atgtttgttc ctttcctgta     5760
cggactgctg gcgttcaagg tgcgcattca ggacatcaac attttgtact tgtcaagac     5820 caatgacgct attcgtgtca atcccatctc gacatggcac actgtgatgt tctgggcgg      5880 caaggctttc tttgtctggt atcgcctgat tgttccctg cagtatctgc cctgggcaa       5940 ggtgctgctc ttgttcacgg tcgcggacat ggtgtcgtct tactggctgg cgctgacctt     6000
ccaggcgaac cacgttgttg aggaagttca gtggccgttg cctgacgaga acggatcat      6060 ccaaaaggac tgggcagcta tgcaggtcga gactacgcag gattacgcac acgattcgca     6120
cctctggacc agcatcactg gcagcttgaa ctaccaggct gtgcaccatc tgttccccaa     6180
cgtgtcgcag caccattatc ccgatattct ggccatcatc aagaacacct gcagcgagta     6240
caaggttcca taccttgtca aggatacgtt ttggcaagca tttgcttcac atttggagca     6300
cttgcgtgtt cttggactcc gtcccaagga agagtaggc                           6339

<210> SEQ ID NO 76
<211> LENGTH: 8319
<212> TYPE: DNA
<213> ORGANISM: Artificial Sequence
<220> FEATURE:
<223> OTHER INFORMATION: Plasmid pY98

<400> SEQUENCE: 76
ggccgccacc gcggcccgag attccggcct cttcggccgc caagcgaccc gggtggacgt       60
ctagaggtac ctagcaatta acagatagtt tgccggtgat aattctctta acctcccaca      120
ctcctttgac ataacgattt atgtaacgaa actgaaattt gaccagatat tgtgtccgcg      180
gtggagctcc agcttttgtt ccctttagtg agggttaatt tcgagcttgg cgtaatcatg      240
gtcatagctg tttcctgtgt gaaattgtta tccgctcaca attccacaca acgtacgagc      300
cggaagcata agtgtaaag cctggggtgc ctaatgagtg agctaactca cattaattgc       360
gttgcgctca ctgcccgctt tccagtcggg aaacctgtcg tgccagctgc attaatgaat      420
cggccaacgc gcgggagag gcggtttgcg tattgggcgc tcttccgctt cctcgctcac       480
tgactcgctg cgctcggtcg ttcggctgcg gcgagcggta tcagctcact caaaggcggt      540
aatacggtta tccacagaat caggggataa cgcaggaaag aacatgtgag caaaaggcca      600
gcaaaaggcc aggaaccgta aaaaggccgc gttgctggcg ttttccata ggctccgccc       660 ccctgacgag catcacaaaa atcgacgctc aagtcagagg tggcgaaacc cgacaggact     720
ataaagatac caggcgtttc ccctggaag ctccctcgtg cgctctcctg ttccgaccct      780
gccgcttacc ggatacctgt ccgcctttct cccttcggga agcgtggcgc tttctcatag     840
ctcacgctgt aggtatctca gttcggtgta ggtcgttcgc tccaagctgg gctgtgtgca     900 cgaaccccc gttcagcccg accgctgcgc cttatccggt aactatcgtc ttgagtccaa      960
cccggtaaga cacgacttat cgccactggc agcagccact ggtaacagga ttagcagagc     1020
gaggtatgta ggcggtgcta cagagttctt gaagtggtgg cctaactacg gctacactag     1080
aaggacagta tttggtatct gcgctctgct gaagccagtt accttcggaa aaagagttgg     1140
tagctcttga tccggcaaac aaaccaccgc tggtagcggt ggttttttg tttgcaagca     1200
```

```
gcagattacg cgcagaaaaa aaggatctca agaagatcct ttgatctttt ctacggggtc    1260
tgacgctcag tggaacgaaa actcacgtta agggattttg gtcatgagat tatcaaaaag    1320
gatcttcacc tagatccttt taaattaaaa atgaagtttt aaatcaatct aaagtatata    1380
tgagtaaact tggtctgaca gttaccaatg cttaatcagt gaggcaccta tctcagcgat    1440
ctgtctattt cgttcatcca tagttgcctg actcccgtc gtgtagataa ctacgatacg    1500
ggagggctta ccatctggcc ccagtgctgc aatgataccg cgagacccac gctcaccggc    1560
tccagattta tcagcaataa accagccagc cggaagggcc gagcgcagaa gtggtcctgc    1620
aactttatcc gcctccatcc agtctattaa ttgttgccgg gaagctagag taagtagttc    1680
gccagttaat agtttgcgca acgttgttgc cattgctaca ggcatcgtgg tgtcacgctc    1740
gtcgtttggt atggcttcat tcagctccgg ttcccaacga tcaaggcgag ttacatgatc    1800
ccccatgttg tgcaaaaaag cggttagctc cttcggtcct ccgatcgttg tcagaagtaa    1860
gttggccgca gtgttatcac tcatggttat ggcagcactg cataattctc ttactgtcat    1920
gccatccgta agatgctttt ctgtgactgg tgagtactca accaagtcat tctgagaata    1980
gtgtatgcgg cgaccgagtt gctcttgccc ggcgtcaata cgggataata ccgcgccaca    2040
tagcagaact ttaaaagtgc tcatcattgg aaaacgttct cggggcgaaa actctcaag     2100 gatcttaccg ctgttgagat ccagttcgat gtaaccccact cgtgcaccca actgatcttc    2160
agcatctttt actttcacca gcgtttctgg gtgagcaaaa acaggaaggc aaaatgccgc    2220
aaaaaaggga ataagggcga cacggaaatg ttgaatactc atactcttcc ttttcaata    2280 ttattgaagc atttatcagg gttattgtct catgagcgga tacatatttg aatgtattta    2340
gaaaaataaa caaatagggg ttccgcgcac atttccccga aaagtgccac ctgacgcgcc    2400
ctgtagcggc gcattaagcg cggcgggtgt ggtggttacg cgcagcgtga ccgctacact    2460
tgccagcgcc ctagcgcccg ctcctttcgc tttcttccct tcctttctcg ccacgttcgc    2520
cggctttccc cgtcaagctc taaatcgggg gctcccttta gggttccgat ttagtgcttt    2580
acggcacctc gaccccaaaa aacttgatta gggtgatggt tcacgtagtg gccatcgcc     2640 ctgatagacg gttttcgcc ctttgacgtt ggagtccacg ttctttaata gtggactctt     2700
gttccaaact ggaacaacac tcaaccctat ctcggtctat tcttttgatt tataagggat    2760
tttgccgatt tcggcctatt ggttaaaaaa tgagctgatt taacaaaaat ttaacgcgaa    2820
ttttaacaaa atattaacgc ttacaatttc cattcgccat tcaggctgcg caactgttgg    2880
gaagggcgat cggtgcgggc ctcttcgcta ttacgccagc tggcgaaagg gggatgtgct    2940
gcaaggcgat taagttgggt aacgccaggg ttttcccagt cacgacgttg taaaacgacg    3000
gccagtgaat tgtaatacga ctcactatag ggcgaattgg gtaccgggcc cccctcgag    3060 gtcgatggtg tcgataagct tgatatcgaa ttcatgtcac acaaaccgat cttcgcctca    3120
aggaaaccta attctacatc cgagagactg ccgagatcca gtctacactg attaattttc    3180
gggccaataa tttaaaaaaa tcgtgttata taatattata tgtattatat atatacatca    3240
tgatgatact gacagtcatg tcccattgct aaatagacag actccatctg ccgcctccaa    3300
ctgatgttct caatatttaa ggggtcatct cgcattgttt aataataaac agactccatc    3360
taccgcctcc aaatgatgtt ctcaaaatat attgtatgaa cttatttta ttacttagta    3420 ttattagaca acttacttgc tttatgaaaa acacttccta tttaggaaac aatttataat    3480
ggcagttcgt tcatttaaca atttatgtag aataaatgtt ataaatgcgt atgggaaatc    3540
ttaaatatgg atagcataaa tgatatctgc attgcctaat tcgaaatcaa cagcaacgaa    3600
```

```
aaaaatccct tgtacaacat aaatagtcat cgagaaatat caactatcaa agaacagcta    3660
ttcacacgtt actattgaga ttattattgg acgagaatca cacactcaac tgtctttctc    3720
tcttctagaa atacaggtac aagtatgtac tattctcatt gttcatactt ctagtcattt    3780
catcccacat attccttgga tttctctcca atgaatgaca ttctatcttg caaattcaac    3840
aattataata agatatacca aagtagcggt atagtggcaa tcaaaaagct tctctggtgt    3900
gcttctcgta tttattttta ttctaatgat ccattaaagg tatatattta tttcttgtta    3960
tataatcctt ttgtttatta catgggctgg atacataaag gtattttgat ttaatttttt    4020
gcttaaattc aatcccccct cgttcagtgt caactgtaat ggtaggaaat taccatactt    4080
ttgaagaagc aaaaaaaatg aaagaaaaaa aaatcgtat ttccaggtta gacgttccgc     4140
agaatctaga atgcggtatg cggtacattg ttcttcgaac gtaaaagttg cgctccctga    4200
gatattgtac attttttgctt ttacaagtac aagtacatcg tacaactatg tactactgtt   4260
gatgcatcca caacagtttg ttttgttttt ttttgttttt ttttttttcta atgattcatt   4320 accgctatgt atacctactt gtacttgtag taagccgggt tattggcgtt caattaatca    4380
tagacttatg aatctgcacg gtgtgcgctg cgagttactt ttagcttatg catgctactt    4440
gggtgtaata ttgggatctg ttcggaaatc aacggatgct caaccgattt cgacagtaat    4500
taattaagtc atacacaagt cagctttctt cgagcctcat ataagtataa gtagttcaac    4560
gtattagcac tgtacccagc atctccgtat cgagaaacac aacaacatgc cccattggac    4620
agatcatgcg gatacacagg ttgtgcagta tcatacatac tcgatcagac aggtcgtctg    4680
accatcatac aagctgaaca agcgctccat acttgcacgc tctctatata cacagttaaa    4740
ttacatatcc atagtctaac ctctaacagt taatcttctg gtaagcctcc cagccagcct    4800
tctggtatcg cttggcctcc tcaataggat ctcggttctg gccgtacaga cctcggccga    4860
caattatgat atccgttccg gtagacatga catcctcaac agttcggtac tgctgtccga    4920
gagcgtctcc cttgtcgtca agacccaccc cggggggtcag aataagccag tcctcagagt   4980
cgcccttagg tcggttctgg gcaatgaagc caaccacaaa ctcggggtcg gatcgggcaa    5040
gctcaatggt ctgcttggag tactcgccag tggccagaga gcccttgcaa gacagctcgg    5100
ccagcatgag cagacctctg gccagcttct cgttgggaga ggggactagg aactccttgt    5160
actgggagtt ctcgtagtca gagacgtcct ccttcttctg ttcagagaca gtttcctcgg    5220
caccagctcg caggccagca atgattccgg ttccgggtac accgtgggcg ttggtgatat    5280
cggaccactc ggcgattcgg tgacaccggt actggtgctt gacagtgttg ccaatatctg    5340
cgaactttct gtcctcgaac aggaagaaac cgtgcttaag agcaagttcc ttgagggga    5400 gcacagtgcc ggcgtaggtg aagtcgtcaa tgatgtcgat atgggttttg atcatgcaca    5460
cataaggtcc gaccttatcg gcaagctcaa tgagctcctt ggtggtggta acatccagag    5520
aagcacacag gttggttttc ttggctgcca cgagcttgag cactcgagcg gcaaaggcgg    5580
acttgtggac gttagctcga gcttcgtagg agggcatttt ggtggtgaag aggagactga    5640
aataaattta gtctgcagaa ctttttatcg gaaccttatc tggggcagtg aagtatatgt    5700
tatggtaata gttacgagtt agttgaactt atagatagac tggactatac ggctatcggt    5760
ccaaattaga aagaacgtca atggctctct gggcgtcgcc tttgccgaca aaaatgtgat    5820
catgatgaaa gccagcaatg acgttgcagc tgatattgtt gtcggccaac cgcgccgaaa    5880
acgcagctgt cagacccaca gcctccaacg aagaatgtat cgtcaaagtg atccaagcac    5940
```

```
actcatagtt ggagtcgtac tccaaaggcg gcaatgacga gtcagacaga tactcgtcga    6000
cgcagtagga tgtcctgcac gggtcttttt gtggggtgtg gagaaagggg tgcttggaga    6060
tggaagccgg tagaaccggg ctgcttgtgc ttggagatgg aagccggtag aaccgggctg    6120
cttgggggga tttgggccgc ctgggctcca aagaggggta ggcatttcgt tggggttacg    6180
taattgcggc atttgggtcc tgcgcgcatg tcccattggt cagaattagt ccggatagga    6240
gacttatcag ccaatcacag cgccggatcc acctgtaggt tgggttgggt gggagcaccc    6300
ctccacagag tagagtcaaa cagcagcagc aacatgatag ttgggggtgt gcgtgttaaa    6360
ggaaaaaaaa gaagcttggg ttatattccc gctctattta gaggttgcgg gatagacgcc    6420
gacggagggc aatggcgcca tggaaccttg cggatatcga tacgccgcgg cggactgcgt    6480
ccgaaccagc tccagcagcg ttttttccgg gccattgagc cgactgcgac cccgccaacg    6540
tgtcttggcc cacgcactca tgtcatgttg gtgttgggag gccactttt aagtagcaca    6600
aggcacctag ctcgcagcaa ggtgtccgaa ccaaagaagc ggctgcagtg gtgcaaacgg    6660
ggcggaaacg gcgggaaaaa gccacggggg cacgaattga ggcacgccct cgaatttgag    6720
acgagtcacg gccccattcg cccgcgcaat ggctcgccaa cgcccggtct tttgcaccac    6780
atcaggttac cccaagccaa accttttgtgt taaaaagctt aacatattat accgaacgta    6840
ggtttgggcg ggcttgctcc gtctgtccaa ggcaacattt atataagggt ctgcatcgcc    6900
ggctcaattg aatctttttt cttcttctct tctctatatt cattcttgaa ttaaacacac    6960
atcaatccgc ggccgcatgg gaacggacca aggaaaaacc ttcacctggg aagagctggc    7020
ggcccataac accaaggacg acctactctt ggccatccgc ggcagggtgt acgatgtcac    7080
aaagttcttg agccgccatc ctggtggagt ggacactctc ctgctcggag ctggccgaga    7140
tgttactccg gtctttgaga tgtatcacgc gtttggggct gcagatgcca ttatgaagaa    7200
gtactatgtc ggtacactgg tctcgaatga gctgcccatc ttcccggagc caacggtgtt    7260
ccacaaaacc atcaagacga gagtcgaggg ctactttacg gatcggaaca ttgatcccaa    7320
gaatagacca gagatctggg gacgatacgc tcttatcttt ggatccttga tcgcttccta    7380
ctacgcgcag ctctttgtgc ctttcgttgt cgaacgcaca tggcttcagg tggtgtttgc    7440
aatcatcatg ggatttgcgt gcgcacaagt cggactcaac cctcttcatg atgcgtctca    7500
cttttcagtg acccacaacc ccactgtctg gaagattctg ggagccacgc acgacttttt    7560
caacggagca tcgtacctgg tgtggatgta ccaacatatg ctcggccatc acccctacac    7620
caacattgct ggagcagatc ccgacgtgtc gacgtctgag cccgatgttc gtcgtatcaa    7680
gcccaaccaa aagtggtttg tcaaccacat caaccagcac atgtttgttc ctttcctgta    7740
cggactgctg gcgttcaagg tgcgcattca ggacatcaac attttgtact ttgtcaagac    7800
caatgacgct attcgtgtca atcccatctc gacatggcac actgtgatgt tctggggcgg    7860
caaggctttc tttgtctggt atcgcctgat tgttcccctg cagtatctgc ccctgggcaa    7920
ggtgctgctc ttgttcacgg tcgcggacat ggtgtcgtct tactggctgg cgctgacctt    7980
ccaggcgaac cacgttgttg aggaagttca gtggccgttg cctgacgaga acgggatcat    8040
ccaaaaggac tgggcagcta tgcaggtcga gactacgcag gattacgcac acgattcgca    8100
cctctgacc agcatcactg gcagcttgaa ctaccaggct gtgcaccatc tgttcccaa    8160
cgtgtcgcag caccattatc ccgatattct ggccatcatc aagaacacct gcagcgagta    8220
```

```
caaggttcca taccttgtca aggatacgtt ttggcaagca tttgcttcac atttggagca    8280
cttgcgtgtt cttggactcc gtcccaagga agagtaggc                          8319
```